United States Patent
Rae et al.

(10) Patent No.: US 10,137,151 B2
(45) Date of Patent: *Nov. 27, 2018

(54) THERAPEUTIC DETOXIFICATION COMPOSITIONS AND METHODS OF MAKING AND USING SAME

(71) Applicant: Immutrix Therapeutics, Inc., Rapid City, SD (US)

(72) Inventors: Carol A Rae, Rapid City, SD (US); Jan Simoni, Rapid City, SD (US); Grace Simoni, Rapid City, SD (US); John F. Moeller, Rapid City, SD (US)

(73) Assignee: IMMUTRIX THERAPEUTICS, INC., Rapid City, SD (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/500,893

(22) PCT Filed: Apr. 17, 2015

(86) PCT No.: PCT/US2015/026373
§ 371 (c)(1),
(2) Date: Jan. 31, 2017

(87) PCT Pub. No.: WO2015/161200
PCT Pub. Date: Oct. 22, 2015

(65) Prior Publication Data
US 2017/0258832 A1    Sep. 14, 2017

Related U.S. Application Data

(60) Provisional application No. 61/981,061, filed on Apr. 17, 2014.

(51) Int. Cl.
| A61K 33/44 | (2006.01) |
| A61M 1/36 | (2006.01) |
| B01J 47/026 | (2017.01) |
| A61K 9/14 | (2006.01) |

(52) U.S. Cl.
CPC ............ *A61K 33/44* (2013.01); *A61K 9/14* (2013.01); *A61M 1/3679* (2013.01); *B01J 47/026* (2013.01)

(58) Field of Classification Search
CPC ....... A61K 33/44; A61K 9/14; A61M 1/3679; B01J 47/026
See application file for complete search history.

(56) References Cited

U.S. PATENT DOCUMENTS

| 2004/0228829 A1* | 11/2004 | Roberts | A61K 35/16 424/78.1 |
| 2006/0063849 A1* | 3/2006 | Lin | H01B 1/122 521/99 |
| 2012/0074060 A1* | 3/2012 | Lass | C02F 1/444 210/636 |
| 2013/0072845 A1* | 3/2013 | Tennison | A61M 1/34 604/5.04 |
| 2014/0011666 A1* | 1/2014 | Yoshizaki | A24D 3/163 502/7 |

FOREIGN PATENT DOCUMENTS

| JP | WO 2012132251 A1 * | 10/2012 | ............. A24D 3/163 |
| WO | WO 2013136094 A1 * | 9/2013 | ........... A61K 9/0053 |
| WO | 2015161200 A1 | 10/2015 | |

OTHER PUBLICATIONS

Filing receipt and specification for provisional patent application entitled "Plasma Detoxification," by Craig P. Roberts, et al., filed Apr. 17, 2014 as U.S. Appl. No. 61/981,061.

* cited by examiner

*Primary Examiner* — Mark V Stevens
(74) *Attorney, Agent, or Firm* — Wick Phillips Gould & Martin LLP; Jerry C. Harris, Jr.

(57) ABSTRACT

A three component composition for use in the treatment of an autoimmune disease where the first component comprises a bimodal synthetic carbon particle mixture; the second component comprises a bimodal synthetic carbon particle mixture and an anion exchange resin and the third component comprises a bimodal synthetic carbon particle mixture and a cation exchange resin.

19 Claims, 17 Drawing Sheets

THERAPEUTIC DETOXIFICATION COMPOSITIONS AND METHODS OF MAKING AND USING SAME

CROSS-REFERENCE TO RELATED APPLICATIONS

This application is a filing under 35 U.S.C. 371 of International Application No. PCT/US2015/026373 filed Apr. 17, 2015, entitled "Therapeutic Detoxification Compositions and Methods of Making and Using Same," claiming priority of U.S. Provisional Application No. 61/981,061, filed on Apr. 17, 2014 and entitled "Plasma Detoxification," which is incorporated by reference herein in its entirety.

TECHNICAL FIELD

Disclosed herein are compositions, systems, and methods for treatment of subjects suffering from a medical condition. More specifically disclosed herein are methodologies for extracorporeal removal of disease mediators, poisons, and drugs from said subjects.

BACKGROUND

Many diseases still lack cures. The main reasons are not yet well-established etiologies and/or not fully effective surgical interventions and/or pharmacological treatments. Lack of appropriate treatment can result in progression of diseases into chronic and eventually comorbid states. Thus, an ongoing need exists for compositions and methodologies for the treatment of diseases.

SUMMARY

Disclosed herein is a three component composition for use in the treatment of an of an autoimmune disease where the first component comprises a bimodal synthetic carbon particle mixture; the second component comprises a bimodal synthetic carbon particle mixture and an anion exchange resin and the third component comprises a bimodal synthetic carbon particle mixture and a cation exchange resin.

Also disclosed herein is a three component composition for use in the treatment of a Class A condition where the first component comprises a bimodal synthetic carbon particle mixture; the second component comprises the bimodal synthetic carbon particle mixture and an anion exchange resin in a ratio of from about 10:1 to about 7:3 and the third component comprises the bimodal synthetic carbon particle mixture and a cation exchange resin of from about 10:1 to about 7:3.

Also disclosed herein is a composition comprising 80 weight percent of a first synthetic carbon particle and 20 weight percent of a second synthetic carbon particle for use in the treatment of an overdose of a drug or poison wherein the first synthetic carbon particle has a pore size of 125 μm and the second synthetic carbon particle has a pore size of 250 μm.

Also disclosed herein is a method of detoxifying plasma obtained from a subject having a Class A condition comprising (i) contacting the plasma with composition comprising a bimodal synthetic carbon; an anionic resin and a cationic resin.

BRIEF DESCRIPTION OF THE DRAWINGS

For a more complete understanding of the present disclosure and the advantages thereof, reference is now made to the following brief description, taken in connection with the accompanying drawings and detailed description, wherein like reference numerals represent like parts.

DETAILED DESCRIPTION

Figure 1:
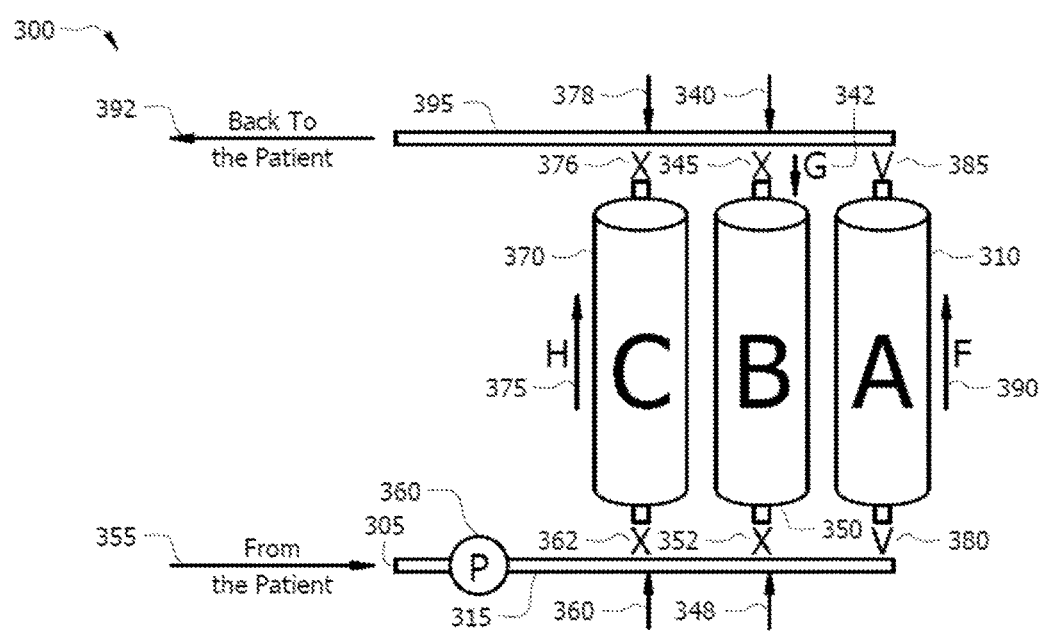
FIG. 1 represents embodiments of devices of the present disclosure.

Disclosed herein are methodologies and compositions useful for the treatment of subjects suffering from a disease, disorder, or dysfunction. Examples of such diseases, disorders, or dysfunctions include without limitation autoimmune, metabolic, inflammatory, degenerative and neoplastic disorders, as well as poisonings and drug overdoses. Also disclosed herein are apparatuses useful in the treatment of subjects suffering from these conditions. Hereinafter, unless otherwise specified, the collection of diseases, disorders, or dysfunctions that may be treated utilizing the compositions disclosed herein are collectively termed "medical conditions." The term "subject," as used herein, comprises any and all organisms and includes the term "patient." A subject to be treated according to the methods described herein may be one who has been diagnosed by a medical practitioner as suffering from a medical condition. Diagnosis may be performed by any suitable means. One skilled in the art will understand that a subject to be treated according to the present disclosure may have been subjected to standard tests to diagnose the medical conditions. As known to the ordinarily skilled artisan, the clinical features of medical conditions of the type disclosed herein vary according to the pathomechanisms.

Herein "treating" refers to utilizing the disclosed methodologies and compositions for therapeutic purposes. Therapeutic treatment may be administered, for example, to a subject suffering from the medical condition in order to improve or stabilize the subject's condition. Thus, in the claims and embodiments described herein, treating refers to a subject undergoing for therapeutic purposes, the methodologies disclosed herein.

In some instances, as compared with an equivalent untreated control, treatment may ameliorate the medical condition or a symptom thereof. As used herein, amelioration of the medical condition or symptoms thereof by undergoing the methodologies disclosed herein refers to any lessening, whether lasting or transient, which can be attributed to or associated with undergoing the methodologies disclosed herein. Confirmation of treatment can be assessed by detecting an improvement in or the absence of symptoms, or by the inability to detect the presence of the medical condition in the treated subject.

In an embodiment, a method of the present disclosure comprises (i) contacting the bodily fluid of a subject with an apparatus for removal of one or more components present in the bodily fluid to produce a decontaminated bodily fluid; and returning at least a portion of the decontaminated bodily fluid to a subject. In another embodiment, a method of the present disclosure comprises (i) contacting the plasma of a subject with an apparatus for removal of one or more components present in the plasma to produce a decontaminated plasma; and returning at least a portion of the decontaminated plasma to a subject. In an embodiment, the plasma contains blood cellular components. Alternatively, the plasma does not contain blood cellular components. As used herein the term "bodily fluid," includes without limitation inter alia plasma without blood cellular components, plasma with blood cellular components (i.e., whole blood) and cerebrospinal fluid. Herein the term "blood cellular components" refers to components such as red corpuscles (erythrocytes), platelets (thrombocytes), and five types of white corpuscles (leukocytes). In an embodiment, at least a portion of the bodily fluid is removed from the subject. In an embodiment, the bodily fluid comprises whole blood or plasma.

In an alternative embodiment, a method of the present disclosure comprises contacting at least a portion of the bodily fluid of a subject suffering from a medical condition, with an apparatus of the type disclosed herein. The method may further comprise recovering at least a portion of the subject's bodily fluid to obtain a decontaminated bodily fluid. The method may further comprise administering at least a portion of the decontaminated bodily fluid to the subject in order to treat the medical condition.

In an alternative embodiment, a method of the present disclosure comprises identifying a subject suffering from a medical condition. The method may further comprise performing extracorporeal cleansing of at least a portion of the subject's bodily fluid utilizing the apparatuses and compositions disclosed herein to generate a decontaminated bodily fluid. The method may further comprise administering at least a portion of the decontaminated bodily fluid to the subject.

In an embodiment, any of the methods of the present disclosure comprises obtaining a blood sample from a subject diagnosed with a medical condition.

In an embodiment, a sample of a bodily fluid (e.g., blood) is obtained from a subject who is in fluid communication with an extracorporeal apparatus. The subject may suffer from a medical condition. An embodiment of apparatuses suitable for use in the present disclosure is depicted in FIG. 1. In an embodiment, the apparatus 300 comprises an inlet 305 in fluid communication with a pump 360 which regulates access and fluid communication with conduit 315. The apparatus 300 may be connected to a subject through establishing a means of blood flow from the subject to inlet 305. An arterial access of the subject 355 may be used to establish a means of blood flow from the subject to the inlet 305. As a safety measure, apparatus 300 in one embodiment includes a plurality of electrodes (not shown), such as two to four electrodes, which provide an access disconnection sensor, which is integrated half in the arterial line 305 and half in the venous line 392 to detect access disconnection of the subject from the apparatus 300. An alternative embodiment for detection of accidental needle disconnections is the use of a conductive blanket underneath the subject's access. In such embodiments, the presence of blood changes the conductivity of the blanket and sets off an alarm and stops the pumps.

With reference to FIG. 1, a methodology of the type disclosed herein comprises establishing fluid communication between a subject's blood flow as accessed in acute situation through a jugular, subclavian or femoral vein with double lumen catheter of the subject 355 and the inlet 305 of the apparatus 300. Other options are chronic vascular accesses used in hemodialysis that are created by an earlier surgical procedure: (i) native arteriovenous fistulas (native AVFs), (ii) arteriovenous shunts using graft material (AV graft), and (iii) tunneled double-lumen catheters. The pump 360 regulates the flow of the subject's blood to the remainder of the apparatus 300 through conduit 315. Conduit 315 may be a pipe or flow line comprised of material suitable for use in the methodologies disclosed herein. In an embodiment, the subject's blood is allowed to flow through conduit 315 until it reaches valve 380 which when in the on position allows the blood flow to enter column A 310 in a particular flow direction 390. Blood may be pumped through column A 310 and exit the column thorough an outlet regulated by a valve 385. Blood exiting from column A 310 through the outlet regulated by valve 385 may enter conduit 395 where it is pumped to inlet port 340 whose access is regulated by valve 345. When valve 345 is in the on position, the blood may be pumped from inlet port 340 to column B 350 where it moves in flow direction G 342 through column B 350 to outlet port 348 which is regulated by valve 352. When valve 352 is in the on position the blood may flow from column B 350 into conduit 315. In an embodiment, the subject's blood is allowed to flow through conduit 315 until it reaches inlet port 360 which is regulated by valve 362 which when in the on position allows the blood flow to enter column C 370 in a particular flow direction H 375. The blood may exit column C 370 via outlet port 378 which is regulated by valve 376 which when in the on position allows the blood to flow into conduit 395 and back to the jugular, subclavian or femoral vein, or the vascular accesses that are created by an earlier surgical procedure: (i) native arteriovenous fistulas (native AVFs), (ii) arteriovenous shunts using graft material (AV graft), and (iii) tunneled double-lumen catheters, of the subject 392.

In an embodiment, the rate of flow of a bodily fluid (e.g., plasma, whole blood) through apparatus 300 may be regulated to provide some user and/or process goal. For example, the rate of blood flow through apparatus 300 may range from about 1 mL/min to about 300 mL/min, alternatively from about 25 mL/min to about 300 mL/min, alternatively from about 25 mL/min to about 150 mL/min, or alternatively from about 150 mL/min to about 300 mL/min. In an embodiment, treatment of a subject suffering from a medical condition may require the subject be in fluid communication with apparatus 300 for a period of time ranging from about 1 hour to about 24 hours, alternatively from about 1 hour to about 12 hours, or alternatively from about 1 hour to about 6 hours. In an embodiment, the subject is in fluid communication with the apparatus 300 for a time period sufficient to allow from about 0.5 to about 10× the total blood volume of the subject to circulate through the apparatus 300. Alternatively from about 1 to about 10× the total blood volume of the subject is allowed to circulate through the apparatus. In yet another embodiment, the blood volume circulated through the apparatus (e.g., apparatus 300) may range from about 5 liters to about 72 liters, alternatively form about 10 liters to about 60 liters, or alternatively from about 36 liters to about 54 liters and may occur in a time period ranging from about 1 hour to about 6 hours or alternatively from about 3 hours to about 4 hours. In some embodiments, the subject suffering from an autoimmune, metabolic, inflammatory, degenerative or neoplastic disorder, as well as poisoning or drug overdose, may undergo treatments where a subject is placed in fluid communication with the apparatus a plurality of times as deemed sufficient to address subject's particular medical condition.

Figure 2:
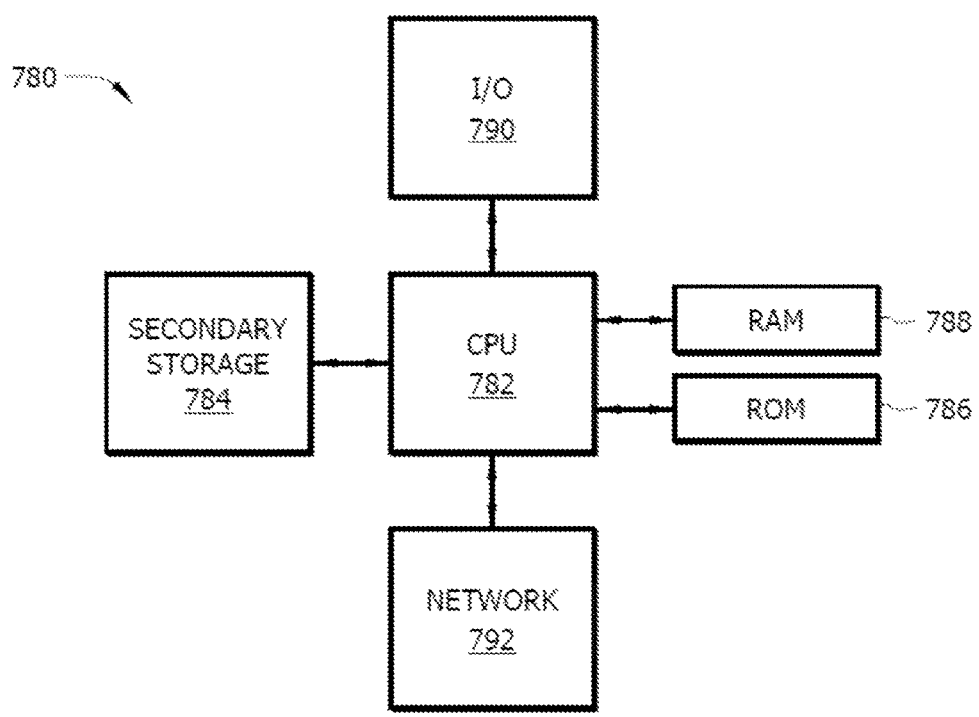
FIG. 2 depicts embodiments of a computer system suitable for use in the present disclosure.

It is to be understood that FIG. 1 presents an embodiment of an apparatus suitable for use in the present disclosure. Additional routine modifications to the apparatus are contemplated by the present disclosure. For example, the apparatus may contain less than the 3 columns or the columns may be disposed in positions other than perpendicular to conduits 315 and 395. In an embodiment, the apparatus 300 may be associated with a computer system. FIG. 2 illustrates a computer system 780 suitable for implementing one or more embodiments disclosed herein. The computer system 780 includes a processor 782 (which may be referred to as a central processor unit or CPU) that is in communication with memory devices including secondary storage 784, read only memory (ROM) 786, random access memory (RAM) 788, input/output (I/O) devices 790, and network connectivity devices 792. The processor 782 may be implemented as one or more CPU chips.

It is understood that by programming and/or loading executable instructions onto the computer system 780, at least one of the CPU 782, the RAM 788, and the ROM 786 are changed, transforming the computer system 780 in part into a particular machine or apparatus having the novel functionality taught by the present disclosure. It is fundamental to the electrical engineering and software engineering arts that functionality that can be implemented by loading executable software into a computer can be converted to a hardware implementation by well-known design rules. Decisions between implementing a concept in software versus hardware typically hinge on considerations of stability of the design and numbers of units to be produced rather than any issues involved in translating from the software domain to the hardware domain. Generally, a design that is still subject to frequent change may be preferred to be implemented in software, because re-spinning a hardware implementation is more expensive than re-spinning a software design. Generally, a design that is stable that will be produced in large volume may be preferred to be implemented in hardware, for example in an application specific integrated circuit (ASIC), because for large production runs the hardware implementation may be less expensive than the software implementation. Often a design may be developed and tested in a software form and later transformed, by well-known design rules, to an equivalent hardware implementation in an application specific integrated circuit that hardwires the instructions of the software. In the same manner as a machine controlled by a new ASIC is a particular machine or apparatus, likewise a computer that has been programmed and/or loaded with executable instructions may be viewed as a particular machine or apparatus.

The secondary storage 784 is typically comprised of one or more disk drives or tape drives and is used for non-volatile storage of data and as an over-flow data storage device if RAM 788 is not large enough to hold all working data. Secondary storage 784 may be used to store programs which are loaded into RAM 788 when such programs are selected for execution. The ROM 786 is used to store instructions and perhaps data which are read during program execution. ROM 786 is a non-volatile memory device which typically has a small memory capacity relative to the larger memory capacity of secondary storage 784. The RAM 788 is used to store volatile data and perhaps to store instructions. Access to both ROM 786 and RAM 788 is typically faster than to secondary storage 784. The secondary storage 784, the RAM 788, and/or the ROM 786 may be referred to in some contexts as computer readable storage media and/or non-transitory computer readable media.

I/O devices 790 may include printers, video monitors, liquid crystal displays (LCDs), touch screen displays, keyboards, keypads, switches, dials, mice, track balls, voice recognizers, card readers, paper tape readers, or other well-known input devices.

The network connectivity devices 792 may take the form of modems, modem banks, Ethernet cards, universal serial bus (USB) interface cards, serial interfaces, token ring cards, fiber distributed data interface (FDDI) cards, wireless local area network (WLAN) cards, radio transceiver cards such as code division multiple access (CDMA), global system for mobile communications (GSM), long-term evolution (LTE), worldwide interoperability for microwave access (WiMAX), and/or other air interface protocol radio transceiver cards, and other well-known network devices. These network connectivity devices 792 may enable the processor 782 to communicate with an Internet or one or more intranets. With such a network connection, it is contemplated that the processor 782 might receive information from the network, or might output information to the network in the course of performing the above-described method steps. Such information, which is often represented as a sequence of instructions to be executed using processor 782, may be received from and outputted to the network, for example, in the form of a computer data signal embodied in a carrier wave.

Such information, which may include data or instructions to be executed using processor 782 for example, may be received from and outputted to the network, for example, in the form of a computer data baseband signal or signal embodied in a carrier wave. The baseband signal or signal embodied in the carrier wave generated by the network connectivity devices 792 may propagate in or on the surface of electrical conductors, in coaxial cables, in waveguides, in an optical conduit, for example an optical fiber, or in the air or free space. The information contained in the baseband signal or signal embedded in the carrier wave may be ordered according to different sequences, as may be desirable for either processing or generating the information or transmitting or receiving the information. The baseband signal or signal embedded in the carrier wave, or other types of signals currently used or hereafter developed, may be generated according to several methods well known to one skilled in the art. The baseband signal and/or signal embedded in the carrier wave may be referred to in some contexts as a transitory signal.

The processor 782 executes instructions, codes, computer programs, scripts which it accesses from hard disk, floppy disk, optical disk (these various disk based systems may all be considered secondary storage 784), ROM 786, RAM 788, or the network connectivity devices 792. While only one processor 782 is shown, multiple processors may be present. Thus, while instructions may be discussed as executed by a processor, the instructions may be executed simultaneously, serially, or otherwise executed by one or multiple processors. Instructions, codes, computer programs, scripts, and/or data that may be accessed from the secondary storage 784, for example, hard drives, floppy disks, optical disks, and/or other device, the ROM 786, and/or the RAM 788 may be referred to in some contexts as non-transitory instructions and/or non-transitory information.

In an embodiment, the computer system 780 may comprise two or more computers in communication with each other that collaborate to perform a task. For example, but not by way of limitation, an application may be partitioned in such a way as to permit concurrent and/or parallel processing of the instructions of the application. Alternatively, the data processed by the application may be partitioned in such a way as to permit concurrent and/or parallel processing of different portions of a data set by the two or more computers. In an embodiment, virtualization software may be employed by the computer system 780 to provide the functionality of a number of servers that is not directly bound to the number of computers in the computer system 780. For example, virtualization software may provide twenty virtual servers on four physical computers. In an embodiment, the functionality disclosed above may be provided by executing the application and/or applications in a cloud computing environment. Cloud computing may comprise providing computing services via a network connection using dynamically scalable computing resources. Cloud computing may be supported, at least in part, by virtualization software. A cloud computing environment may be established by an enterprise and/or may be hired on an as-needed basis from a third party provider. Some cloud computing environments may comprise cloud computing resources owned and operated by the enterprise as well as cloud computing resources hired and/or leased from a third party provider.

In an embodiment, some or all of the functionality disclosed above may be provided as a computer program product. The computer program product may comprise one or more computer readable storage medium having computer usable program code embodied therein to implement the functionality disclosed above. The computer program product may comprise data structures, executable instructions, and other computer usable program code. The computer program product may be embodied in removable computer storage media and/or non-removable computer storage media. The removable computer readable storage medium may comprise, without limitation, a paper tape, a magnetic tape, magnetic disk, an optical disk, a solid state memory chip, for example analog magnetic tape, compact disk read only memory (CD-ROM) disks, floppy disks, jump drives, digital cards, multimedia cards, and others. The computer program product may be suitable for loading, by the computer system 780, at least portions of the contents of the computer program product to the secondary storage 784, to the ROM 786, to the RAM 788, and/or to other non-volatile memory and volatile memory of the computer system 780. The processor 782 may process the executable instructions and/or data structures in part by directly accessing the computer program product, for example by reading from a CD-ROM disk inserted into a disk drive peripheral of the computer system 780. Alternatively, the processor 782 may process the executable instructions and/or data structures by remotely accessing the computer program product, for example by downloading the executable instructions and/or data structures from a remote server through the network connectivity devices 792. The computer program product may comprise instructions that promote the loading and/or copying of data, data structures, files, and/or executable instructions to the secondary storage 784, to the ROM 786, to the RAM 788, and/or to other non-volatile memory and volatile memory of the computer system 780.

In some contexts, a baseband signal and/or a signal embodied in a carrier wave may be referred to as a transitory signal. In some contexts, the secondary storage 784, the ROM 786, and the RAM 788 may be referred to as a non-transitory computer readable medium or a computer readable storage media. A dynamic RAM embodiment of the RAM 788, likewise, may be referred to as a non-transitory computer readable medium in that while the dynamic RAM receives electrical power and is operated in accordance with its design, for example during a period of time during which the computer 780 is turned on and operational, the dynamic RAM stores information that is written to it. Similarly, the processor 782 may comprise an internal RAM, an internal ROM, a cache memory, and/or other internal non-transitory storage blocks, sections, or components that may be referred to in some contexts as non-transitory computer readable media or computer readable storage media.

In an embodiment, adsorbent materials are disposed within or contained by the columns of apparatus 300. Adsorbent materials suitable for use in the present disclosure include chromatographic materials which have been subjected to a sanitization process. In an embodiment, the adsorbent materials are selected from the group consisting of synthetic carbon, anion exchange resins, cation-exchange resins, and combinations thereof.

In an embodiment, the adsorbent material comprises a synthetic carbon particle (SCP) containing micro-, meso- and macropores from porous phenolic resins. As used herein, the term "micropore" refers to a pores with diameter <2 nm, as measured by nitrogen adsorption and mercury porosimetry methods and as defined by IUPAC. As used herein, the term "mesopore" refers to pores with diameter from ca. 2 nm to ca. 50 nm, as measured by nitrogen adsorption and mercury porosimetry methods and as defined by IUPAC. As used herein, the term "macropore" refers to pores with diameters larger than 50 nm, as measured by nitrogen adsorption and mercury porosimetry methods and as defined by IUPAC. In relation to this invention there are two types of macropores. In macroporous beads they are located within beads and formed by pore-formers. Their size is 50-500 nm, typically 70-200 nm. These macropores are very effective in adsorption of cytokines. Typically a precursor resin formulation is used which comprises a large proportion of pore former, e.g. 250 parts ethylene glycol or other pore former to 100 parts of resin-forming components Herein a mesoporous resin may be formed by condensing a nucleophilic component which comprises a phenolic compound or a phenol condensation prepolymer with at least one electrophilic cross-linking agent selected from formaldehyde, paraformaldehyde, furfural and hexamethylene tetramine in the presence of a pore-former selected from the group consisting of a diol (e.g. ethylene glycol), a diol ether, a cyclic ester, a substituted cyclic ester, a substituted linear amide, a substituted cyclic amide, an amino alcohol and a mixture of any of the above with water to form a resin. The pore-former is present in an amount effective to impart meso- or macroporosity to the resin (e.g. at least 120 parts by weight of the pore former being used to dissolve 100 parts by weight of the total resin forming components, i.e. nucleophilic component plus electrophilic component), and it is removed from the porous resin after condensation by cascade washing with water or by vacuum drying. The resulting resin may be carbonised by heating in an inert atmosphere to a temperature of at least 600° C. to give a material having a bimodal distribution of pores, the pore structure as estimated by nitrogen adsorption porosimetry comprising micropores and mesopores or macropores. The value for the differential of pore volume with respect to the logarithm of pore radius (dV/d log R) for the mesopores is greater than 0.2 for at least some values of pore size in the range 20-500 Å. The mesoporous carbon may have a BET surface area of 250-800 $m^2/g$ without activation. It may be activated by heating it at high temperature in the presence of carbon dioxide, steam or a mixture thereof, e.g. by heating it in carbon dioxide at above 800° C., or it may be activated by heating it in air at above 400° C. It may then have surface areas of up to 2000 $m^2/g$ and even higher e.g. 1000-2000 $m^2/g$. As used herein the term "BET surface area" is determined by the Brunauer, Emmett, and Teller (BET) method according to ASTM D1993-91, see also ASTM D6556-04.

Resins for making carbonaceous material can be prepared from any of the starting materials such that the nucleophilic components may comprise phenol, bisphenol A, alkyl phenols e.g. cresol, diphenols e.g. resorcinol and hydroquinione and aminophenols e.g. m-amino-phenol.

It is preferred to use as nucleophilic component a phenolic novolac or other similar oligomeric starting material which because it is already partly polymerized makes polymerization to the desired resin a less exothermic and hence more controllable reaction. The preferred novolacs have average molecular weights (AMW) in the range of from 300 to 3000 prior to cross-linking (corresponding to a DP with respect to phenol of about 3-30). Where novolac resins are used, they may be solids with melting points in the region of 100° C. Novolac resins of AMW less than 2000 and preferably less than 1500 form resins which on carbonisation tend to produce carbons with desired pore size distributions using lower amounts of pore former. Novolacs are thermally stable in that they can be heated so that they become molten and cooled so that they solidify repeatedly without structural change. They are cured on addition of cross-linking agents and heating. Fully cured resins are infusible and insoluble. Whilst commercial novolacs are largely produced using phenol and formaldehyde, a variety of modifying reagents can be used at the pre-polymer formation stage to introduce a range of different oxygen and nitrogen functionalities and cross-linking sites. These include but are not limited to: (a) Dihydric phenols e.g. resorcinol and hydroquinone. Both are more reactive than phenol and can lead to some cross-linking at the pre-polymer production stage. It is also possible to introduce these compounds at the cross-linking stage to provide different cross-linking paths. These also increase the oxygen functionality of the resins. (b) Nitrogen containing compounds that are active in polycondensation reactions, such as urea, aromatic (aniline, m-amino phenol) and heteroaromatic (melamine) amines. These allow the introduction of specific types of nitrogen functionality into the initial polymer and final carbon and influence the development of the mesoporous structure of both the resins and the final carbons. Like hydroquinone and resorcinol, all the nitrogen containing nucleophilic modifying reagents which can be used possess two or more active sites and are more reactive in condensation reactions than phenol or novolacs. It means that they are first to react with primary cross-linking agents forming secondary cross-linking agents in situ.

The nucleophilic component may be provided alone or in association with a polymerization catalyst which may be a weak organic acid miscible with the novolac and/or soluble in the pore former e.g. salicylic acid, oxalic acid or phthalic acid. The concentration of novolac in the pore former may be such that when combined with the solution of cross-linking agent in the same pore former the overall weight ratio of pore former to (novolac+cross-linking agent) is at least 125:100 by weight. The actual ratios of novolac:pore former and cross-linking agent:pore former are set according to convenience in operation by the operational requirements of a bead production plant and are controlled by the viscosity of the novolac:pore former solution such that it remains pumpable and by the ratio of cross-linking agent:pore former such that the cross-linking agent remains in solution throughout the plant.

The cross-linking agent is normally used in an amount of from 5 to 40 parts by weight (pbw) per 100 parts by weight of the nucleophilic components e.g. novolac. It may be, for example, an aldehyde e.g. formaldehyde or furfural, it could be hexamethylenetetramine (hexamine), or hydroxymethylated melamine.

Hexamine is preferably used as cross-linking agent. In embodiments requiring a completely cured resin, it is preferably used for cross-linking novolac resin at a proportion of 10 to 25 pbw e.g. about 15 to 20 pbw hexamine per 100 pbw of novolac. This ensures formation of the solid resin with maximal cross-linking degree and ensures the stability of the mesopore structure during subsequent removal of the pore former.

The pore former also acts as solvent. Thus, the pore former is preferably used in sufficient quantities to dissolve the components of the resin system, the weight ratio of pore former to the total components of the resin system resin being preferably at least 1.25:1.

The pore former may be, for example, a diol, a diol-ether, a cyclic ester, a substituted cyclic or linear amide or an amino alcohol e.g. ethylene glycol, 1,4-butylene glycol, diethylene glycol, triethylene glycol, γ-butyrolactone, propylene carbonate, dimethylformamide, N-methyl-2-pyrrolidinone and monoethanolamine, ethylene glycol being preferred, and where the selection is also limited by the thermal properties of the solvent as it should not boil or have an excessive vapour pressure at the temperatures used in the curing process.

It is thought that the mechanism of meso- and macropore generation is due to a phase separation process that occurs during the cross-linking reaction. In the absence of a pore former, as the linear chains of pre-polymer undergo cross-linking, their molecular weight initially increases. Residual low molecular weight components become insoluble in the higher molecular weight regions causing a phase separation into cross-linked high molecular weight domains within the lower molecular weight continuous phase. Further condensation of light components to the outside of the growing domains occurs until the cross-linked phase becomes essentially continuous with residual lighter pre-polymer trapped between the domains. In the presence of a low level of pore former the pore former is compatible with, and remains within, the cross-linked resin domains, (e.g., <120 parts/100 parts Novolac for the Novolac-Hexamine-Ethylene Glycol reaction system), whilst the remainder forms a solution with the partially cross-linked polymer between the domains. In the presence of higher levels of pore former, which exceed the capacity of the cross-linked resin, the pore former adds to the light polymer fraction increasing the volume of material in the voids between the domains that gives rise to the mesoporosity and/or macroporosity. In general, the higher the pore former content, the wider the mesopores, up to macropores, and the higher the pore volume.

This phase separation mechanism provides a variety of ways of controlling the pore development in the cross-linked resin structures. These include chemical composition and concentration of the pore former; chemical composition and quantity of the cross-linking electrophilic agents, presence, chemical nature and concentration of modifying nucleophilic agents, chemical composition of phenolic nucleophilic components (phenol, novolac), the presence of water within the solvent and concentration of any curing catalyst if present.

An SCP suitable for use in the present disclosure may have any shape compatible with the compositions and methodologies disclosed herein. For example the shape of the SCP may be that of an irregular granule, a low angularity shape, spherical (e.g., bead), pellet, minilith, monolith, etc. . . . . For simplicity, the present disclosure may refer to the use of beads of the SCB however it is to be understood the SCP may be of any suitable shape.

Production of the bead form may be by pouring a solution of a partially cross-linked pre-polymer into a hot liquid such as mineral oil containing a dispersing agent and stirring the mixture. The pre-polymer solution forms into beads which are initially liquid and then, as curing proceeds, become solid. The average bead particle size is controlled by several process parameters including the stirrer type and speed, the oil temperature and viscosity, the pre-polymer solution viscosity and volume ratio of the solution to the oil and the mean size can be adjusted between 5 and 2000 μm although in practice the larger bead sizes are difficult to achieve owing to problems with the beads in the stirred dispersion vessel. The beads can then be filtered off from the oil. In a preparative example, industrial novolac resin is mixed with ethylene glycol at an elevated temperature, mixed with hexamine and heated to give a viscous solution which is poured into mineral oil containing a drying oil, after which the mixture is further heated to effect curing. On completion of curing, the reaction mixture is cooled, after which the resulting porous resin is filtered off, and washed with hot water to remove pore former and a small amount of low molecular weight polymer. The cured beads are carbonized to porous carbon beads which have a pore structure as indicated above, and may be activated as indicated above. It is stated that the beads can be produced with a narrow particle size distribution e.g. with a D90/D10 of better than 10 and preferably better than 5. However, the bead size distribution that can be achieved in practice in stirred tank reactors is relatively wide, and the more the process is scaled up the worse the homogeneity of the mixing regime and hence the particle size distribution becomes wider.

Discrete solid beads of polymeric material e.g. phenolic resin having a porous structure may be formed, which process may produce resin beads on an industrial scale without aggregates of resin building up speedily and interrupting production. The process comprises the steps of: (a) combining a stream of a polymerizable liquid precursor e.g. a novolac and hexamine as cross-linking agent dissolved in a first polar organic liquid e.g. ethylene glycol with a stream of a liquid suspension medium which is a second non-polar organic liquid with which the liquid precursor is substantially or completely immiscible e.g. transformer oil containing a drying oil; (b) mixing the combined stream to disperse the polymerizable liquid precursor as droplets in the suspension medium e.g. using an in-line static mixer; (c) allowing the droplets to polymerise in a laminar flow of the suspension medium so as to form discrete solid beads that cannot agglomerate; and (d) recovering the beads from the suspension medium.

For bead production, the pore former comprises a polar organic liquid e.g. ethylene glycol chosen in combination with dispersion medium which is a non-polar organic liquid so as to form a mainly or wholly immiscible combination, the greater the incompatibility between the pore former which forms the dispersed phase and the dispersion medium, the less pore former becomes extracted into the dispersion medium. The pore former desirably has a greater density than the dispersion medium with which it is intended to be used so that droplets of the pore former containing dissolved resin-forming components will pass down a column more rapidly than a descending flow of dispersion medium therein. Both protic and aprotic solvents of different classes of organic compounds match these requirements and can be used as pore formers, both individually and in mixtures. In addition to dissolving the reactive components and any catalyst, the pore former should also, in the case of phenolic resins, be compatible with water and/or other minor condensation products (e.g. ammonia) which are formed by elimination as polymerization proceeds, and the pore former is preferably highly miscible with water so that it can be readily removed from the polymerized resin beads by washing.

The dispersion medium is a liquid which can be heated to the temperature at which curing is carried out e.g. to 160° C. without boiling at ambient pressure and without decomposition and which is immiscible with ethylene glycol and with the dissolved components therein. It may be hydrocarbon-based transformer oil which is a refined mineral oil and is a by-product of the distillation of petroleum. It may be composed principally of $C_{15}$-$C_{40}$ alkanes and cycloalkanes, have a density of 0.8-0.9 depending upon grade and have a boiling point at ambient pressure of 260-330° C., also depending upon grade. Transformer oil has a viscosity of about 0.5 poise at 150° C. which is a typical cure temperature. Transformer oil or other dispersion medium may be used in volumes 3-10 times the volume of the combined streams of nucleophilic precursor and crosslinking agent e.g. about 5 times.

Preferred dispersing agents which are dissolved in the dispersion medium before that medium is contacted with the reaction mixture to be dispersed therein to retard droplet coalescence are either sold as drying oils e.g. Danish oil or are produced by partially oxidizing naturally occurring precursors such as tung oil, linseed oil etc. The dispersing agents are consumed as the process proceeds, so that if the dispersion medium is recycled, dispersing agent in the recycled oil stream should be replenished. The dispersing agent is conveniently supplied as a stream in solution in the dispersion medium e.g. transformer oil and e.g. in an amount of 5-10% v/v where Danish oil is used which contains a low concentration of the active component to give final concentration of the dispersant in the dispersion medium 0.2-1% v/v. Higher dispersant concentrations would be used in the case of oxidised vegetable oils.

The resin beads formed as described above may be carbonised and optionally activated. For example, carbonization and activation may comprise supplying the material to an externally fired rotary kiln maintained at carbonizing and activating temperatures, the kiln having a downward slope to progress the material as it rotates, the kiln having an atmosphere substantially free of oxygen provided by a counter-current of steam or carbon dioxide, and annular weirs being provided at intervals along the kiln to control progress of the material. In an embodiment, a SCP suitable for use in the present disclosure is characterized by a microporous/macroporous structure. In an embodiment, the SCP has a macroporous pore size of from about 75 μm to about 1000 μm, alternatively the SCP has a macroporous size of from about 100 μm to about 750 μm, or alternatively from about 100 μm to about 500 μm. Herein an SCP suitable for use in the present disclosure may comprise an SCP having at least two pore size distributions such that the SCP is a mixture of carbon beads having at least two distributions of macroporous pore sizes. In an embodiment, the SCP may comprise a first population having a macroporous pore size denoted x and a second population having a macroporous pore size y where the SCP provides a mixture having a ratio of x/y of about 1; alternatively about 5, alternatively about 10, alternatively about 20; alternatively about 50, or alternatively about 100. In some embodiments, the SCP comprises a mixture of two populations wherein the pore size of the first population is approximately twice the pore size of the second population. In some embodiments, the SCP comprises a mixture of three populations where the pore size of a first population is approximately twice the pore size of the second population and the pore size of the third population is approximately two and a half times the pore size of the second population.

In an embodiment, the adsorbent material comprises an ion exchange resin (IER). Herein an IER refers to an insoluble matrix fabricated from a substrate and functionalized with a fixed ion and a mobile counterion. The IER retards ions on the surface of the material with the concomitant release of the mobile counterion. IERs can also be described as insoluble polymers that contain ionizable groups distributed regularly along the polymer backbone. As a consequence, any counter ion associated with the ion exchange resin is ionically bound to the ion exchange resin and physically separated from the surrounding fluid.

In an embodiment, an IER suitable for use in the present disclosure has a bead size ranging from about 40 μm to about 1000 μm, alternatively from about 40 μm to about 750 μm, or alternatively from about 100 μm to about 500 μm.

In an embodiment, the IER is an anion exchange resin. Herein "anion exchange resin" refers to an ion exchange resin with covalently bound positively charged groups, such as quaternary amino groups and mobile negatively charged groups. The term "anion exchange resin" is intended to encompass strong base anion exchange resins (SBA), weak base anion exchange resins (WBA) and related anionic functional resins, of either the gellular or macroporous type containing quaternary ammonium functionality (chloride, hydroxide or carbonate forms), dialkylamino or substituted dialkylamino functionality (free base or acid salt form), and aminoalkylphosphonate or iminodiacetate functionality, respectively. Examples of commercially available anion exchange resins suitable for use in the present disclosure include without limitation those sold under the tradename of DEAE, QAE, and UNOSphere. In an embodiment, the anion exchange resin comprises UNOSphere Q Media.

In an embodiment, the IER is a cation exchange resin. The cation exchange resin of the present disclosure may be strongly or weekly acidic and have a variety of functional groups, e.g., weakly acidic type of resin containing carboxylic acid group, or strongly acidic type of resin containing sulfonic functional groups. Generally, the carboxylic functional groups may be derived from polymers or copolymers of methacrylic acid or polymethacrylic acid and the sulfonic functional groups may generally be derived from polymers or copolymers of styrene and divinylbenzene. Other polymeric matrices, organic ion exchange matrices or inorganic ion exchange matrices may be used as suitable ion exchange resins, e.g., methacrylic, acrylic and phenol formaldehyde. For example, cation exchange resins suitable for use in the present disclosure include without limitation AMBERLITE and UNOSphere S Media. AMBERLITE 15 described by the manufacturer as gel-type divinylbenzene sulfonic acid cation exchange resin that swells in water.

In an embodiment, an adsorbent material suitable for use in the present disclosure has been subjected to a sanitization process. Herein the sanitization process refers to a method of treating the adsorbent materials in order to (i) remove pathogens; (ii) reduce the amount of fine particulates and leachables; (iii) reduce the amount of trapped air and (iv) sterilize the materials. Adsorbent materials that have been subjected to the sanitization process disclosed herein are considered to have been converted from an industrial grade material to a pharmaceutical grade material with a concomitant increase in hemocompatability.

In an embodiment, a method for sanitization of a SCP of the type disclosed herein comprises a dry heat treatment to produce a heat-treated SCP. Dry heat treatment of the SCP may be carried out at a temperature at equal to or greater than about 180° C. for a time period equal to or greater than about 4 hours, alternatively at a temperature of equal to or greater than about 200° C. for a time period of equal to or greater than about 1 hour, or alternatively at a temperature of 250° C. for a time period of equal to or greater than about 30 min. Dry heat treatment of the SCP may function to reduce the bioburden of the material and particularly the amount of pathogenic (e.g., bacteria, viruses, fungi, etc. . . . ) and pyrogenic (e.g., endotoxin) substances associated with the SCP. For example, the total amount of pathogenic substances associated with the heat-treated SCP may be reduced by greater than about 50%, alternatively greater than about 90%, alternatively greater than about 91%, alternatively greater than about 92%, alternatively greater than about 93%, alternatively greater than about 94%, alternatively greater than about 95%, alternatively greater than about 96%, alternatively greater than about 97%, alternatively greater than about 98%, alternatively greater than about 99%, or alternatively about 100% when compared to the SCP.

In an embodiment, the bioburden of the SCP is reduced by about 100% through the use of a dry heat treatment. Alternatively, the bioburden of the SCP is reduced through the use of any suitable methodology compatible with the SCP and the other components of the present disclosure. In some embodiments, the bioburden of the SCP is reduced by 100% utilizing methodologies consistent with jurisdictional guidelines for the sanitization of materials that will contact mammalian blood and produce a product that will be subsequently utilized in mammals.

In an embodiment, a method for sanitization further comprises the removal of fine particulates and leachables from the heat-treated SCP. Herein particulates smaller than about 30 microns are referred to as "fines" while "leachables" describe the organic compounds that can be eluted from the adsorbent material (e.g., heat-treated SCP) in the presence/absence of an applied sample. In an embodiment, removal of the fine particulates and leachables from the heat-treated SCP comprises contacting the heat-treated SCP with water, removing water from the heat-treated SCP to produce a washed SCP, contacting the washed SCP with a salt solution to produce a modified SCP and removing the salt solution from the modified SCP to produce a processed SCP. The heat-treated SCP may be contacted with from about 4 volumes to about 10 volumes of water, alternatively from about 5 volumes to about 10 volumes of water or alternatively from about 6 volumes to about 8 volumes of water. Contacting of the adsorbent material with a substance may be carried out in any suitable vessel. For example, the adsorbent material (e.g., heat-treated SCP) may be positioned within a cartridge or column to facilitate contacting of the adsorbent material with one or more substances of the type disclosed herein. For example, the washed SCP may be contacted with a salt solution comprising a sodium chloride salt at a concentration of 3 g/dL. The washed SCP may be contacted with from about 4 volumes to about 10 volumes of salt solution based on the total volume of the SCP, alternatively from about 6 volumes to about 10 volumes of salt solution or alternatively from about 6 volumes to about 8 volumes of salt solution. It is contemplated that other salt solutions providing similar pH and osmolarity, such as known to the ordinarily skilled artisan and compatible with the other methods and compositions of the present disclosure, may be employed to facilitate the removal of fine particulates and leachables from the SCP.

For either the removal of water to produce a washed SCP or the removal of salt to produce a processed SCP, the removal may be effected using any suitable methodology. For example, the removal of fine particulates and leachables may be carried out by placing the adsorbent material in a column which may be allowed to drain under gravity until no further eluent is detected in order to remove the water and/or salt solution. In some embodiments, the adsorbent material may be subjected to a plurality of processes for the removal of fine particulates and leachables. Further, in some embodiments, the solution produced by contacting the adsorbent material with water and/or a salt solution may be analyzed to determine the amount of fine particulates and/or leachables removed following contact. Such determinations may be made and the process for removal of fine particulates and/or leachables repeated until some user and/or process desired level of fine particulates and/or leachables is achieved.

In an embodiment, a method for sanitization further comprises dewatering the processed SCP. Water present with the adsorbent material has the tendency to separate from the material resulting in compaction and a reduction in flow properties. De-watering is the process of removing extraneous fluid (typically water or aqueous solutions) from wet or slurried particles without removing fluid in the particles (i.e., prevent evaporative drying of the particles). Herein "extraneous" means any fluid outside the particles. Therefore any fluid absorbed into the polymer matrix or present in the pores is not considered extraneous.

Any suitable methodology may be employed for the dewatering of the processed SCP. Examples of methodologies suitable for use in dewatering the processed SCP include without limitation the passage of moist air through the particles. The resultant material is referred to as the dewatered SCP. In an embodiment, dewatering of the processed SCP is carried out using a dewatering apparatus.

In an embodiment, a method for sanitization further comprises aseptic processing of the dewatered SCP, also referred to as sterile fill and sterilization to produce a sanitized SCP. Sterility may be achieved using any suitable methodology. For example sterile processing may include the use of clean rooms, bacteria retaining filters, and dry or steam heat. In an embodiment, aseptic processing of the dewatered SCP comprises terminal sterilization by autoclaving (e.g., at 121° C., 15 psi for 30 min), gas sterilization, e-beam sterilization, gamma radiation, or combinations thereof.

In an embodiment, the adsorbent material is an IER (e.g., anion exchange resin) and a method for sanitization of an IER comprises the removal of fine particulates. Removal of the fine particulates from the IER may comprise contacting the IER with water, removing water from the IER to produce a washed IER, contacting the washed IER with a salt solution to produce a modified IER and removing the salt solution from the modified IER to produce a processed IER. The IER may be contacted with from about 4 volumes to about 10 volumes of water based on the total volume of the IER, alternatively from about 6 volumes to about 10 volumes of water or alternatively from about 6 volumes to about 8 volumes of water. Contacting of the adsorbent material with a substance may be carried out in any suitable vessel. For example, the adsorbent material (e.g., IER) may be positioned within a cartridge or column to facilitate contacting of the adsorbent material with one or more substances of the type disclosed herein. In an embodiment, the washed IER is contacted with a salt solution comprising for example 0.9% NaCl in water. It is contemplated that other salt solutions, such as known to the ordinarily skilled artisan providing similar pH and osmolarity, and compatible with the other methods and compositions of the present disclosure, may be employed to facilitate the removal of fine particulates and leachables from the IER. The washed IER may be contacted with from about 2 volumes to about 8 volumes of salt solution based on the total volume of IER, alternatively from about 4 volumes to about 8 volumes of salt solution or alternatively from about 6 volumes to about 8 volumes of salt solution. For either the removal of water to produce a washed IER or the removal of salt to produce a processed IER, the removal may be effected using any suitable methodology. For example, the removal of fine particulates may be carried out by placing the adsorbent material in a column which may be allowed to drain under gravity until no further eluent is detected in order to remove the water and/or salt solution. In some embodiments, the adsorbent material may be subjected to a plurality of processes for the removal of fine particulates. Further, in some embodiments, the solution produced by contacting the adsorbent material with water and/or a salt solution may be analyzed to determine the amount of fine particulates. Such determinations may be made and the process for removal of fine particulates repeated until some user and/or process desired level of fine particulates is achieved.

In an embodiment, a method for sanitization further comprises autoclaving the processed IER. Autoclaving of the processed IER may be carried out at a temperature of equal to or greater than about 121° C. for a period of time equal to or greater than about 30 min, alternatively equal to or greater than about 60 min, or alternatively for a period of time from about 30 min to about 60 min. The resultant material is termed an autoclaved IER.

The autoclaved IER may be further processed by undergoing a high pH treatment. For example, the autoclaved IER may be contacted with a 1M to 2M NaOH solution for a period of time equal to or less than about 24 hours. It is contemplated that other basic solutions providing the pH characteristics of a 1M to 2M NaOH solution and compatible with the other aspects of this disclosure may be employed for high pH treatment of the IER. The resultant material is termed a pH-treated IER. Autoclaving of the processed IER may function to reduce the bioburden of the material and particularly the amount of pathogenic (e.g., bacteria, viruses, fungi, etc. . . . ) and pyrogenic (e.g., endotoxin) substances associated with the processed IER. For example, the total amount of pathogenic substances associated with the autoclaved IER may be reduced by greater than about 50%, alternatively greater than about 90%, alternatively greater than about 91%, alternatively greater than about 92%, alternatively greater than about 93%, alternatively greater than about 94%, alternatively greater than about 95%, alternatively greater than about 96%, alternatively greater than about 97%, alternatively greater than about 98%, alternatively greater than about 99%, or alternatively about 100% when compared to the IER. In an embodiment, the bioburden of the IER is reduced by about 100% through the use of methodologies disclosed herein. Alternatively, the bioburden of the IER is reduced by about 100% through the use of any suitable methodology compatible with the IER and the other components of the present disclosure. In some embodiments, the bioburden of the IER is reduced by 100% utilizing methodologies consistent with jurisdictional guidelines for the sanitization of materials that will contact mammalian blood and produce a product that will be subsequently utilized in mammals.

In an embodiment, a method for sanitization further comprises the chromatographic removal of base and leachables from the pH-treated IER. For example, the IER may be disposed within a column and contacted with sufficient volumes of a low concentration salt solution to provide an eluent having a neutral pH. In an embodiment the IER may be washed with a 3% NaCl solution until the eluent has a pH ranging from about 7.4 to about 7.6. It is contemplated that other salt solutions, such as known to the ordinarily skilled artisan and compatible with the other methods and compositions of the present disclosure, may be employed to facilitate the removal of bases and leachables from the IER. The resultant material is termed a modified IER.

In an embodiment, a method for sanitization further comprises dewatering the modified IER to produce a dewatered IER. Herein dewatering refers to the removal of water from the adsorbent materials. Water present with the adsorbent material has the tendency to separate from the material resulting in compaction and a reduction in flow properties. Any suitable methodology may be employed for the dewatering of the IER. Examples of methodologies suitable for use in dewatering the IER are described herein with regards to dewatering of the SCP.

In an embodiment, a method for sanitization further comprises aseptic processing of the dewatered IER, also referred to as sterile fill and sterilization to produce a sanitized IER. Sterility may be achieved using any suitable methodology. For example sterile processing may include the use of clean rooms, bacteria retaining filters, dry or steam heat, terminal sterilization by autoclaving at 121° C., 15 psi for 30 min, gas sterilization, e-beam sterilization, gamma radiation, or combinations thereof. In some embodiments, methods for sanitization of the SCP, IER, or both do not comprise or alternatively exclude aseptic processing.

The sanitization process disclosed herein may be performed using any suitable equipment and/or having the adsorbent material disposed within any suitable vessel for performing one or more steps of the sanitization process. In an embodiment, the adsorbent material is disposed within a column and the sanitization process is carried out without transfer of the adsorbent material to another container or vessel. In such embodiments, the adsorbent material is subjected to sanitization-in-place (SIP).

In an embodiment, adsorbent materials subjected to a sanitization process, both of the type disclosed herein, are characterized by a bioburden maximum of 20 endotoxin units (EU) as determined using any suitable methodology such as the Limulus amebocyte lysate test. In an embodiment, adsorbent materials subjected to a sanitization process, both of the type disclosed herein, are characterized as fine particulates free which are defined herein as having less than about 1% fine particulates as determined by laser diffraction. Methodologies of the type disclosed herein may result in in adsorbent materials having less than about 0.5%, 0.1% or undetectable amounts of fine particulates. In an embodiment, adsorbent materials subjected to a sanitization process, both of the type disclosed herein, are characterized as leachables free which are defined herein as having less than about 1% leachables as determined spectrophotometrically in the wavelength range of 205 nm to 340 nm. Methodologies of the type disclosed herein may result in adsorbent materials having less than about 0.5%, 0.1% or undetectable amounts of leachables. Such materials are collectively referred to herein as sanitized adsorbent materials (SAM).

In an embodiment, the SAM is sanitized in accordance with the United States Food and Drug Administration Code of Federal Regulations Title 21, e.g., section 876.5870 for the regulation of Sorbent and Hemoperfusion systems.

In an embodiment, SAMs suitable for use in the present disclosure (e.g., in the columns of apparatus 300) are further subjected to contact with a compatibilizer which functions to coat at least a portion of the surface area of the SAM. Herein a compatibilizer refers to a substance that functions to increase the biocompatibility of the SAM with biological fluids and may aid in decreasing the binding of non-target molecules to the SAM. In an embodiment, the compatibilizer comprises a polysaccharide, a glucan, albumin, mannitol, a starch, or combinations thereof.

In an embodiment, the compatibilizer comprises dextran. Dextrans, representations are depicted in Formula 1, are polysaccharides having a linear backbone of α-linked D-glucopyranosyl repeating units. In an embodiment, a dextran suitable for use in the present disclosure has an average molecular weight ranging from about 1 kDa to about 500 kDa, alternatively from about 1 kDa to about 70 kDa, alternatively from about 1 kDa to about 40 kDa, or alternatively from about 40 kDa to about 70 kDa. Nonlimiting examples of compatibilizers suitable for use in the present disclosure include DEXTRAN-1, DEXTRAN-40 and DEXTRAN-70 commercially available from Hospira Inc.

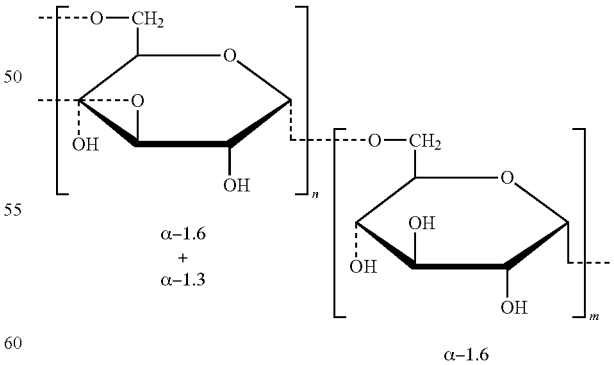

Formula I

In an embodiment, the compatibilizer comprises hydroxyethyl starch. Hydroxyethyl starch, depicted in Formula II, is a nonionic starch derivative that is commonly used as a volume expander in a type of intravenous therapy that has the function of providing volume for the circulatory system.

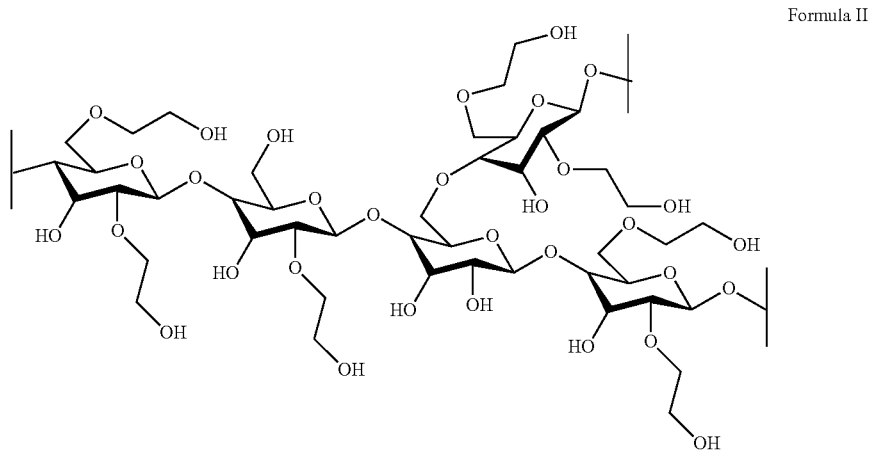

Formula II

In an embodiment the compatiblizer comprises a mixture of albumin and mannitol. Serum albumin is the main protein of human blood plasma whose primary function is to regulate the colloidal osmotic pressure of blood. Mannitol, (2R,3R,4R,5R)-Hexan-1,2,3,4,5,6-hexol, is a sugar alcohol, which can function an Osmotic Diuretic. The weight ratio of albumin to mannitol in the compatibilizer may range from 20:1 to 1:1, alternatively from 18:1 to 1:1, or alternatively from 15:1 to 10:1.

Without wishing to be limited by theory, the compatibilizer (e.g., dextran) may function to prime the extracorporeal circuit (i.e., apparatus having columns containing the adsorbent materials) and may lessen complications by blocking the initial exposure of blood components and plasma to foreign surfaces while maintaining a higher level of colloid oncotic pressure. In an embodiment, the compatibilizer is dextran 40 which may function in (i) preventing shear-induced fines formation via lubrication effect; (ii) serving as a priming agent for the extracorporeal circuit assembled with the blood separator and the adsorbing device to prevent activation of plasma and other blood components following early primary exposure; and (iii) modulating sorbing capacity of porous sorbents such as synthetic mesoporous/microporous carbon. For example, the adsorbents packed into columns as components of an apparatus of the type disclosed herein, during storage/distribution can be exposed to relatively high shear stresses which can be a continuous source of particulates dextran may prevent fines formation by lubrication at any shear condition.

SAMs suitable for use in the present disclosure may be contacted with the compatibilizer using any suitable methodology. In an embodiment, the compatibilizer is dextran which may be formulated as a solution suitable for use in the present disclosure having from about 1 weight percent (wt. %) dextran about 10 wt. % dextran, alternatively from about 2 wt. % to about 9 wt. % or alternatively from about 3 wt. % to about 7 wt. %. In an embodiment, the compatibilizer is hydroxyethyl starch which may be formulated as a solution suitable for use in the present disclosure having from about 1 wt. % to about 6 wt. % hydroxyethyl starch, alternatively from about 1.5 wt. % to about 6 wt. % hydroxyethyl starch or alternatively from about 2 wt. % to about 6 wt. % hydroxyethyl starch. The resultant compatibilized SAM (C-SAM) may be characterized by the formation of a coating of the compatibilizer on the particles of the SAM such that the coating covers greater than about 50% of the particle's surface; alternatively, greater than about 60%, 70%, 80% or 90% of the particle's surface.

In an embodiment, C-SAMs are introduced to the columns of apparatus 300. For example, the apparatus may be operated having sanitized compatibilized SCP in column A (referring to FIG. 1, column 310), a mixture of a sanitized compatibilized SCP and a sanitized compatibilized anionic exchange resin in column B (referring to FIG. 1, column 350) and a mixture of a SCP and a cationic exchange resin in column C (referring to FIG. 1, column 370). In an embodiment, the disclosed methodology comprises an extracorporeal device of the type depicted as apparatus 300 wherein bodily fluids (e.g., blood) obtained from a subject suffering from an autoimmune, metabolic, inflammatory, degenerative or neoplastic disorder, as well as poisoning or drug overdose, are contacted with the materials housed in the depicted columns in a sequence consisting essentially of contacting with a sanitized compatibilized SCP that is disposed within a first column (e.g., column A 310) to form a first eluent that is introduced to a second column (e.g., column B 350) and contacted with a mixture of a sanitized compatibilized SCP and a sanitized compatibilized anion exchange resin to form a second eluent. The second eluent may subsequently introduced to a third column (e.g., column C 370) and contacted with a mixture of a sanitized compatibilized SCP and a sanitized compatibilized cation exchange resin to form a third eluent. In an embodiment, a method of treating a subject experiencing an autoimmune, metabolic, inflammatory, degenerative or neoplastic disorder, as well as poisoning or drug overdose, comprises administering to the subject at least a portion of the third eluent. In some embodiments, the third eluent may be further processed by the addition of one or more agents that function to ameliorate the symptoms of the medical condition.

In an embodiment, a subject suffering from a medical condition may be treated using the compositions and methodologies disclosed herein. For example, the subject may be placed in fluid communication with an extracorporeal apparatus of the type disclosed herein so as to allow bodily fluid of the subject to flow into an inlet port of the device. The extracorporeal apparatus may have columns situated in the apparatus to afford contact of the incoming bodily fluid with at least a first column having a sanitized compatibilized SCP disposed therein to produce a first eluent. The first eluent may then be introduced to a second column having a mixture of a sanitized compatibilized SCP and a sanitized compatibilized anionic resin to produce a second eluent. The second eluent may be subsequently introduced to a third column comprising a sanitized compatibilized SCP and a sanitized compatibilized cationic resin to produce a third eluent which may be returned to the subject.

In an embodiment, the medical condition is an autoimmune disease and the bodily fluid comprises plasma with blood cellular components. Autoimmune diseases that affect more than 10% of the US population and are among the top 10 common causes of death in people younger than 65. Examples of autoimmune diseases include without limitation rheumatoid arthritis, type-1 diabetes, inflammatory bowel diseases, systemic lupus erythematosus, and multiple sclerosis.

Rheumatoid Arthritis (RA) is the most common autoimmune disease, affecting 0.5% to 1% of the general population worldwide. RA affects more than 2 million Americans. Although the cause of RA remains unknown, the roles of small molecule mediators of inflammation (e.g., (i) arachidonic acid metabolites such as 8-isoprostane), (ii) autoantibodies, (iii) cytokines, chemokines and growth factors (IL-1$\beta$, IL-6, IL-8, TNF-$\alpha$, PDGF, GM-CSF, M-CSF), (iv) adhesion molecules, (v) matrix metalloproteinases (MMPs) and reactive oxygen species ($H_2O_2$) have been defined. RA can worsen over time and can cause permanent joint damage.

Diabetes Mellitus Type I is an autoimmune disease and affects 18.2 million people in the United States. Diabetes Mellitus Type I is characterized by the destruction of insulin-producing b-cells in the pancreatic islets of Langerhans, which is mediated by autoreactive T cells, macrophages and pro-inflammatory cytokines. This leads to an inability to produce sufficient insulin resulting in elevated blood glucose levels and pathological effects. The infiltrating macrophages secrete pro-inflammatory cytokines, namely: IL-1$\beta$, TNF-$\alpha$, IFN-$\gamma$, IL-2, IL-6, IL-8, nitric oxide (NO), reactive oxygen species and reactive lipids.

Inflammatory Bowel Disease (IBD) refers to two chronic diseases that cause intestinal inflammation: ulcerative colitis and Crohn's disease. The main difference between Crohn's disease and ulcerative collitis is the location and nature of the inflammatory changes. IBD is considered an autoimmune disease. It is estimated that as many as 1.4 million persons in the United States suffer from this disease. Although the exact etiology is still unknown, in recent years, the identification of established and potential IBD mediators has expanded to include: (i) eicosanoids (8-isoprostane), (ii) platelet activating factor, (iii) biogenic amines and kinins, (iv) complement-derived peptides, chemotactic peptides, cytokines (IL-1, IL-2, IL-4, IL-6, IL-12, IL-16, IL-18, TNF-$\alpha$, IFN-$\gamma$, TGF-$\beta$1), (v) neuropeptides, and (vi) reactive metabolites of oxygen and nitrogen.

Systemic Lupus Erythematosus (SLE) is a heterogeneous autoimmune disease involving most immune cells. Approximately 1.5 million people (one in 2,000) in the United States have Lupus. Studies in both experimental animal models of Lupus and patients with SLE have revealed a number of cytokine pathways that are important in the disease process. Among these are B-cell activating factor, which promotes B-cell survival and autoantibody production, interferon-alpha, which acts as an immune adjuvant, and tumor necrosis factor, which contributes to organ inflammation. Interferon IFN-$\gamma$, interleukin IL-18, IL-6 and possibly IL-1$\beta$ are increased in SLE and likewise involved in the inflammatory process. Among other factors, complement fragments (ie, C3a des Arg), reactive oxygen, nitrogen and lipid species also play a role. SLE can cause various symptoms, the most common being joint pains, skin rashes and tiredness. Problems with kidneys and other organs can occur in severe cases.

Multiple Sclerosis (MS) is a chronic degenerative autoimmune disease that affects the central nervous system. It damages the myelin sheath, the material that surrounds and protects the nerve cells, blocking messages between the brain and the body. MS is at least two to three times more common in women than in men. Multiple sclerosis affects 2.5 million people worldwide, including 400,000 Americans. The etiology of MS is multifactorial and there is evidence that an auto-immunological process is relevant for the pathogenesis. MS is associated with the parallel systemic up-regulation of proinflammatory cytokines: IFN-$\gamma$, TNF-$\alpha$ and IL-12, and down-regulation of TGF-$\beta$ and IL-10.

As will be clear to the ordinarily skilled artisan, several mechanisms are thought to be operative in the pathogenesis of autoimmune diseases, which include a vast array of organ-specific as well as systemic events. In all cases, the immunological system reacts against antigens of the body's own tissues, causing complete and irreversible loss of function of the targeted tissue or its hyperfunction. Autoimmune disease may involve a single tissue or multiple organs. An autoimmune response may be primarily T- or B-cell-mediated, or both. Activated B-cells produce autoantibodies—immunoglobulins, particularly IgG and IgM, directed against the body's own tissues and together with T cells, inflammatory cytokines that are responsible for acceleration of disease state and complicate the treatment.

A subject suffering from an autoimmune disease of the type disclosed herein may be treated using the compositions and methodologies disclosed herein. For example, the subject may be placed in fluid communication with an extracorporeal apparatus of the type disclosed herein so as to allow bodily fluid (e.g., plasma with blood components) of the subject to flow into an inlet port of the device. The extracorporeal apparatus may have columns situated in the apparatus to afford contact of the incoming bodily fluid with at least a first column having a sanitized compatibilized SCP disposed therein to produce a first eluent. The first eluent may then be introduced to a second column having a mixture of a sanitized compatibilized SCP and a sanitized compatibilized anionic resin to produce a second eluent. The second eluent may be subsequently introduced to a third column comprising a sanitized compatibilized SCP and a sanitized compatibilized cationic resin to produce a third eluent which may be returned to the subject.

In such embodiments, the columns having both a sanitized, compatibilized SCP and a sanitized, compatibilized anion-exchange resin disposed therein may have the ratio of sanitized compatibilized SCP to sanitized compatibilized anion-exchange of about 1:1, alternatively 75:1, alternatively 1:75, alternatively 1:50, alternatively 50:1, alternatively 1:25, or alternatively 25:1. In another embodiment, columns having both a sanitized compatibilized SCP and a sanitized compatibilized cation-exchange resin disposed therein may have the ratio of sanitized compatibilized SCP to sanitized compatibilized cation-exchange resin range from of about 1:1, alternatively 100:1, alternatively 1:50, alternatively 50:1.

In an embodiment, the extracorporeal apparatus may have columns situated in the apparatus to afford contact of the incoming bodily fluid with at least a first column having a mixture of a sanitized compatibilized SCP disposed therein to produce a first eluent. The sanitized compatibilized SCP may be a mixture of materials to provide a distribution of pore sizes such that the first column may have disposed therein a SCP having pore sizes x and 2x where the ratio of SCP with pore size x to the ratio of SCP with pore size 2x is from about 2:1 to about 5:1. Hereinafter this SCP is referred to as a bimodal SCP. The first eluent may then be introduced to a second column having a mixture of a sanitized compatibilized bimodal SCP and a sanitized compatibilized anionic resin to produce a second eluent. The second column may have a mixture of sanitized compatibilized bimodal SCP to sanitized compatibilized anionic resin ratio of from about 1:1 to about 5:2, alternatively about 3:2. The second eluent may be subsequently introduced to a third column comprising a sanitized compatibilized bimodal SCP and a sanitized compatibilized cationic resin to produce a third eluent which may be returned to the subject. The second column may have a ratio of sanitized compatibilized bimodal SCP to sanitized compatibilized cationic resin of from about 1:1 to about 5:1, alternatively about 4:1.

In an embodiment, the medical condition is selected from the group consisting of metabolic disorders, inflammatory diseases, degenerative diseases, neoplastic diseases, and systemic immune response (SIRS) disorders or SIRS-like disorders and the bodily fluid is plasma with blood cellular components. Herein inflammatory diseases refer to those in which the body reacts to an injurious agent by means of inflammation. Herein degenerative diseases refer to diseases where the primary abnormality is degeneration of a part of the body. Herein metabolic diseases refer to those where the primary abnormality is a disturbance in an important metabolic process in the body. Herein neoplastic disease refers to a disease where the primary abnormality is unregulated cell growth leading to the formation of various types of benign and malignant tumors. Hereinafter for simplicity, medical conditions selected from the group consisting of metabolic disorders, inflammatory diseases, degenerative diseases, neoplastic diseases and SIRS or SIRS-like disorders are collectively termed Class A disorders.

In an embodiment, the medical condition is a neoplastic disorder such as cancer. Cancer is a major public health problem in the United States and many other parts of the world. In 2013, in the United States alone, there were 1,660,290 new occurrences. Cancer is the second most common cause of mortality. The most prevalent symptom that patients with cancer experience is cancer-related fatigue, which is pervasive and affects patients' quality of life and productivity. Anemia and cachexia, contribute to fatigue, lethargy, tiredness, or lack of energy. Pro-inflammatory factors are implicated in many of the mechanisms proposed for the etiology of comorbidities seen in cancer, as well as cancer promotion and progression. Chronic inflammation can be oncogenic by various mechanisms: (i) induction of genomic instability, (ii) increasing angiogenesis, (iii) altering the genomic epigenetic state and (iv) increasing cell proliferation. Chronic inflammation also induces anemia and cachexia observed in cancer. Key molecular factors that contribute to inflammation-induced carcinogenic events are: (i) overproduction of reactive oxygen and nitrogen species (RNOS), (ii) activation of nuclear factor (NF)-kappa B, (iii) massive expression of inflammatory cytokines and chemokines, and (iv) increased cyclooxygenase-2 activity. Pro-inflammatory cytokines and growth factors expressed in excess in cancer have a negative impact on: (i) erythropoiesis, leading to anemia (TNF-$\alpha$, IL-1$\beta$, IL-13, TGF-$\beta$1), (ii) angiogenesis that facilitates tumor growth (VEGF, EGF, $\beta$FGF), (iii) tumor progression and metastasis (TNF-$\alpha$, IL-1$\beta$, IL-6, IL-8), as well as (iv) cachexia (TNF-$\alpha$, IL-6, IFN-$\gamma$) and other comorbidities.

In an embodiment, the medical condition is a metabolic disorder resulting in chronic kidney disease (CKD). CKD is defined as kidney damage or a glomerular filtration rate (GFR) below 60 and is a result of metabolic syndrome. GFR is a measure of the level of kidney function. CKD affects 20 million Americans (1 in 9 adults) and another 20 million are at increased risk. Hemodialysis does not stop progression to end-stage and patients are at high risk for developing anemia and other comorbidities. Early treatment of anemia is recommended to minimize the symptoms and improve quality of life. The treatment is difficult, since anemia in CKD is mainly not erythropoietin (EPO) deficient. In fact, CKD patients suffer from significantly higher oxidative stress and systemic inflammation. EPO and TGF-$\beta$1 levels are about 3 times those of the controls. High TGF-$\beta$1 levels prevent erythropoiesis. TNF-$\alpha$, IL-1$\beta$ and IFN-$\gamma$, which showed to be strong anti-erythropoietic agents, are also elevated. While inflammatory cytokines (TNF-$\alpha$, IL-1$\beta$, IL-6, IL-8, IFN-$\gamma$) accelerate the progression of kidney disease and its subsequent cardiovascular complications, the TGF-$\beta$ superfamily, besides CKD anemia, mediates nephrosclerosis. Other nephrotoxic molecules include uric acid, free hemoglobin, CRP, and active lipid—(i.e., 8-isoprostane), oxygen- and nitrogen-species.

In an embodiment, the medical condition is a degenerative disorder such as cardiovascular disease and the bodily fluid is plasma with blood cellular components. Cardiovascular diseases are the leading cause of death in the United States. They kill an estimated 17 million people worldwide each year. Cardiovascular diseases are a group of disorders of the heart and blood vessels and include: (i) coronary heart disease, (ii) cerebrovascular disease, (iii) peripheral arterial disease, (iv) rheumatic heart disease, (v) congenital heart disease, (vi) deep vein thrombosis and (vii) pulmonary embolism. Heart attacks and strokes are caused by a blockage that prevents blood from flowing to the heart or brain. The most common reason is atherosclerosis, formerly considered only as a bland lipid storage disease, but actually involves an ongoing inflammatory response. The mediators of cardiovascular diseases include: cholesterol, triglyceride, LDL, VLDL, ox-LDL, other biologically active lipids and pro-inflammatory mediators such as C-reactive protein (CRP) and cytokines. In the early stages, cardiovascular disease may be treated by lifestyle modifications aimed at slowing or stopping its progression. In advanced stages, surgical intervention or a non-surgical procedure may be necessary.

In an embodiment, the medical condition is a SIRS or SIRS-like disorder and the bodily fluid is plasma with blood cellular components. Very often neoplastic, renal and cardiovascular events driven by inflammatory responses can lead to the devastating and difficult to treat the Systemic Inflammatory Response Syndrome (SIRS). In fact, sepsis has a high mortality rate at approximately 25-50%. Septic shock is characterized by hypotension, defective $O_2$ binding, lactic acidemia and myocardial depression. These pathological responses are mediated by circulating endotoxin (LPS) that activates phagocytes to release TNF-$\alpha$ which in turn activates NOS converting L-arginine to NO. NO stimulates production of cGMP that lowers intracellular calcium resulting in hypotension and myocardial depression. Acute respiratory distress syndrome (ARDS), commonly observed in septic shock, results in lactic acidosis that lowers Hb oxygen affinity, thus deepening hypoxia that leads to multi organ failure (MOF). SIRS is a medical emergency. The treatment is difficult, since it involves the overproduction of inflammatory mediators as a consequence of the interaction of the immune system with endotoxin constituents in the body.

SIRS is a common complication in other medical conditions that has a high mortality rate, particularly burns. According to CDC deaths from fires and burns are the third leading cause of fatal home injury. On average in the United States, someone dies in a fire every 169 minutes, and someone is injured every 30 minutes. Fire and burn injuries represent 1% of the incidence of injuries and 2% of the total costs of injuries, or $7.5 billion each year. Burn injuries are characterized by (i) endotoxemia that results from bacterial translocation and leads to hypotension and end organ hypoperfusion, (ii) oxidative stress, (iii) SIRS, (iv) capillary leak syndrome (CLS), (v) hypoalbuminemia and (vi) immunosuppression with depressed T-cell function that results in infections. These pathological responses are mediated by circulating endotoxin that activates phagocytes to release TNF-α that in turn activates NOS converting L-arginine to NO. NO stimulates production of cGMP that lowers intracellular calcium producing hypotension and myocardial depression. Acute respiratory distress syndrome (ARDS) is also commonly observed in burns. Increased production of inflammatory cytokines (TNF-α, IL-1, IL-6, IL-8) lead to SIRS. TGF-β1, IL-10 and NO are immunosuppressive. Activated alternative pathway of complement participates in CLS. Burn is a medical emergency. The treatment of burns is a complex problem, since it involves the overproduction of inflammatory and other mediators with associated immunosuppression that complicates the treatment. *P. aeruginosa* infections are particularly opportunistic in burns.

These medical conditions can lead to the dysfunction of organs and accumulation of toxic metabolites. Hepatic encephalopathy (HE), which accompanies many disease states such as neoplastic, metabolic, traumatic, infectious, and toxicosis, is a condition with significant morbidity and mortality. HE is caused by an accumulation of circulating toxins that are damaging to CNS, particularly ammonia ($NH_3$), marcaptans and phenol, normally removed by the liver. Chronic liver failure and pancreatic patients also suffer from bilirubinemia resulting in jaundice and at higher levels is neurotoxic.

In an embodiment, the medical condition is the ingestion of poisons and/or drugs at levels that are harmful to the body and the bodily fluid is plasma with blood cellular components. Herein for simplicity, a medical condition arising from the ingestion of poisons and/or drugs at high level are termed Class 1 conditions. Every day in the United States, 120 people die as a result of drug overdose, and another 7,000 are treated for the misuse or abuse of drugs. Nearly 9 out of 10 poisoning deaths are caused by drugs. In 2013, of the 43,982 drug overdose deaths in the United States, 22,767 (51.8%) were related to pharmaceuticals. Of the 22,767 deaths relating to pharmaceutical overdose in 2013, 16,235 (71.3%) involved opioid analgesics and 6,973 (30.6%) involved benzodiazepines. People who died of drug overdoses often had a combination of benzodiazepines and opioid analgesics in their bodies. The most common drugs toxicities involve acetaminophen, anticholinergic drugs, which block the action of the neurotransmitter acetylcholine (such as atropine, scopolamine, *belladonna*, antihistamines, and antipsychotic agents), antidepressant drugs such as amitriptyline, desipramine, and nortriptyline); cholinergic drugs, which stimulate the parasympathetic nervous system (carbamate, pilocarpine, etc.); cocaine and crack cocaine; depressant drugs (tranquilizers, antianxiety drugs, sleeping pills); digoxin, a drug used to regulate the heart; narcotics or opiates (heroin, morphine, codeine, etc.), salicylates (aspirin) and many others.

In an embodiment, the subject is suffering from a Class A condition and the extracorporeal apparatus may have columns situated in the apparatus to afford contact of the incoming bodily fluid with at least a first column having a mixture of a bimodal sanitized compatibilized SCP disposed therein to produce a first eluent. The first eluent may then be introduced to a second column having a mixture of a sanitized compatibilized bimodal SCP and a sanitized compatibilized anionic resin to produce a second eluent. The second column may have a mixture of sanitized compatibilized bimodal SCP to sanitized compatibilized anionic resin ratio of from about 10:1 to about 7:3. The second eluent may be subsequently introduced to a third column comprising a sanitized compatibilized bimodal SCP and a sanitized compatibilized cationic resin to produce a third eluent which may be returned to the subject. The second column may have a ratio of sanitized compatibilized bimodal SCP to sanitized compatibilized cationic resin of from about 10:1 to about 7:3.

In an embodiment, the subject is suffering from a Class 1 condition and the extracorporeal apparatus may have columns situated in the apparatus to afford contact of the incoming bodily fluid with at least a first column having a first bimodal sanitized compatibilized SCP disposed therein to produce a first eluent. The first eluent may then be introduced to a second column having a second sanitized compatibilized bimodal SCP. In some embodiments the first sanitized compatibilized bimodal SCP and the second sanitized compatibilized bimodal SCP are the same, alternatively they are different. The second eluent may be subsequently introduced to a third column comprising a third sanitized compatibilized bimodal SCP to produce a third eluent which may be returned to the subject. In some embodiments the second sanitized compatibilized bimodal SCP and the third sanitized compatibilized bimodal SCP are the same, alternatively they are different.

In an embodiment, a subject suffering from a Class A condition may be treated using the compositions and methodologies disclosed herein. For example, the subject may be placed in fluid communication with an extracorporeal apparatus containing one column of the type disclosed herein so as to allow bodily fluid (e.g., plasma without blood components) of the subject to flow into an inlet port of the device. The extracorporeal apparatus may have a column situated in the apparatus to afford contact of the incoming bodily fluid with a sanitized compatibilized SCP disposed therein, a sanitized compatibilized anionic resin, and a sanitized compatibilized cationic resin to produce an eluent which may be returned to the subject. In the treatment of Class A conditions by contacting plasma without blood cellular components the columns having both a sanitized, compatibilized SCP and a sanitized, compatibilized anion-exchange resin disposed therein may have the ratio of sanitized compatibilized SCP to sanitized compatibilized anion-exchange of about 1:1, alternatively 100:1, alternatively 1:50, alternatively 50:1; a sanitized compatibilized SCP and a sanitized compatibilized cation-exchange resin disposed therein may have the ratio of sanitized compatibilized SCP to sanitized compatibilized cation-exchange resin range from of about 1:1, alternatively 1:50, alternatively 50:1, alternatively 1:25, or alternatively 25:1.

In an embodiment, treatment of a subject suffering from a medical condition may result in a reduction in the level of disease mediators, drugs and/or poisons present in the bodily fluid of said subjects.

For example, the methodologies and compositions disclosed herein may result in a reduction in the level of small molecule mediators of inflammation (e.g., (i) arachidonic acid metabolites such as 8-isoprostane), (ii) autoantibodies, (iii) cytokines, chemokines and growth factors (IL-1β, IL-6, IL-8, TNF-α, PDGF, GM-CSF, M-CSF), (iv) adhesion molecules, (v) matrix metalloproteinases (MMPs) and reactive oxygen species ($H_2O_2$) in subjects suffering from RA.

For example, the methodologies and compositions disclosed herein may result in a reduction in the level of macrophage secreted pro-inflammatory cytokines such as IL-1β, TNF-α, IFN-γ, IL-2, IL-6, IL-8, and nitric oxide (NO), reactive oxygen species, reactive lipids and autoantibodies in subjects suffering from Diabetes Mellitus Type I.

For example, the methodologies and compositions disclosed herein may result in a reduction in the level of (i) eicosanoids (8-isoprostane), (ii) platelet activating factor, (iii) biogenic amines and kinins, (iv) complement-derived peptides, chemotactic peptides, cytokines (IL-1, IL-2, IL-4, IL-6, IL-12, IL-16, IL-18, TNF-α, IFN-γ, TGF-β1), (v) neuropeptides, and (vi) reactive metabolites of oxygen and nitrogen in subjects suffering from IBD. For example, the methodologies and compositions disclosed herein may result in a reduction in the level of autoantibodies Interferon IFN-γ, interleukin IL-18, IL-6 and IL-113, as well as complement fragments (i.e., C3a des Arg), reactive oxygen, nitrogen and lipid species in a subject suffering from SLE.

For example, the methodologies and compositions disclosed herein may result in a restoration of the appropriate levels of proinflammatory cytokines: IFN-γ, TNF-α and IL-12, and IL-10 in a subject suffering from MS.

For example, the methodologies and compositions disclosed herein may result in a reduction in the level of (i) erythropoiesis, leading to anemia (TNF-α, IL-1β, IL-13, TGF-β1), (ii) angiogenesis that facilitates tumor growth (VEGF, EGF, bFGF), (iii) tumor progression and metastasis (TNF-α, IL-1β, IL-6, IL-8), as well as (iv) cachexia (TNF-α, IL-6, IFN-γ) in a subject suffering from cancer.

For example, the methodologies and compositions disclosed herein may result in a reduction in the level of TGF-β1 TNF-α, IL-1β IFN-γ, nephrotoxic molecules such as uric acid, free hemoglobin, CRP, and active lipid—(i.e., 8-isoprostane), oxygen- and nitrogen-species in a subject suffering from CKD.

For example, the methodologies and compositions disclosed herein may result in a reduction in the level of cholesterol, triglyceride, LDL, VLDL, ox-LDL, other biologically active lipids and pro-inflammatory mediators such as C-reactive protein (CRP) and cytokines, particularly TNF-α, IL-1β, IL-6, IL-8 and their precursors in a subject suffering from cardiovascular disease.

For example, the methodologies and compositions disclosed herein may result in a reduction in the level of endotoxins, excess of NO and inflammatory mediators: TNF-α, IL-1β, IL-6, Il-8, CRP, MCP-1, MIP-1α in a subject suffering from SIRS and/or septic shock.

For example, the methodologies and compositions disclosed herein may result in a reduction in the level of endotoxins, excess of NO and inflammatory mediators in a subject suffering from a burn.

For example, the methodologies and compositions disclosed herein may result in a reduction in the level of circulating toxins that are damaging to CNS, particularly ammonia ($NH_3$), marcaptans and phenol in subjects suffering from hepatic encephalopathy.

In an embodiment, from the medical condition is an autoimmune disease of the type disclosed herein and the bodily fluid comprises plasma without blood cellular components. In such embodiments, the subject may be placed in fluid communication with an extracorporeal apparatus a containing single column of the type disclosed herein so as to allow bodily fluid (e.g., plasma without blood components) of the subject to flow into an inlet port of the device. The extracorporeal apparatus may have a single column situated in the apparatus to afford contact of the incoming bodily fluid with a mixture of a sanitized compatibilized bimodal SCP, a sanitized compatibilized anionic resin, and a sanitized compatibilized cationic resin. In such embodiments, the percentage of sanitized compatibilized bimodal SCP in the mixture may range from about 45% to about 65%; the percentage of sanitized compatibilized anionic resin may range from about 20% to about 40%; and the percentage of sanitized compatibilized cationic resin may range from about 10% to about 20% based on the total weight of the mixture.

In an embodiment, from the medical condition is a neoplastic disorder, a SIRS, or SIRS-like disease of the type disclosed herein and the bodily fluid comprises plasma without blood cellular components. In such embodiments, the subject may be placed in fluid communication with an extracorporeal apparatus a containing single column of the type disclosed herein so as to allow bodily fluid (e.g., plasma without blood components) of the subject to flow into an inlet port of the device. The extracorporeal apparatus may have a single column situated in the apparatus to afford contact of the incoming bodily fluid with a mixture of a sanitized compatibilized bimodal SCP, a sanitized compatibilized anionic resin, and a sanitized compatibilized cationic resin. In such embodiments, the percentage of sanitized compatibilized bimodal SCP in the mixture may range from about 45% to about 65%; the percentage of sanitized compatibilized anionic resin may range from about 10% to about 20%; and the percentage of sanitized compatibilized cationic resin may range from about 15% to about 25% based on the total weight of the mixture.

In an embodiment, from the medical condition is a toxicosis, poison overdose, or drug overdose of the type disclosed herein and the bodily fluid comprises plasma without blood cellular components. In such embodiments, the subject may be placed in fluid communication with an extracorporeal apparatus a containing single column of the type disclosed herein so as to allow bodily fluid (e.g., plasma without blood components) of the subject to flow into an inlet port of the device. The extracorporeal apparatus may have a single column situated in the apparatus to afford contact of the incoming bodily fluid with a sanitized compatibilized bimodal SCP.

Herein "a reduction in the level" refers to a decrease in the amount of disease mediators present in the bodily fluid of from about 10% to about 95% based on the level of disease mediators present in the bodily fluid prior to extracorporeal treatment. Alternatively, the reduction may be from about 20% to about 90%, or alternatively from about 30% to about 80%.

The effect of treatment of an medical condition, in terms of progression of the disease state may be monitored by any suitable methodology. For example, the level and amounts of one or more of the disclosed disease mediators in the blood of subjects may be determined and monitored during the course of treatment with the methodologies disclosed herein. In some embodiments, removal of autoimmune, metabolic, inflammatory, degenerative and neoplastic disorders, as well as poisonings and drug overdoses disease mediators may be determined by immunological methods such as HPLC, EPR spectroscopy, enzyme-linked immunoassay (ELISA) and spectrophotometry, or combination thereof. The subject's improvement may also be evaluated clinically utilizing metrics such as but not limited to body temperature, hemodynamic parameters (blood pressure, pulse pressure, EKG) and general signs of improvement. For example, the compositions and methodologies disclosed herein may result in the reduction or inhibition SIRS that develops due to the production of a "cytokine storm." Reduction or inhibition of SIRS may be assessed by determination of the level of C-Reactive Protein (CRP) in the subject. In another embodiment the compositions and methodologies disclosed herein may result in the improvement in SIRS-associated hypotension. In another embodiment the compositions and methodologies disclosed herein may result in the improvement of the general health status of the SIRS-subject as assessed by measurements of organ function such as but not limited to respiratory function, kidney function, and liver function. In another embodiment the compositions and methodologies disclosed herein may result in the improvement of the immunological functioning of the autoimmune disease subject as assessed by standard immunofunction assays such as a complete blood cell count with differential. In another embodiment the compositions and methodologies disclosed herein may result in the improvement of the general health of the cancer subject as assessed by decreases in the morbidity of a subject population and increased incidence of subject survival. In another embodiment the compositions and methodologies disclosed herein may result in detoxification of subjects exposed to toxins, poisons and drug. In an embodiment, a method of the present disclosure comprises extracorporeal cleansing of bodily fluids of a subject suffering from a medical condition of the type disclosed herein. More specifically, it relates to the removal of disease-associated mediators, toxins, poisons and drugs which may permit a subject to recover.

In an embodiment, the present disclosure encompasses a three component composition for use in the treatment of an autoimmune disease, a Class A condition or a Class 1 condition where the first component comprises a bimodal synthetic carbon particle mixture; the second component comprises a bimodal synthetic carbon particle mixture and an anion exchange resin and the third component comprises a bimodal synthetic carbon particle mixture and a cation exchange resin. The type and relative ratios of materials in each component have been disclosed herein. In an embodiment, the components of the composition are disposed within separate columns, such as those found in an extracorporeal apparatus of the type depicted in FIG. 1. Thus the individual components of the composition may not physically contact one another however; a bodily fluid (e.g., whole blood) may contact each component as described herein.

EXAMPLES

The subject matter of the present disclosure having been generally described, the following examples are given as particular embodiments of the disclosure and to demonstrate the practice and advantages thereof. It is understood that the examples are given by way of illustration and are not intended to limit the specification or the claims to follow in any manner.

Example One

The removal of autoimmune disease mediators using the compositions and methodologies disclosed herein were investigated. Two formulations of mesoporous/microporous synthetic carbon (SCP—125/250 & 250/500) with anion exchange resin (AER—UNOsphere Q Media, Bio-Rad, Hercules, Calif.) and cation exchange resin (CER—UNOsphere S Media (Bio-Rad, Hercules, Calif.) were brought to pharmaceutical grade using validated sanitization and fine particulates removal methods disclosed herein. Then SCP, AER and CER were packed into adsorbing devices in sizes representing a 36× scale down from the average human extracorporeal circuit (ECMO) model. Prior to testing, the adsorbents were treated/coated with a solution containing 1% dextran in 09% NaCl, and 3,000U HMW heparin, and filled with 76 mL of spiked human fresh frozen plasma, warmed to 37° C. Before spiking, human fresh frozen plasma blood was filtered using 20 μm Pall filter, which was disconnected during testing. In the extracorporeal experiment, the back-pressure determined the flow rate generated by a peristaltic pump. The sampling occurred at 0, 1, and 4 hours. The cartridges containing SCP/AER/CER material were oriented vertically. The experiments were done in duplicates. Human fresh frozen plasma was spiked with inflammatory cytokines: TNF-α, IL-1β, IL-4, IL-6, IL-8, IL-17, TGF-b 1, INF-γ), and gamma globulins (Sigma-Aldrich, St. Louis, Mo.: containing IgG and IgM), mimicking autoimmune disease states.

Figure 3:
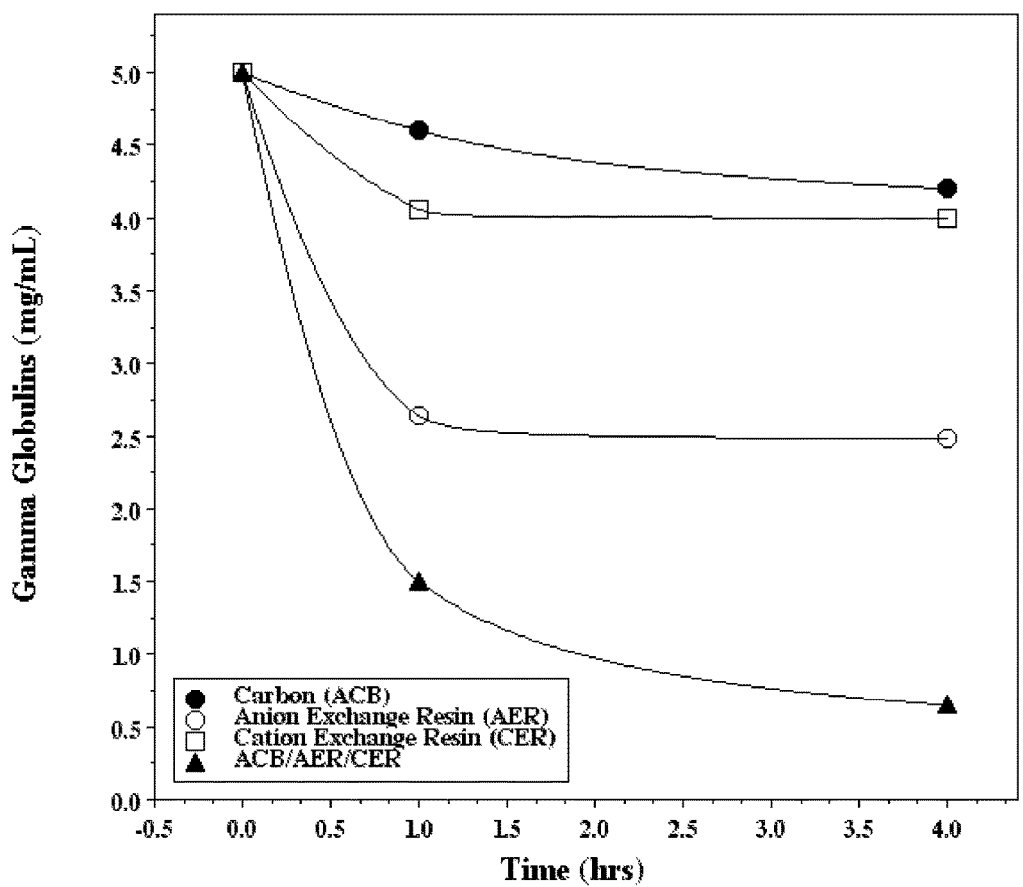
FIG. 3 represents effects of mesoporous/microporous synthetic carbon (SCP), anion exchange resin (AER), or cation exchange resins (CER) and combination of SCP/AER/CER on plasma clearances of gamma globulins.
Figure 4:
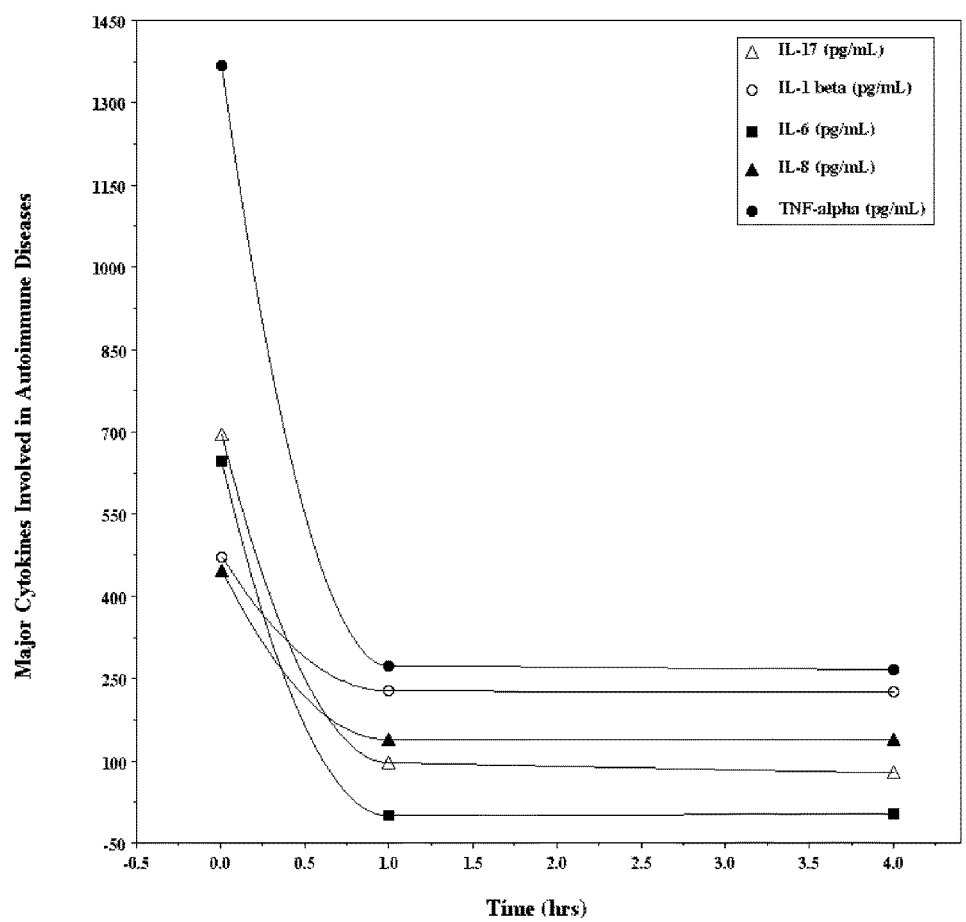
FIG. 4 represents the effect of mesoporous/microporous synthetic carbon (SCP), anion exchange resin (AER) and cation exchange resin (CER) on plasma clearances of the indicated molecules.
Figure 5:
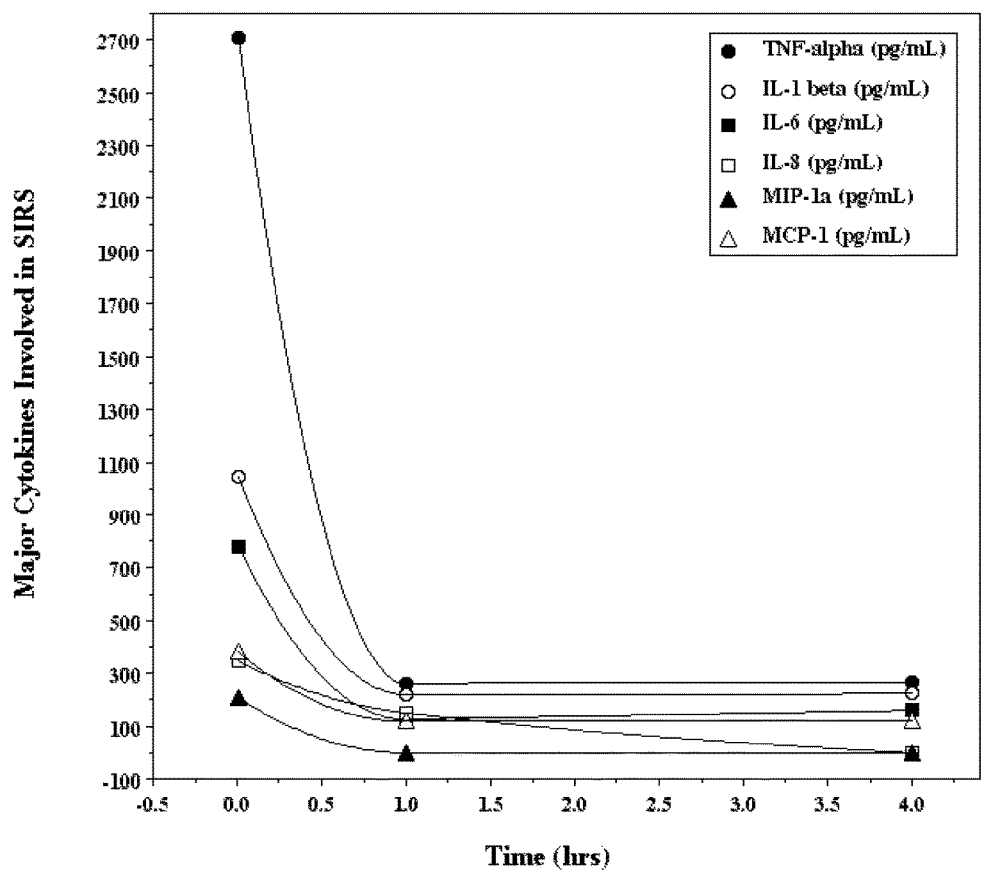
FIGS. 5-10 depict the amount of indicated mediator present as a function of time for the samples from Example 2.
Figure 6:
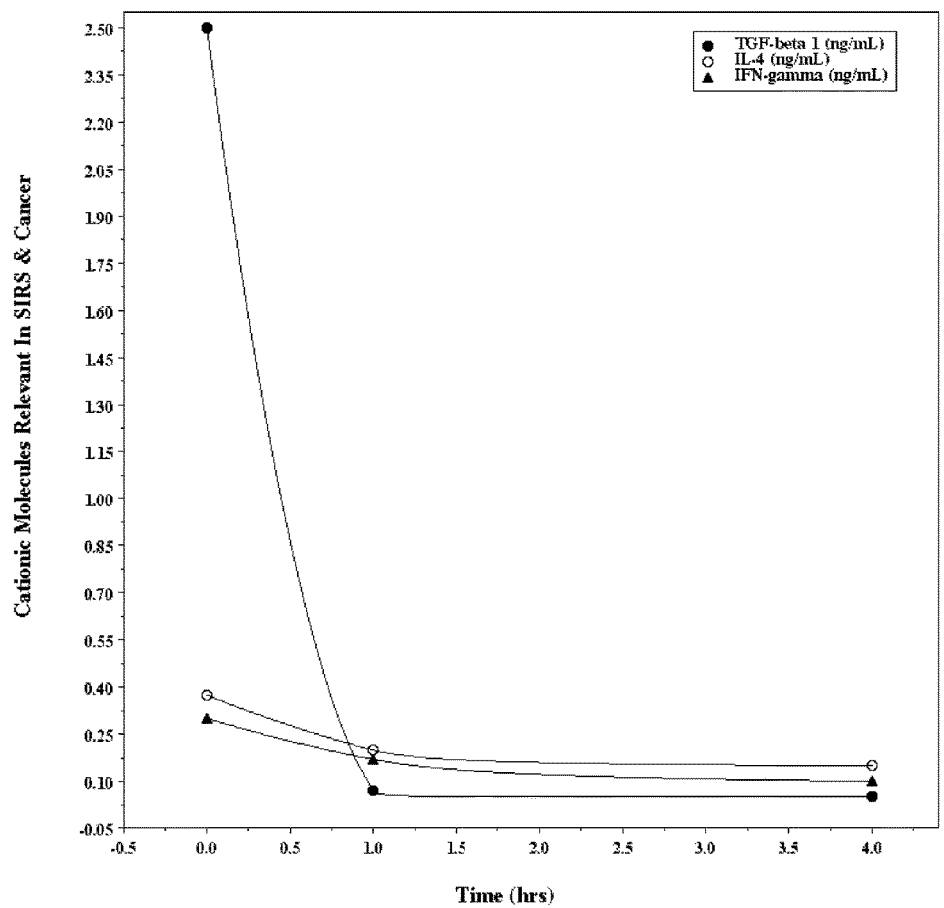
Figure 7:
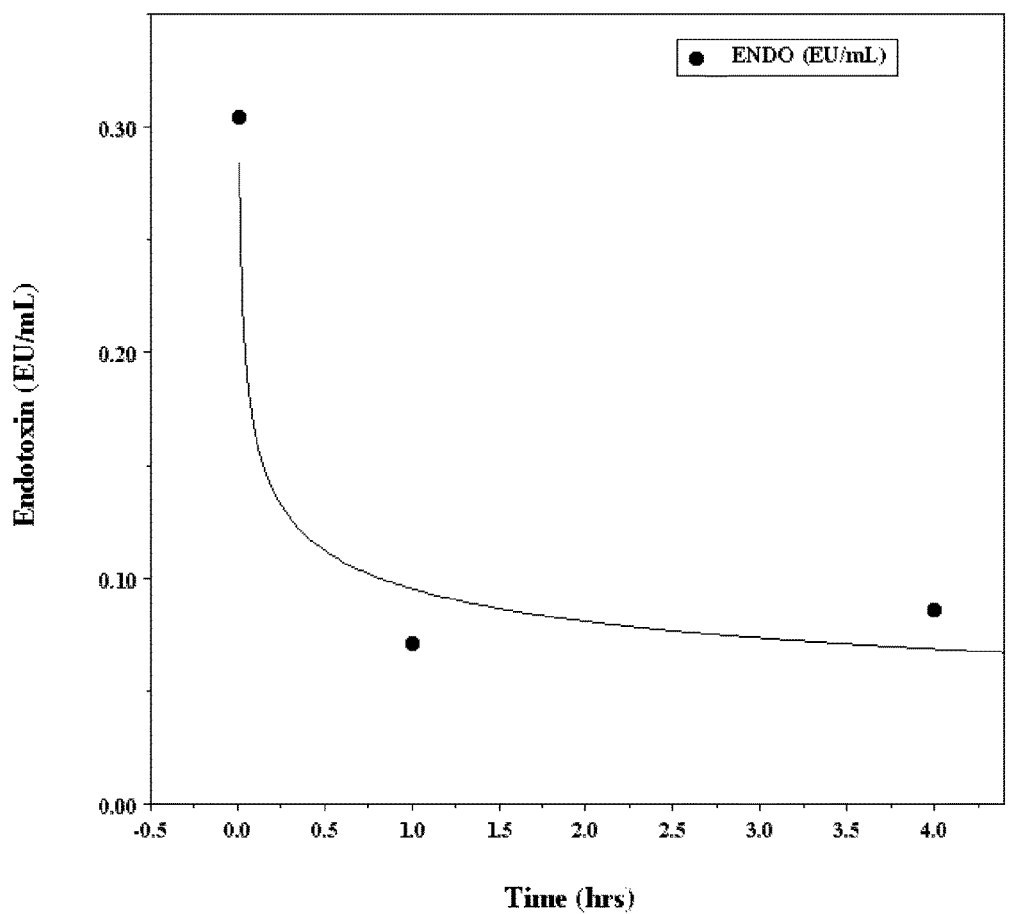
Figure 8:
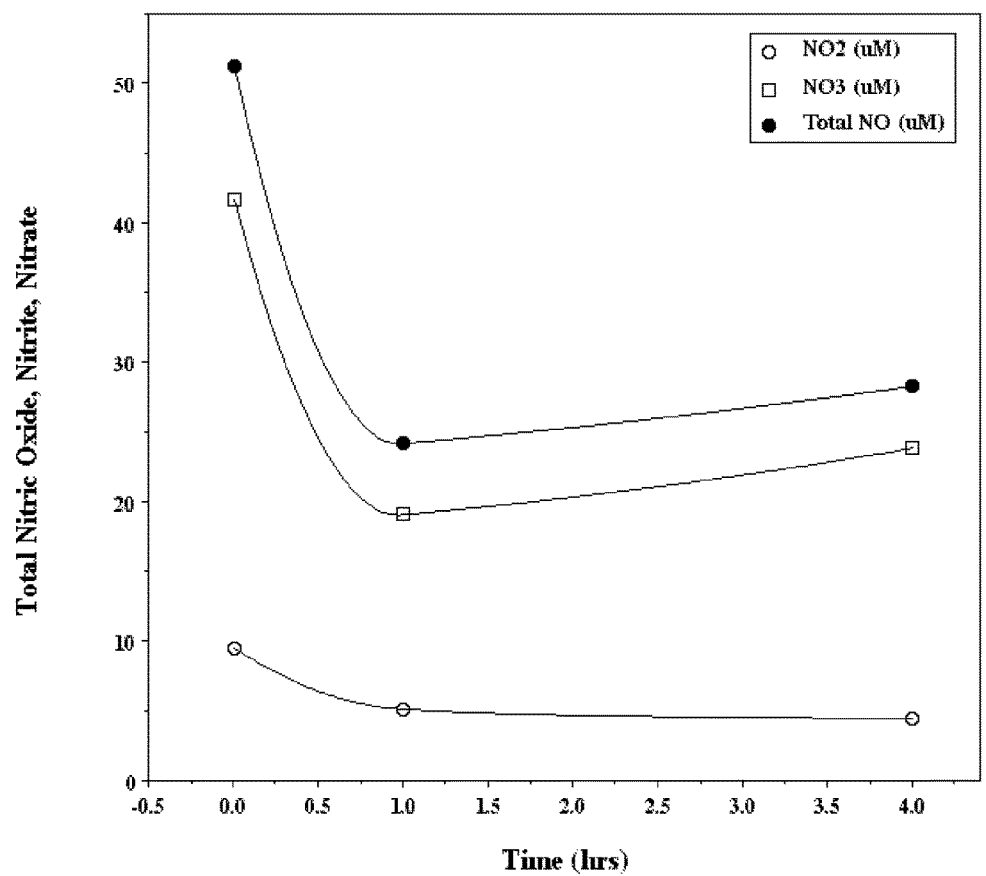
Figure 9:
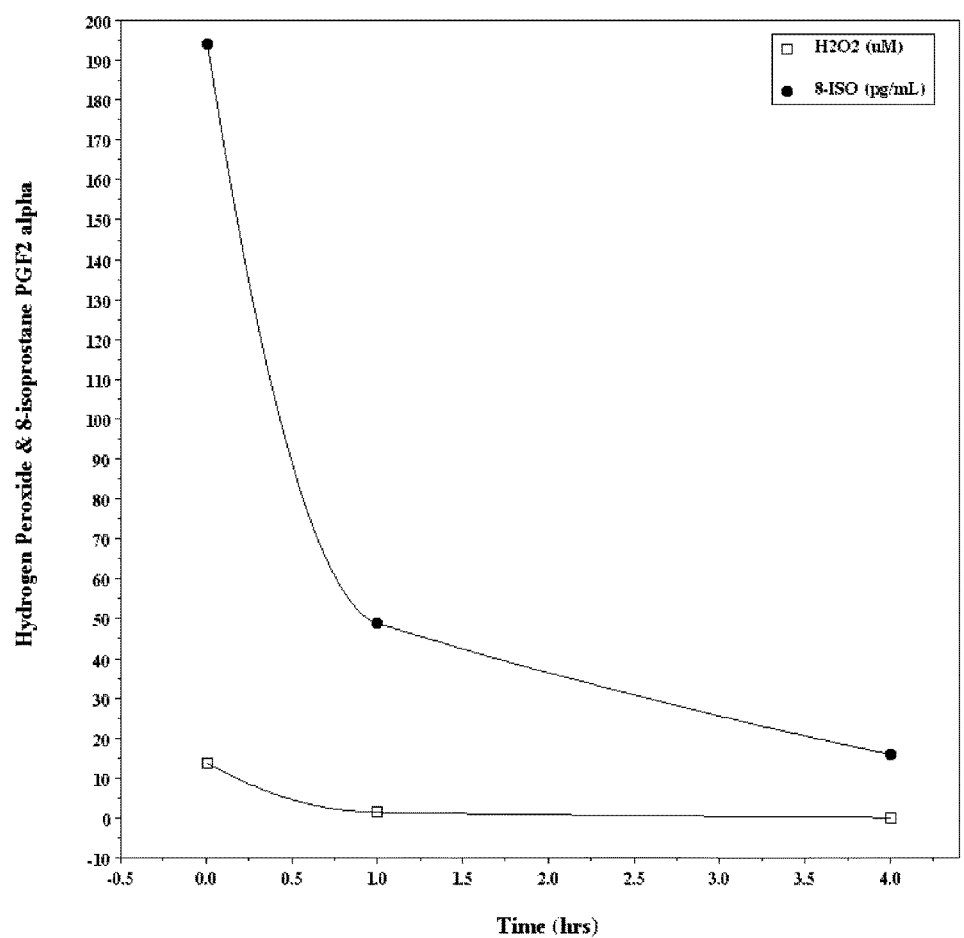
Figure 10:
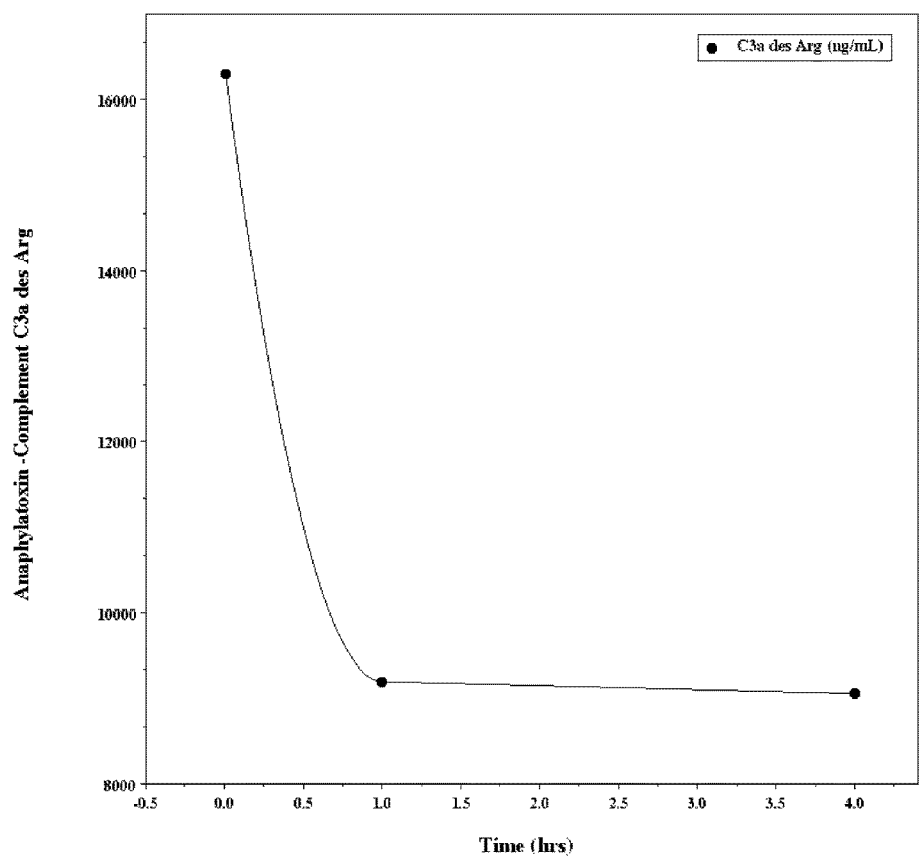

Cytokines/chemokines (TNF-α, IL-1β, IL-4, IL-6, IL-8, IL-17, TGF-β1, INF-γ) were evaluated by the Multi-Analyte Custom ELISArray Kit (CELISA-CMEH0400A, QIAGEN Inc., Valencia, Calif.). This ELISArray Kits was designed to survey a specific panel of cytokines or chemokines involved in autoimmunity, inflammation, or T-cell biology in cell culture supernatant, serum or plasma. The ELISA was conducted in accordance with the protocol specified by the manufacturer. The ELISA was read using Bio-Rad Microplate ELISA reader (Model 3550-UV, Bio-Rad Laboratories, Hercules, Calif.) and calculated using Microplate Manager Software Version 2.2 (Bio-Rad Laboratories). Gamma globulin concentrations were established with Piccolo General Chemistry 13 reagent disk and confirmed by radial immunodifussion. The results, depicted in FIGS. 3 and 4, demonstrate the combination of SCP/AER/CER effectively cleared all relevant mediators of autoimmune diseases, globulins and cytokines.

Example Two

The removal of SIRS-like disease mediators using the compositions and methodologies disclosed herein were investigated. Two formulations of mesoporous/microporous synthetic carbon (SCP—125/250 & 250/500) with anion exchange resin (AER) and cation exchange resin (CER) were brought to pharmaceutical grade using validated sanitization and fine particulates removal methods as disclosed herein. Then SCP, AER and CER were packed into adsorbing devices in sizes representing a 36× scale down from the average human extracorporeal circuit (ECMO) model. Prior to testing, the adsorbents were treated/coated with a solution containing 1% dextran in 09% NaCl, and 3,000U HMW heparin and filled with 76 mL of spiked human fresh frozen plasma, warmed to 37° C. Before spiking, human fresh frozen plasma blood was filtered using 20 μm Pall filter, which was disconnected during testing. In the extracorporeal experiment, the back-pressure determined the flow rate generated by a peristaltic pump. The sampling occurred at 0, 1, and 4 hours. The cartridges containing SCP/AER/CER material were oriented vertically. The experiments were done in duplicates. Human fresh frozen plasma was spiked with endotoxin (Sigma-Aldrich), hydrogen peroxide (Sigma-Aldrich), nitrite (Sigma-Aldrich), nitrate (Sigma-Aldrich), 8-isoprostane (Cayman Chemical, Ann Arbor, Mich.), Zymosan (Sigma Chemical) to activate alternative pathway of complement and generate C3a des Arg, and inflammatory cytokines (QIAGEN, Inc., Valencia, Calif.): TNF-α, IL-1β, IL-4, IL-6, IL-8, MW-1α, MCP-1 TGF-β1, INF-γ), mimicking SIRS-like disease state.

Cytokines/chemokines (TNF-α, IL-1β, IL-4, IL-6, IL-8, MW-1α, MCP-1 TGF-β1, INF-γ) were evaluated by the Multi-Analyte Custom ELISArray Kit (CELISA-CMEH0400A, QIAGEN Inc., Valencia, Calif.). This ELISArray Kits was designed to survey a specific panel of cytokines or chemokines involved in autoimmunity, inflammation, or T-cell biology in cell culture supernatant, serum or plasma. The ELISA was conducted in accordance with the protocol specified by the manufacturer. The ELISA was read using Bio-Rad Microplate ELISA reader (Model 3550-UV, Bio-Rad Laboratories, Hercules, Calif.) and calculated using Microplate Manager Software Version 2.2 (Bio-Rad Laboratories). $NO_2/NO_3$=NO and 8-isoprostane PGF2α concentrations were established with the Cayman Chemical Nitrate/Nitrite Assay Kit and 8-isoprostane EIA Kit respectively. Endotoxins (LPS) were evaluated with QCL-1000 Limulus Amebocyte Lysate Assay Kit. Complement C3a des Arg was assessed with Abcam (USA) ELISA Kit. $H_2O_2$ was measured using spectrophometric method. The results of target molecules clearances are presented in FIGS. 5-10. The results showed the combination of SCP/AER/CER to be effective in removal of SIRS-like disease mediators.

Example Three

The removal of neoplastic disease mediators using the compositions and methodologies disclosed herein were investigated. Two formulations of mesoporous/microporous synthetic carbon (SCP—125/250 & 250/500) with anion exchange resin (AER) and cation exchange resin (CER) were brought to pharmaceutical grade using validated sanitization and fine particulates removal methods as disclosed herein. Then SCP, AER and CER were packed into adsorbing devices in sizes representing a 36× scale down from the average human extracorporeal circuit (ECMO) model. Prior to testing, the adsorbents were treated/coated with a solution containing 1% dextran in 09% NaCl, and 3,000U HMW heparin, and filled with 76 mL of spiked human fresh frozen plasma, warmed to 37° C. Before spiking, human fresh frozen plasma blood was filtered using 20 μm Pall filter, which was disconnected during testing. In the extracorporeal experiment, the back-pressure determined the flow rate generated by a peristaltic pump. The sampling occurred at 0, 1, and 4 hours. The cartridges containing SCP/AER/CER material were oriented vertically. The experiments were done in duplicates. Human fresh frozen plasma was spiked with inflammatory cytokines and growth factors (QIAGEN, Inc., Valencia, Calif.): TNF-α, IL-1β, IL-8, INF-γ, VEGF, ECF, FGF-β), mimicking cancer-related angiogenesis, anemia and cachexia.

Figure 11:
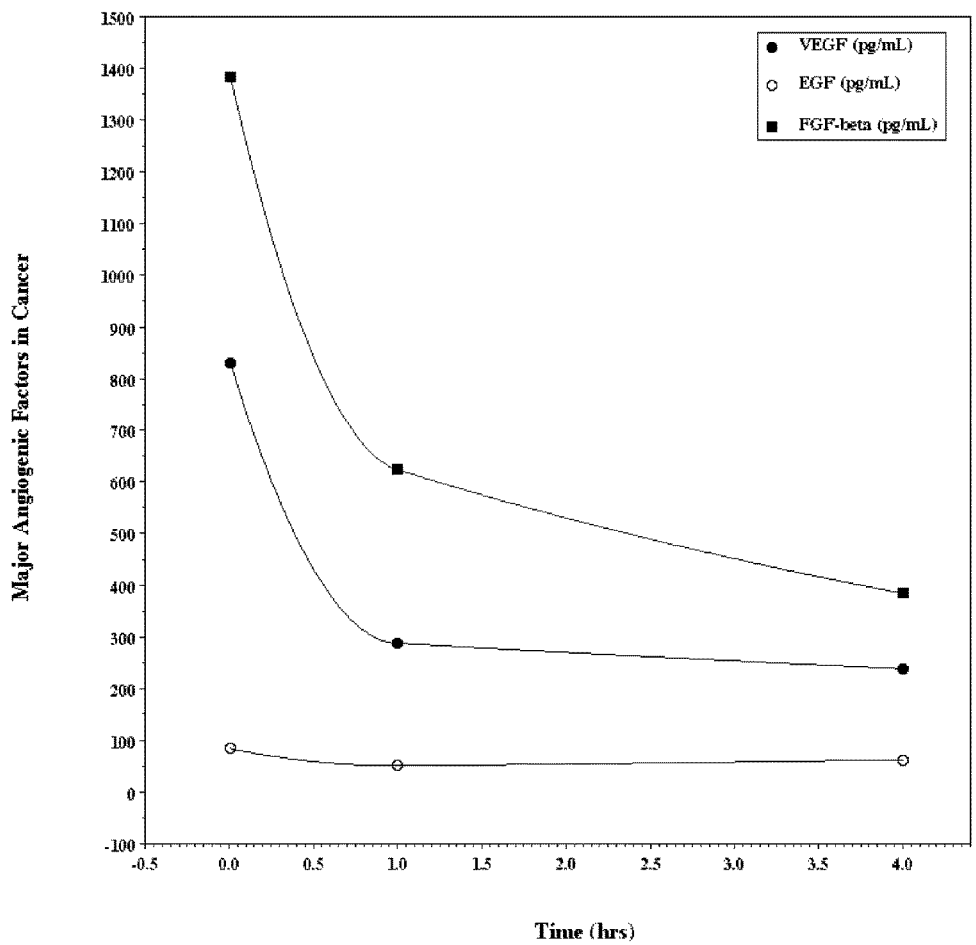
FIGS. 11 and 12 depict the amount of indicated mediator present as a function of time for the samples from Example 3.
Figure 12:
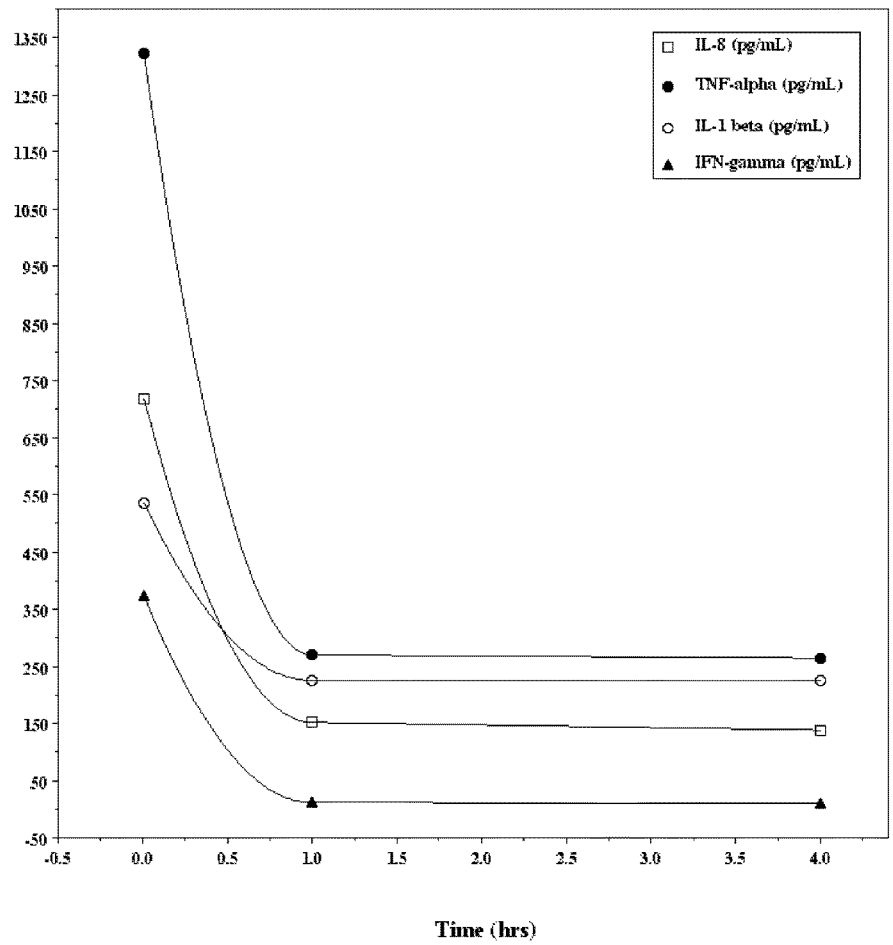
Figure 13:
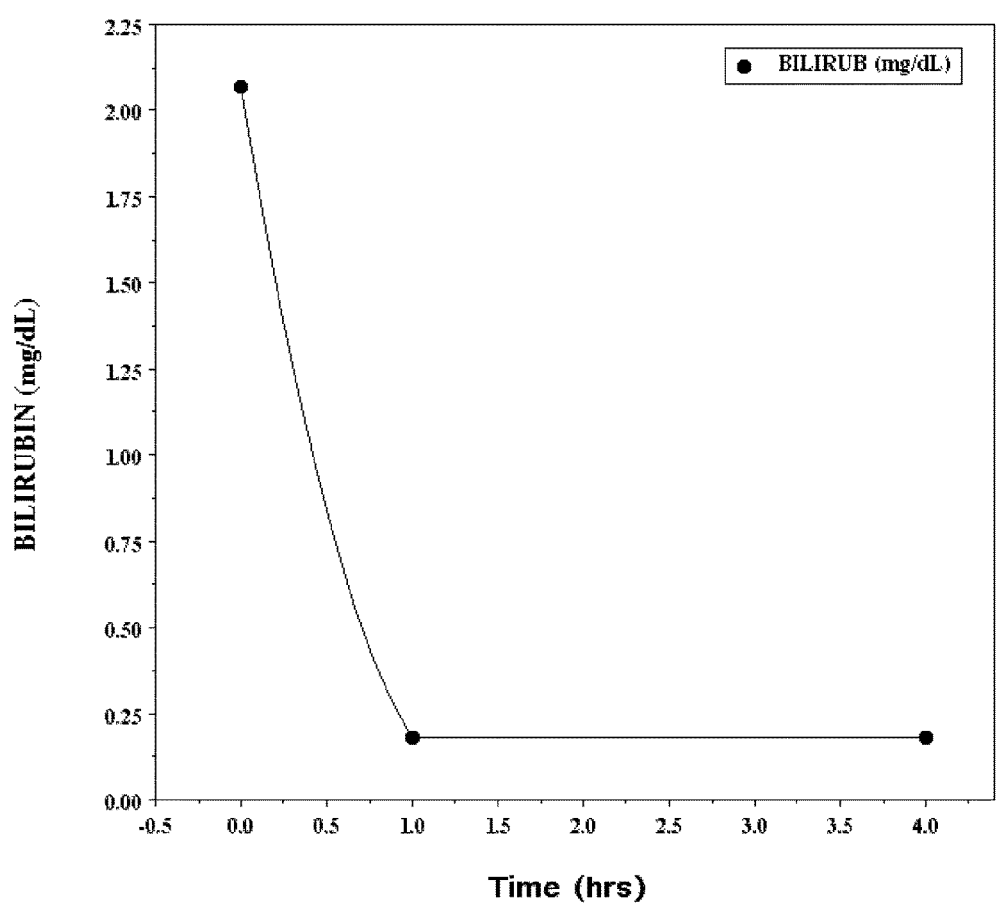
FIG. 13 depicts the result of bilirubin clearances for the samples from Example 4.
Figure 14:
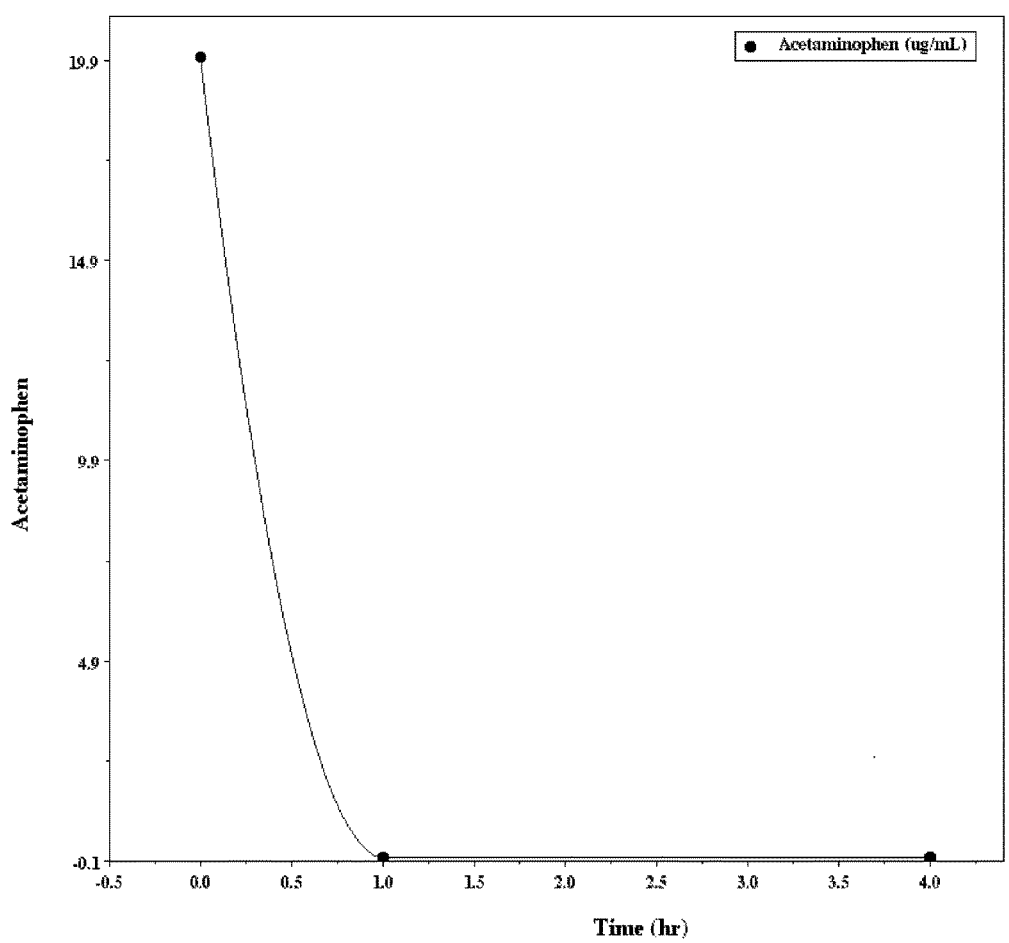
FIGS. 14-17 depict the amount of indicated drug present as a function of time for the samples from Example 5.
Figure 15:
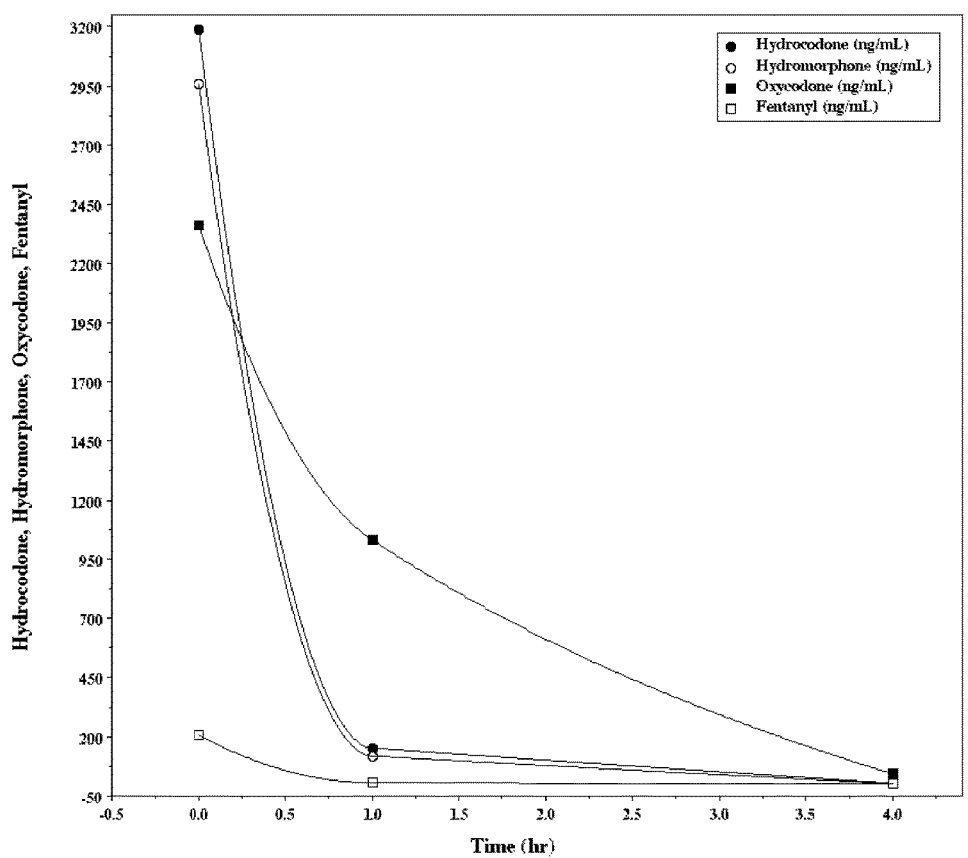
Figure 16:
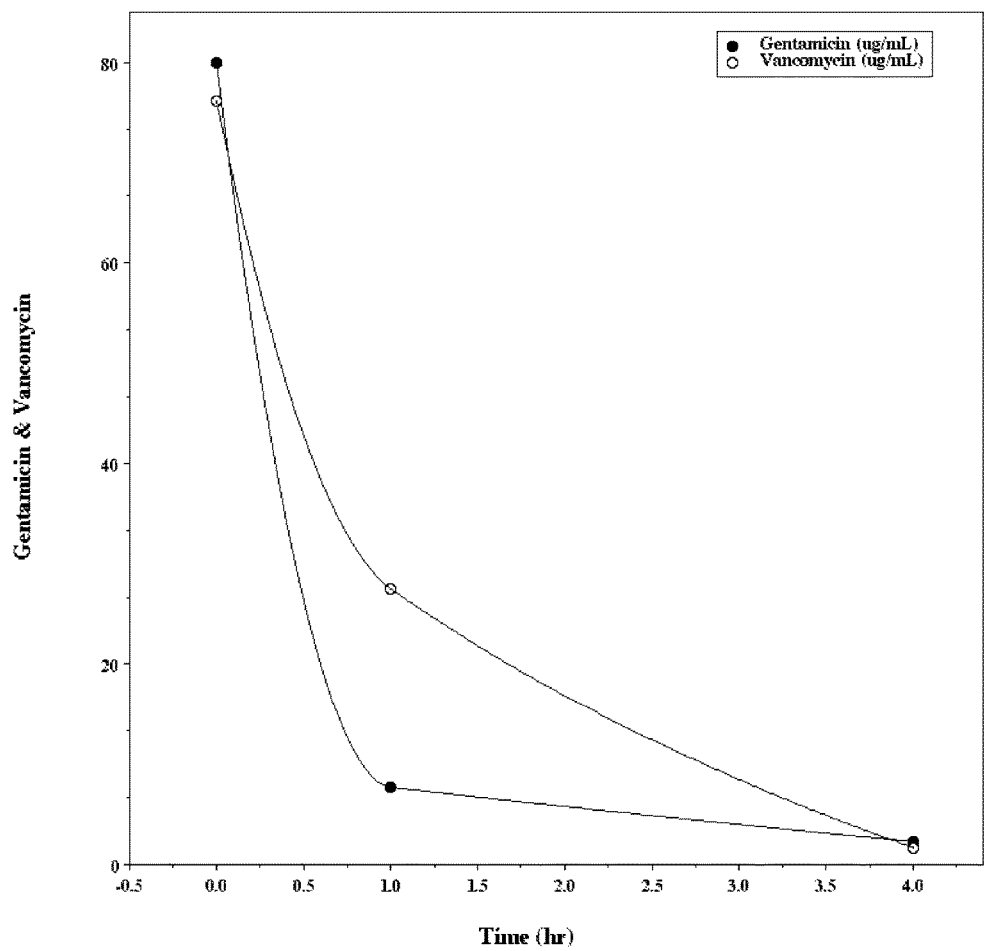
Figure 17:
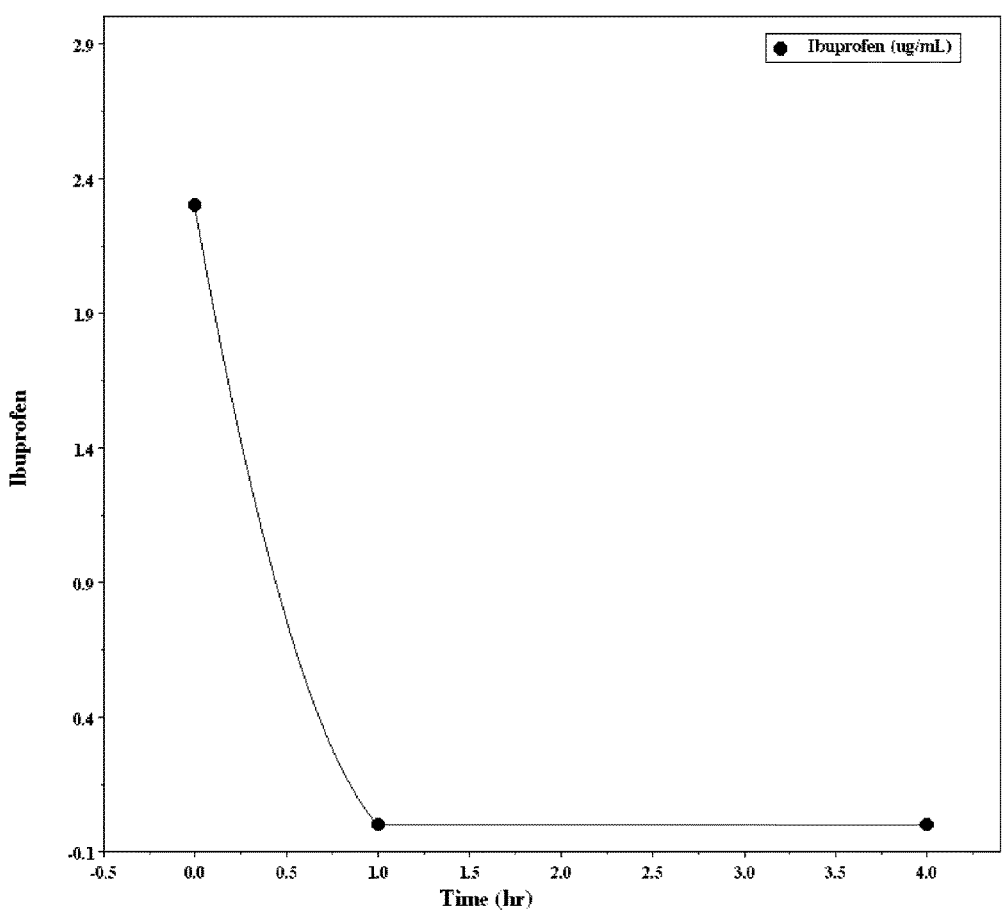

Cytokines/chemokines/growth factors (TNF-α, IL-1β, IL-8, INF-γ, VEGF, ECF, FGF-β) were evaluated by the Multi-Analyte Custom ELISArray Kit (CELISA-CMEH0400A, QIAGEN Inc., Valencia, Calif.). This ELISArray Kits was designed to survey a specific panel of cytokines or chemokines involved in autoimmunity, inflammation, or T-cell biology in cell culture supernatant, serum or plasma. The ELISA was conducted in accordance with the protocol specified by the manufacturer. The ELISA was read using Bio-Rad Microplate ELISA reader (Model 3550-UV, Bio-Rad Laboratories, Hercules, Calif.) and calculated using Microplate Manager Software Version 2.2 (Bio-Rad Laboratories). The results of target molecules clearances are presented in FIGS. 11 and 12. The results demonstrate the combination of SCP/AER/CER is effectively eliminated the investigated mediators of cancer-related angiogenesis, anemia and cachexia.

Example Four

The removal of endogenous toxin-bilirubin using the compositions and methodologies disclosed herein were investigated. Two formulations of mesoporous/microporous synthetic carbon (SCP 125/250 & 250/500) were brought to pharmaceutical grade using validated sanitization and fine particulates removal methods as disclosed herein. Then SCP was packed into adsorbing devices in sizes representing a 36× scale down from the average human extracorporeal circuit (ECMO) model. Prior to testing, the adsorbents were treated/coated with a solution containing 1% dextran in 09% NaCl, and 3,000U HMW heparin (Heparin, Sodium Injection, and filled with 76 mL of spiked human fresh frozen plasma, warmed to 37° C. Before spiking, human fresh frozen plasma was filtered using 20 μm Pall filter, which was disconnected during testing. In the extracorporeal experiment, the back-pressure determined the flow rate generated by a peristaltic pump. The sampling occurred at 0, 1, and 4 hours. The cartridges containing SCP material were oriented vertically. The experiments were done in duplicates. Human fresh frozen plasma was spiked with bilirubin. Direct bilirubin was evaluated using Piccolo Hepatic Function Panel Reagent Disc (Abaxis). The results demonstrate that SCP is an effective sorbent for the elimination of excess of bilirubin from human plasma.

In consideration of using whole blood cleansing technology, unless otherwise indicated, Examples 5-8 were carried out using samples of whole blood.

Example Five

The removal of drugs and poisons using the compositions and methodologies disclosed herein were investigated. Two formulations of mesoporous/microporous synthetic carbon (SCP 125/250 & 250/500) were brought to pharmaceutical grade using the validated sanitization and fine particulates removal methods disclosed herein. Then SCP was packed into adsorbing devices in sizes representing a 36× scale down from the average human extracorporeal circuit (ECMO) model. Prior to testing, the adsorbents were treated/coated with a solution containing 1% dextran in 09% NaCl and 3,000U HMW heparin (Heparin, Sodium Injection, and filled with 76 mL of spiked human whole blood, warmed to 37° C. Before spiking, human blood was filtered using 20 μm Pall filter, which was disconnected during testing. In the extracorporeal experiment, the back-pressure determined the flow rate generated by a peristaltic pump. The sampling occurred at 0, 1, and 4 hours. The cartridges containing SCP were oriented vertically. The experiments were done in duplicates. Human whole blood was spiked with Acetaminophen, Hydrocodone, Hydromorphone, Oxycodone, Hydrocodone, Fentanyl, Gentamicin, Vancomycin, Ibuprofen, Radiocontrast Opriray 350, and ethanol. Acetaminophen, Hydrocodone, Hydromorphone, Oxycodone, Hydrocodone, Fentanyl, Gentamicin, Vancomycin and Ibuprofen were evaluated at Any Lab Test Now, Sioux Falls, S. Dak. Radiocontrast and ethanol clearances were established by the spectrophotometric methods. The results of target drugs and toxins clearances are presented in FIGS. 14-17 and Tables 1 and 2. The results demonstrate that SCP effectively eliminated drugs and toxins from human whole blood.

TABLE 1

| | Extracorporeal Run # 1 | | | Extracorporeal Run # 2 | | |
|---|---|---|---|---|---|---|
| | PARAMETER | | | | | |
| | Baseline | 1 hr (% decrease) | 4 hr (% decrease) | Baseline | 1 hr (% decrease) | 4 hr (% decrease) |
| Radio-contrast | 2.010 | 0.177 | 0.000 | 2.030 | 0.175 | 0.073 |
| | 0 | 91.2% | 100% | 0 | 91.3% | 96.4% |

TABLE 2

| | PARAMETER | | | | | | | | |
|---|---|---|---|---|---|---|---|---|---|
| | 0 hour Baseline | 0 hour | 1 hour Baseline | 1 hour | 1 hour (% decrease) | 4 hour Baseline | 4 hour | 4 hour (% decrease) | 24 hour | 24 hour (% decrease) |
| | | | | | Run # 1 | | | | | |
| Ethanol | 0.223 | 0.226 | 0.251 | 0.023 | 89.82% | 0.204 | −0.026 | 100% | 0.049 | 78.32% |
| | | | | | Run # 2 | | | | | |
| Ethanol | 0.223 | 0.212 | 0.248 | 0.015 | 92.92% | 0.208 | −0.015 | 100% | 0.041 | 80.66% |

Example Six

The removal of selected mediators of autoimmune, neoplastic and SIRS-like disorders using the compositions and methodologies disclosed herein were investigated. Two formulations of mesoporous/microporous synthetic carbon (125/250 & 250/500) were brought to pharmaceutical grade using the validated sanitization and fine particulates removal methods disclosed herein. Then mesoporous/microporous synthetic carbon beads were used in the agitation testing protocol identical to that described in Examples 1-5, or packed into adsorbing devices in sizes representing a 30× scale down from the average human extracorporeal circuit (ECMO) model. Prior to testing, the carbon beads were treated/coated with a solution containing 1% dextran in 09% NaCl, and 3,000U HMW heparin, and later in the agitation experiment combined with 15 mL of spiked fresh human blood or in extracorporeal experiment filled with 76 mL of spiked fresh human whole blood, warmed to 37° C. Before spiking, human whole blood was filtered using 20 μm Pall filter, which was disconnected during testing. In the extracorporeal experiment, the back-pressure determined the flow rate generated by a peristaltic pump. In both experiments, sampling occurred at 0, 1, and 4 hours. In the agitation experiments tubes containing carbon beads were mixed horizontally, and in the extracorporeal experiments the cartridges containing carbon adsorbents were oriented vertically.

In both experiments, done in duplicates, human whole blood was spiked with inflammatory cytokines (TNF-α, IL-1β, IL-4. IL-6, IL-8, IL-10, IFN-γ, TGF-β1), endotoxin, NO, $H_2O_2$, mimicking disease state. Cytokines/chemokines (TNF-α, IL-1β, IL-4, IL-6, IL-8, IL-10, TGF-β1, INF-γ) were evaluated by the Multi-Analyte Custom ELISArray Kit (CELISA-CMEH0400A, QIAGEN Inc., Valencia, Calif.). This ELISArray Kits was designed to survey a specific panel of cytokines or chemokines involved in autoimmunity, inflammation, or T-cell biology in cell culture supernatant, serum or plasma. The ELISA was conducted in accordance with the protocol specified by the manufacturer. The ELISA was read using Bio-Rad Microplate ELISA reader (Model 3550-UV, Bio-Rad Laboratories, Hercules, Calif.) and calculated using Microplate Manager Software Version 2.2 (Bio-Rad Laboratories). $NO_2/NO_3$=NO concentrations after ethyl were established with the Cayman Chemical Nitrate/Nitrite Assay Kit. Endotoxins (LPS) were evaluated with QCL-1000 Limulus Amebocyte Lysate Assay Kit (Product No. 50-647U, BioWhittaker, Walkersville, Md.). CRP was estimated using the commercial diagnostic kit from SIGMA Diagnostics (Procedure No. 371-A, St. Louis, Mo.). Hydrogen peroxide was assayed spectrophotometrically. The results of target molecule clearances are presented in TABLES 3-14 for extracorporeal testing and TABLES 3A-14A for agitation testing. The results suggest mesoporous/microporous SCP to be effective in removal of disease mediators responsible for autoimmune, SIRS-like, immune system suppression, hypotension and MOF. Synthetic carbon beads under either experimental condition, extracorporeal or agitation, showed similar cleansing effectiveness toward these disease mediators.

TABLE 3

| INTERFEREON GAMMA (EXTRACORPOREAL CIRCUIT) | | | |
|---|---|---|---|
| RUN 1 Time (hr) | pg/mL whole blood | pg/76 mL whole blood | pg per g sorbent |
| 0 | 87.31 | 6,635 | — |
| 1 | 25.29 | 1,922 | 589.1 |
| 4 | 27.69 | 2,105 | 566.2 |

TABLE 3A

| INTERFEREON GAMMA (AGITATION) | | | |
|---|---|---|---|
| RUN 1 Time (hr) | pg/mL whole blood | pg/15 mL whole blood | pg per g sorbent |
| 0 | 86.70 | 1,300.5 | — |
| 1 | 28.90 | 433.5 | 548.7 |
| 4 | 28.9 | 433.5 | 548.7 |

TABLE 4

CRP (EXTRACORPOREAL CIRCUIT)

| RUN 1 Time (hr) | mg/dL whole blood | % decrease |
|---|---|---|
| 0 | 2.01 | — |
| 1 | 0.157 | 92.2 |
| 4 | 0.377- | 81.2 |

TABLE 4A

CRP (AGITATION)

| RUN 1 Time (hr) | mg/dL whole blood | % decrease |
|---|---|---|
| 0 | 2.29 | — |
| 1 | 0.472 | 79.4 |
| 4 | 0.251 | 89.03 |

TABLE 5

ENDOTOXIN (EXTRACORPOREAL CIRCUIT)

| RUN 1 Time (hr) | EU/mL whole blood | EU/76 mL whole blood | EU per g sorbent | RUN 2 Time (hr) | EU/mL whole blood | EU/76 mL whole blood | EU per g sorbent |
|---|---|---|---|---|---|---|---|
| 0 | 0.747 | 58.82 | — | 0 | 0.755 | 57.38 | — |
| 1 | 0.205 | 15.58 | 5.405 | 1 | 0.190 | 14.47 | 5.364 |
| 4 | 0.178 | 13.53 | 5.661 | 4 | 0.175 | 13.32 | 5.507 |

TABLE 5A

ENDOTOXIN (AGITATION)

| | RUN 1 | | | | RUN 2 | | |
|---|---|---|---|---|---|---|---|
| Time (hr) | EU/mL whole blood | EU/15 mL whole blood | EU per g sorbent | Time (hr) | EU/mL whole blood | EU/15 mL whole blood | EU per g sorbent |
| 0 | 0.831 | 12.46 | — | 0 | 0.757 | 11.359 | — |
| 1 | 0.262 | 3.926 | 5.401 | 1 | 0.228 | 3.426 | 4.989 |
| 4 | 0.102 | 1.537 | 6.913 | 4 | 0.173 | 3.595 | 5.547 |

TABLE 6

TGF-β1 (EXTRACORPOREAL CIRCUIT)

| | RUN 1 | | | | RUN 2 | | |
|---|---|---|---|---|---|---|---|
| Time (hr) | pg/mL whole blood | pg/76 mL whole blood | pg per g sorbent | Time (hr) | pg/mL whole blood | pg/76 mL whole blood | pg per g sorbent |
| 0 | 1,303.5 | 99,066 | — | 0 | 1,291 | 98,116 | — |
| 1 | 1,149.3 | 87,346 | 1,465 | 1 | 1,081 | 82,156 | 1,995 |
| 4 | 778.95 | 59,200 | 4,983 | 4 | 738.1 | 56,095 | 5,252 |

TABLE 6A

TGF-β1 (AGITATION)

| | RUN 1 | | | | RUN 2 | | |
|---|---|---|---|---|---|---|---|
| Time (hr) | pg/mL whole blood | pg/15 mL whole blood | pg per g sorbent | Time (hr) | pg/mL whole blood | pg/15 mL whole blood | pg per g sorbent |
| 0 | 1,249 | 18,735 | — | 0 | 1,303 | 19,545 | — |
| 1 | 855 | 12.825 | 3,740 | 1 | 950.2 | 14,253 | 3,349 |
| 4 | 783 | 11,745 | 4,424 | 4 | 768.4 | 11,520 | 5,063 |

TABLE 7

TNF-γ (EXTRACORPOREAL CIRCUIT)

| RUN 1 Time (hr) | pg/mL whole blood | pg/76 mL whole blood | pg per g sorbent | RUN 2 Time (hr) |
|---|---|---|---|---|
| 0 | 1,898.9 | 144,323 | — | 0 |
| 1 | 1,506.2 | 114,469 | 3,731.7 | 1 |
| 4 | 825.4 | 62,735 | 10,198.7 | 4 |

TABLE 7A

TNF-α (AGITATION)

| RUN 1 Time (hr) | pg/mL whole blood | pg/15 mL whole blood | pg per g sorbent | RUN 2 Time (hr) |
|---|---|---|---|---|
| 0 | 2,007.1 | 30,106.5 | — | 0 |
| 1 | 1,614.3 | 24,214.5 | 3,729.1 | 1 |
| 4 | 681.5 | 10,222.8 | 12,584.6 | 4 |

TABLE 8

IL-4 (EXTRACORPOREAL CIRCUIT)

| | RUN 1 | | | | RUN 2 | | |
|---|---|---|---|---|---|---|---|
| Time (hr) | pg/mL whole blood | pg/76 mL whole blood | pg per g sorbent | Time (hr) | pg/mL whole blood | pg/76 mL whole blood | pg per g sorbent |
| 0 | 54.29 | 4,125.8 | — | 0 | 40.83 | 3,103.16 | — |
| 1 | 48.99 | 3,723.8 | 50.25 | 1 | 37.54 | 2,853.04 | 31.26 |
| 4 | 38.69 | 2,940.7 | 148.1 | 4 | 32.92 | 2,501.84 | 75.16 |

TABLE 8A

IL-4 (AGITATION)

| | RUN 1 | | | | RUN 2 | | |
|---|---|---|---|---|---|---|---|
| Time (hr) | pg/mL whole blood | pg/15 mL whole blood | pg per g sorbent | Time (hr) | pg/mL whole blood | pg/15 mL whole blood | pg per g sorbent |
| 0 | 71.03 | 1,065.5 | — | 0 | 76.23 | 1,143.4 | — |
| 1 | 66.41 | 996.23 | 43.84 | 1 | 76.23 | 1,143.4 | 0 |
| 4 | 62.37 | 935.59 | 82.22 | 4 | 62.37 | 935.59 | 131.52 |

TABLE 9

IL-6 (EXTRACORPOREAL CIRCUIT)

| | RUN 1 | | | | RUN 2 | | |
|---|---|---|---|---|---|---|---|
| Time (hr) | pg/mL whole blood | pg/76 mL whole blood | pg per g sorbent | Time (hr) | pg/mL whole blood | pg/76 mL whole blood | pg per g sorbent |
| 0 | 5,467.8 | 415,550 | — | 0 | 4,619.4 | 351,080 | — |
| 1 | 2,835.5 | 215,500 | 25,006 | 1 | 3,308.1 | 251,420 | 12,450 |
| 4 | 1,473.9 | 112,020 | 37,941 | 4 | 1,551.4 | 117,910 | 29,150 |

TABLE 9A

IL-6 (AGITATION)

| | RUN 1 | | | | RUN 2 | | |
|---|---|---|---|---|---|---|---|
| Time (hr) | pg/mL whole blood | pg/15 mL whole blood | pg per g sorbent | Time (hr) | pg/mL whole blood | pg/15 mL whole blood | pg per g sorbent |
| 0 | 4,958.5 | 74,378 | — | 0 | 4,673 | 70,105 | — |
| 1 | 1,944.6 | 29,169 | 28,610 | 1 | 1,696 | 25,450 | 28,260 |
| 4 | 999.4 | 14,991 | 37,590 | 4 | 859 | 12,899 | 36,210 |

TABLE 10

IL-8 (EXTRACORPOREAL CIRCUIT)

| | RUN 1 | | | | RUN 2 | | |
|---|---|---|---|---|---|---|---|
| Time (hr) | pg/mL whole blood | pg/76 mL whole blood | pg per g sorbent | Time (hr) | pg/mL whole blood | pg/76 mL whole blood | pg per g sorbent |
| 0 | 2,139 | 162,576 | — | 0 | 2,366 | 179,845 | — |
| 1 | 1,816 | 138,036 | 3,067.5 | 1 | 1,728.1 | 131,333 | 6,064 |
| 4 | 1,388 | 105,540 | 7,129.5 | 4 | 1,367.8 | 103,953 | 9,486 |

TABLE 10A

IL-8 (AGITATION)

| | RUN 1 | | | | RUN 2 | | |
|---|---|---|---|---|---|---|---|
| Time (hr) | pg/mL whole blood | pg/15 mL whole blood | pg per g sorbent | Time (hr) | pg/mL whole blood | pg/15 mL whole blood | pg per g sorbent |
| 0 | 1,955.3 | 29,329 | — | 0 | 2,054 | 30,809 | — |
| 1 | 1,204.8 | 18,072 | 7,125 | 1 | 1,432 | 21,481 | 5,904 |
| 4 | 837.1 | 12,556 | 10,615 | 4 | 734 | 11,010 | 12,531 |

TABLE 11

IL-10 (EXTRACORPOREAL CIRCUIT)

| | RUN 1 | | | | RUN 2 | | |
|---|---|---|---|---|---|---|---|
| Time (hr) | pg/mL whole blood | pg/76 mL whole blood | pg per g sorbent | Time (hr) | pg/mL whole blood | pg/76 mL whole blood | pg per g sorbent |
| 0 | 3,004 | 228,304 | — | 0 | 2,381.8 | 181,017 | — |
| 1 | 997 | 75,772 | 19,066 | 1 | 675.7 | 51,353 | 16,208 |
| 4 | 343.8 | 26,129 | 25,272 | 4 | 169.5 | 12.882 | 21,017 |

TABLE 11A

IL-10 (AGITATION)

| | RUN 1 | | | | RUN 2 | | |
|---|---|---|---|---|---|---|---|
| Time (hr) | pg/mL whole blood | pg/15 mL whole blood | pg per g sorbent | Time (hr) | pg/mL whole blood | pg/15 mL whole blood | pg per g sorbent |
| 0 | 3,214 | 48,210 | — | 0 | 3,240 | 48,600 | — |
| 1 | 1,767.6 | 26,514 | 13,732 | 1 | 1,751.1 | 26,266 | 14,135 |
| 4 | 723.2 | 10,848 | 23,647 | 4 | 621.2 | 9,318 | 24,862 |

TABLE 12

IL-1β (EXTRACORPOREAL CIRCUIT)

| | RUN 1 | | | | RUN 2 | | |
|---|---|---|---|---|---|---|---|
| Time (hr) | pg/mL whole blood | pg/76 mL whole blood | pg per g sorbent | Time (hr) | pg/mL whole blood | pg/76 mL whole blood | pg per g sorbent |
| 0 | 154.52 | 11,743.5 | — | 0 | 150.65 | 11,449 | — |
| 1 | 84.98 | 6,458.5 | 660 | 1 | 88.84 | 6,752 | 587.1 |
| 4 | 0 | 0 | 1,467.9 | 4 | 0 | 0 | 1,431.1 |

TABLE 12A

IL-1β (AGITATION)

| | RUN 1 | | | | RUN 2 | | |
|---|---|---|---|---|---|---|---|
| Time (hr) | pg/mL whole blood | pg/15 mL whole blood | pg per g sorbent | Time (hr) | pg/mL whole blood | pg/15 mL whole blood | pg per g sorbent |
| 0 | 118.98 | 1,784.7 | — | 0 | 122.06 | 1,831.02 | — |
| 1 | 42.58 | 638.71 | 725 | 1 | 50.75 | 761.20 | 677.1 |
| 4 | 7.72 | 115.8 | 1,056.2 | 4 | 4.63 | 69.53 | 1,114.8 |

TABLE 13

Nitric Oxide (NO = $NO_2$ + $NO_3$) (EXTRACORPOREAL CIRCUIT)

| RUN 1 Time (hr) | uM whole blood | % decrease |
|---|---|---|
| 0 | 255.4 | — |
| 1 | 0.501 | 95.0 |
| 4 | 0.000- | 100 |

TABLE 13A

Nitric Oxide (NO = $NO_2$ + $NO_3$) (AGITATION)

| RUN 1 Time (hr) | uM whole blood | % decrease |
|---|---|---|
| 0 | 252.3 | — |
| 1 | 100.9 | 60.0 |
| 4 | 35.7 | 85.8 |

TABLE 14

Hydrogen Peroxide (H$_2$O$_2$) (EXTRACORPOREAL CIRCUIT)

| RUN 1 Time (hr) | nM whole blood | % decrease |
|---|---|---|
| 0 | 235.7 | — |
| 1 | 85.8 | 63.6 |
| 4 | 27.9 | 88.2 |

TABLE 14A

Hydrogen Peroxide (H$_2$O$_2$) (AGITATION)

| RUN 1 Time (hr) | nM whole blood | % decrease |
|---|---|---|
| 0 | 9.70 | — |
| 1 | 0.157 | 92.2 |
| 4 | 0.000- | 100 |

Example Seven

The removal of selected mediators of autoimmune, SIRS-like disorders, neoplastic disorders and physiologic parameters using the compositions and methodologies disclosed herein were investigated. De-watered SCP 125 and 250, AER and CER (in weight proportions: 50%. 20%. 20%, 10%, respectively) in sterile (pharmaceutical grade) forms, were tested for the removal of selected target molecules in autoimmune, SIRS-like and neoplastic conditions. After packing, the chromatographic material was primed with 1% LMW Dextran 40 in 0.9% NaCl. Then the column was connected with the extracorporeal circuit filled with spiked human blood plasma. The extracorporeal whole blood cleansing was conducted for 4 hours. Samples were collected at 0, 1 and 4 hrs and subjected for analyses, as described in previous Examples. Additionally, physiologic parameters were established using Abaxis Piccolo Xpress Chemistry Analyzer and IRMA TruPoint Blood Analysis System. The results of these analyses are presented in Table 15. The results demonstrate adsorbents formulation, which contains SCP/AER/CER, was effective in removal of all investigated mediators of autoimmune, SIRS-like and neoplastic diseases. The effect on physiological mediators was minimal.

TABLE 15

SELECTED DISEASE MEDIATORS (expressed per gram dewatered weight)

| PARAMETER | 36X scaled down circuit; 4 adsorbents column (SCP/AER/CER) Run # 1 | | | 36X scaled down circuit; 4 adsorbents column (SCP/AER/CER) Run # 1 | | |
|---|---|---|---|---|---|---|
| | Baseline | 1 hr | 4 hr | Baseline | 1 hr | 4 hr |
| TNF α (pg/mL) | 981 | 82.98 | 40.1 | — | — | — |
| TNF α (pg/g adsorbent) | 0 | 8,531.2 | 8,938.5 | — | — | — |
| IL-6 (pg/mL) | 312.07 | 67.3 | 53.0 | 293.1 | 45.1 | 37.6 |
| IL-6 (pg/g adsorbent) | 0 | 2,325.3 | 2,461.2 | 0 | 2,356 | 2,427.2 |
| IL-8 (pg/mL) | 111.26 | 49.34 | 46.32 | 106.2 | 67.96 | 63.58 |
| IL-8 (pg/g adsorbent) | 0 | 585.4 | 617 | 0 | 283.3 | 404.9 |
| IL-10 (pg/mL) | 148.5 | 45.76 | 21.72 | 189.6 | 46.92 | 37.6 |
| IL-10 (pg/g adsorbent) | 0 | 976.0 | 1,204.4 | 0 | 1,355.5 | 1,444 |
| TGF β 1 (pg/mL) | 775.3 | 40.0 | 0.0 | 869.2 | 16.7 | 0.0 |
| TGF β 1 (pg/g adsorbent) | 0 | 6,985 | 7,365 | 0 | 8.098 | 8,257 |
| Endotoxin (EU/mL) | 0.655 | 0.138 | 0.040 | 0.943 | 0.204 | 0.103 |
| Endotoxin (EU/g adsorbent) | 0 | 4.91 | 5.84 | 0 | 7.02 | 7.98 |
| Albumin (g/dL) | 1.1 | 1.6 | 1.7 | 1.1 | | |
| ALT (U/L) | 8 | 8 | <5 | 9 | | |
| Amylase (U/L) | <5 | <5 | <5 | <5 | <5 | <5 |
| Calcium (mg/dL) | <4.0 | <4.0 | <4.0 | <4.0 | <4.0 | <4.0 |
| PHOS (mg/dL) | 3.8 | 4.7 | 4.4 | 3.6 | 4.7 | 4.4 |
| Glucose (mg/dL) | 11 | 21 | 21 | <10 | 21 | 21 |
| Sodium (mmol/L) | 148 | 145 | 146 | 146 | 145 | 146 |
| Potassium (mmol/L) | 3.9 | 4.1 | 4.2 | 2.8 | 4.1 | 4.2 |
| Total Protein (g/dL) | 2.7 | 3.1 | 3.0 | 2.7 | 3.1 | 3.0 |

Example Eight

This study, which received clearance from the TTUHSC IACUC (Protocol No. 13003), was designed to investigate the safety of the treatment with adsorption devices of the type disclosed herein in a dog model. Experimental animals underwent a six-hour extracorporeal treatment with devices containing SCP alone or 4 adsorbents: SCP—synthetic carbon 125 and 250, AER—Q Media and CER—S Media used in de-watered weight proportions: 50%. 20%. 20%, 10%, respectively. The adsorption devices were sterile, pyrogen free and highly hemo-biocompatible.

The animal study was designed to obtain information about clinical performance of the adsorption devices in healthy anesthetized dogs. This study determined the effect of the adsorption devices over 6 hours on: (1) hemodynamics; (2) hematologic parameters; (3) analytical blood chemistry parameters; and (4) anatomo-histopathology. Data were collected at:

(i) baseline after induction of anesthesia/catheter placement & prior to the extracorporeal treatment. Baseline laboratory consisted of: AST, ALT, LD, ALP, Albumin, Globulins, Ammonia, lactic acid, total protein, bilirubin, pH, $pO_2$, $pCO_2$, $Na^+$, $K^+$, $Cl^+$, $iCa^{++}$, tCa, $TCO_2$, $HCO_3$, BEb, BEecf, tCa, Mg, BUN and Creatinine, Glucose, complete blood count (Hg, Hct, RBC, WBC, differential, and platelets), coagulation panel: aPTT, PT, INR, D-Dimer and fibrinogen, hemodynamic monitoring; vital signs Q15 min/hemodynamics Q30 min (blood pressure—Mean, Systolic/Diastolic, oxygen saturation & temperature); hemodynamics (PAP, PCWP, CVP, CO, PVR & SVR), and urinary output, (ii) during the treatment at: 30 min, 60 min, 120 min, 180 min, 240 min, 300 min, and 360 min (some parameters, including hemodynamics were also measured at 15 minutes, 90 min and 150 min), AST, ALT, LD, ALP, Albumin, Ammonia, lactic acid, total protein, pH, $pO_2$, $pCO_2$, $Na^+$, $K^+$, $Cl^-$, $iCa^{++}$, tCa, $TCO_2$, $HCO_3$, BEb, BEecf, tCa, Mg, BUN and Creatinine, Glucose, complete blood count (Hg, Hct, RBC, WBC, differential, and platelets), coagulation panel: aPTT, PT, INR, D-Dimer and fibrinogen, hemodynamic monitoring; vital signs Q15 min/hemodynamics Q30 min (blood pressure—M, S/D, oxygen saturation & temperature); hemodynamics (PAP, PCWP, CVP, CO, PVR & SVR), and urinary output (iii) post treatment necropsy and histopathological evaluation (H&E) of lung, liver, kidney, heart and GI tract.

Regulatory Standards
Animals: USDA standards (Marshall, N.Y.)
Animal housing at TTUHSC LARC: GLP standards
Extracorporeal Treatment: Research standards with GLP elements
Hemodynamics: Research standards with GLP elements
Analytical Chemistry: GLP & CLIA standards
Histopathology: GLP & CLIA standards
Equipment Used:
  (i) Continuous Cardiac Output Computer: Q2™ Plus CCO/$SO_2$ Monitoring Systems with $SvO_2$/CCO Swan-Ganz Catheter (HOSPIRA/ICU Medical, Inc.);
  (ii) Multi Parameter SurgiVet Advisor® Vital Signs Monitor (Smiths Medical),
  (iii) MEDICA Dialysis System (MEDICA),
  (iv) Hematology Analyzer VetScan HM5 (Abaxis)
  (v) Chemistry Analyzer VS2 (Abaxis)
  (vi) Chemistry Analyzer Piccolo Xpress (Abaxis),
  (vii) IRMA TruPoint Blood Analysis System (ITC),
  (viii) Blood CO-Oximeter 682 (Instrumentation Laboratory),
  (ix) Chemistry Analyzer COBAS (Roche),
  (x) Coagulation Analyzer (Roche).
Priming Solution: 10% LMW Dextran 40 in 0.9% Sodium Chloride Injection, Hospira, Inc. NDC 0409-7419-03, Lot No. 25-104-JT
I.V. Fluids: Normosol R, pH 7.4, Hospira, Inc., NDC 0409-7670-09, Lot No. 27-904-FW;
  Lactated Ringer's Injection USP, Braun, NDC 0264-7750-30, Lot No. J3P532; 0.9% Sodium Chloride Injection, USP, BAXTER, NDC 0338-0049-04, Lot No. C920132.

The recording of all hemodynamic parameters allowed a comprehensive evaluation of the hemodynamic effects of the adsorbing devices. Results are presented in Tables 17-31. A careful analysis of these parameters illustrates that the adsorbing devices did not cause any significant changes in MAP, CVP, PCWP, PAP, SVR and PVR. The hypovolemic effect observed at late time intervals could be due to fluid management as a part of extracorporeal treatment. Overall, the hemodynamic data may lead to the conclusion that six hour extracorporeal treatment with the adsorbing devices was well tolerated by dogs, regardless of sorbent compositions. The laboratory data suggest that the adsorbing devices, when used in a six hour extracorporeal treatment did not produce any significant pathological reactions. These devices appear to have no effect on vital organs (enzymes), blood cells (RBC, WBC, lymphocytes, neutrophils, eosinophils, monocytes), and coagulation factors. All adsorbing devices produced no disturbances in water, electrolyte and minerals. The adsorbing devices did not produce poor tissue oxygenation nor tissue hypoxia. All other tested parameters were within the normal ranges, regardless of sorbent device compositions. No histopathological abnormalities were noted in vital organs (heart, lungs, liver, kidneys, GI tract).

TABLE 16

Hemodynamic Data
Device with SCP Animal Study Data—Dog No. 1—ID #: 931055

|  | Baseline (min) | 15 | 30 | 60 | 90 | 120 | 150 | 180 | 210 | 240 | 270 | 300 | 330 | 360 |
|---|---|---|---|---|---|---|---|---|---|---|---|---|---|---|
| HR (b/min) | 100 | 102 | 100 | 100 | 100 | 95 | 95 | 94 | 94 | 93 | 82 | 96 | 95 | 95 |
| BP-S/D (mm Hg) | 117/78 | 120/80 | 118/78 | 126/73 | 115/63 | 119/65 | 109/65 | 104/67 | 102/68 | 100/68 | 98/55 | 86/45 | 88/50 | 88/50 |
| BP-M (mm Hg) | 91 | 88 | 89 | 92 | 81 | 83 | 82 | 82 | 78 | 72 | 73 | 60 | 64 | 65 |

TABLE 16-continued

Hemodynamic Data
Device with SCP Animal Study Data—Dog No. 1—ID #: 931055

|  | Baseline (min) | 15 | 30 | 60 | 90 | 120 | 150 | 180 | 210 | 240 | 270 | 300 | 330 | 360 |
|---|---|---|---|---|---|---|---|---|---|---|---|---|---|---|
| CVP (mm Hg) | 4 | 4 | 4 | 6/5 | 6 | 7 | 11 | 13 | 13 | 13 | 12 | 14 | 13 | 13 |
| PA-S/D (mm Hg) | 26/3 | 26/3 | 28/4 | 29/4 | 27/5 | 24/10 | 25/13 | 27/14 | 30/15 | 31/17 | 27/13 | 27/13 | 27/12 | 26/12 |
| PA-M (mm Hg) | 10.7 | 10.7 | 12 | 12.3 | 12.3 | 14.7 | 17 | 18.3 | 20 | 21.7 | 17.7 | 17.7 | 17 | 16.7 |
| PCWP (mm Hg) | 8 | 8 | 8 | 7 | 7 | 3 | 9 | 9 | 9 | 11 | 8 | 9 | 8 | 9 |
| CO (L/min) | 4.8 | 4.8 | 5.6 | 7.3/5.6 | 5.6 | 4.1 | 4.6 | 3.6 | 3.8 | 4.1 | 6.0 | 4.5 | 4.0 | 3.8 |
| PVR (dyne s cm$^{-5}$) | 45 | 45 | 57.1 | 53.7 | 75.7 | 228.3 | 139.1 | 206.6 | 231.6 | 208.8 | 129.3 | 154.7 | 180 | 162.1 |
| SVR (dyne s cm$^{-5}$) | 1448 | 1398 | 1213 | 1152 | 1156 | 1481 | 1233 | 1531 | 1367 | 1150 | 812 | 817 | 1019 | 1093 |
| Urine Output (mL) | 150 | 0 | 0 | 0 | 0 | 0 | 12 | 0 | 0 | 0 | 145 | 0 | 0 | 0 |

TABLE 17

Device with SCP/AER/CER
Animal Study Data - Dog No. 2 - ID #: 924881

|  | Baseline (min) | 15 | 30 | 60 | 90 | 120 | 150 | 180 | 210 | 240 | 270 | 300 | 330 | 360 |
|---|---|---|---|---|---|---|---|---|---|---|---|---|---|---|
| HR (b/min) | 98 | 96 | 93 | 93 | 92 | 90 | 90 | 89 | 90 | 87 | 89 | 90 | 77 | 82 |
| BP - S/D (mmHg) | 94/52 | 110/54 | 110/58 | 118/65 | 115/60 | 105/53 | 103/53 | 105/46 | 105/53 | 109/53 | 95/48 | 102/43 | 107/53 | 118/58 |
| BP - M (mmHg) | 65 | 90 | 75 | 85 | 78 | 64 | 68 | 64 | 70 | 71 | 61 | 61 | 72 | 79 |
| CVP (mmHg) | 5 | 4 | 2 | 5 | 10 | 10 | 10 | 10 | 8 | 10 | 13 | 13 | 13 | 13 |
| PA - S/D (mmHg) | 34/18 | 27/8 | 24/8 | 22/7 | 30/18 | 24/14 | 24/14 | 29/17 | 24/14 | 29/18 | 25/16 | 31/20 | 32/22 | 28/18 |
| PA - M (mmHg) | 23.3 | 14.3 | 13.3 | 12 | 22 | 17.3 | 17.3 | 21 | 17.3 | 21.7 | 19 | 23.7 | 25.3 | 21.3 |
| PCWP (mmHg) | Not recorded | For PVR: arbitrary: 10 | — | — | — | — | — | — | — | — | — | — | — | — |
| CO (L/min) | 4.1 | 5.8 | 4.1 | 4.0 | 4.0 | 3.9 | 4.3 | 4.3 | 3.8 | 3.9 | 3.7 | 3.9 | 4.5 | 4.0 |
| PVR (dyne s cm$^{-5}$) | 259 | 59.3 | 64.4 | 40 | 240 | 149.7 | 135.8 | 204.6 | 153.7 | 240 | 194.6 | 266.7 | 272 | 226 |
| SVR (dyne s cm$^{-5}$) | 1169 | 1171 | 1364 | 1598 | 1358 | 1106 | 1077 | 1096 | 1303 | 1250 | 1144 | 983 | 1047 | 1318 |
| Urine Output (mL) | 60 | 0 | 20 | 15 | 23 | 10 | 15 | 10 | 15 | 17 | 7 | 23 | 10 | 34 |

TABLE 18

BLOOD CHEMISTRY & HEMATOLOGICAL EVALUATION
Device with ACM. Animal Study Data - Dog No. 1 - ID #: 931055

|  | Baseline (min) | 15 | 30 | 60 | 90 | 120 | 150 | 180 | 210 | 240 | 270 | 300 | 330 | 360 |
|---|---|---|---|---|---|---|---|---|---|---|---|---|---|---|
| pH (U) | 7.189 | 7.393 | 7.359 | 7.277 | — | 7.251 | 7.520 | 7.360 | — | 7.442 | — | 7.508 | — | 7.431 |
| pCO2 (mmHg) | 41.5 | 41.3 | 42.5 | 53.2 | — | 58.0 | 23.2 | 40.1 | — | 32.9 | — | 27.2 | — | 30.9 |
| pO2 (mmHg) | 183.0 | 432.8 | 421.3 | 383.3 | — | 382.3 | 439.4 | 430.9 | — | 461.7 | — | 323.3 | — | 351.4 |
| Na+ (mM) | 148.1 | 150.9 | 146.9 | 146.2 | — | 147.3 | 149.0 | 145.7 | — | 142.8 | — | 145.8 | — | 144.1 |
| K+ (mM) | 2.52 | 2.97 | 3.08 | — | — | — | 2.78 | — | — | — | — | 3.73 | — | 5.75 |
| iCa++ (mM) | — | 1.41 | 1.33 | 0.2 | — | 0.31 | 1.26 | 0.2 | — | — | — | 1.14 | — | 0.87 |
| HCO3− (mM) | 15.6 | 24.9 | 23.7 | 24.5 | — | 25.2 | 18.7 | 22.4 | — | 22.2 | — | 21.4 | — | 20.4 |
| TCO2 (mM) | 16.9 | 26.2 | 25.0 | 26.2 | — | 27.0 | 19.5 | 23.6 | — | 23.2 | — | 22.2 | — | 21.3 |
| BEb (mM) | −11.5 | 0.5 | −1.2 | −2.4 | — | −2.5 | −1.4 | −2.2 | — | −0.5 | — | 0.4 | — | −2.1 |
| BEecf (mM) | −12.8 | −0.2 | −2.0 | −2.5 | — | −2.2 | −4.3 | −3.3 | — | −2.1 | — | −1.9 | — | −4.1 |
| O2Sat (%) | 98.8 | 99.9 | 99.8 | 99.8 | — | 99.8 | 99.9 | 99.8 | — | 99.9 | — | 99.8 | — | 99.8 |

TABLE 19

BLOOD CHEMISTRY & HEMATOLOGICAL EVALUATION
Device with SCP/AER/CER. Animal Study Data - Dog No. 2 - ID #: 924881

|  | Baseline (min) | 15 | 30 | 60 | 90 | 120 | 150 | 180 | 210 | 240 | 270 | 300 | 330 | 360 |
|---|---|---|---|---|---|---|---|---|---|---|---|---|---|---|
| pH (U) | 7.405 | 7.306 | 7.322 | 7.318 | — | 7.352 | — | 7.405 | — | 7.392 | — | 7.372 | — | 7.380 |
| pCO2 (mmHg) | 31.3 | 39.2 | 47.7 | 47.0 | — | 40.1 | — | 37.0 | — | 41.2 | — | 42.8 | — | 42.9 |
| pO2 (mmHg) | 321.6 | 309.9 | 380.0 | 353.6 | — | 318.9 | — | 168.8 | — | 371.8 | — | 381.7 | — | 388.5 |
| Na+ (mM) | 148.8 | 149.4 | 150.2 | 150.7 | — | 150.4 | — | 147.0 | — | 147.2 | — | 146.7 | — | 146.6 |
| K+ (mM) | 2.93 | 2.68 | 2.84 | 2.78 | — | 2.69 | — | 3.44 | — | 3.20 | — | 3.02 | — | 2.92 |
| iCa++ (mM) | 1.47 | 1.16 | 1.27 | 1.31 | — | 1.22 | — | 1.23 | — | 1.33 | — | 1.36 | — | 1.30 |
| HCO3− (mM) | 19.4 | 19.4 | 24.4 | 23.8 | — | 22.0 | — | 22.9 | — | 24.7 | — | 24.6 | — | 25.1 |
| TCO2 (mM) | 20.3 | 20.6 | 25.9 | 25.3 | — | 23.2 | — | 24.0 | — | 26.0 | — | 25.9 | — | 26.4 |
| BEb (mM) | −3.6 | −5.8 | −1.5 | −2.0 | — | −2.7 | — | −0.8 | — | 0.4 | — | −0.2 | — | 0.4 |
| BEecf (mM) | −5.6 | −7.2 | −1.9 | −2.5 | — | −3.8 | — | −2.0 | — | −0.4 | — | −0.9 | — | −0.3 |
| O2Sat (%) | 99.7 | 99.7 | 99.8 | 99.7 | — | 99.7 | — | 99.1 | — | 99.8 | — | 99.8 | — | 99.8 |

TABLE 20

BLOOD CO-OXIMETRY
Device with SCP. Animal Study Data - Dog No. 1 - ID #: 931055

|  | Baseline (min) | 15 | 30 | 60 | 90 | 120 | 150 | 180 | 210 | 240 | 270 | 300 | 330 | 360 |
|---|---|---|---|---|---|---|---|---|---|---|---|---|---|---|
| THb (g/dL) | 8.2 | 11.3 | 8.9 | 10.1 | — | 10.0 | — | 9.9 | — | 9.5 | — | 9.6 | — | 9.4 |
| OxyHb (%) | 90.0 | 92.3 | 90.4 | 90.3 | — | 90.2 | — | 90.4 | — | 90.2 | — | 90.9 | — | 90.2 |

TABLE 20-continued

BLOOD CO-OXIMETRY
Device with SCP. Animal Study Data - Dog No. 1 - ID #: 931055

| | Baseline (min) | 15 | 30 | 60 | 90 | 120 | 150 | 180 | 210 | 240 | 270 | 300 | 330 | 360 |
|---|---|---|---|---|---|---|---|---|---|---|---|---|---|---|
| COHb (%) | 9.8 | 4.7 | 10.1 | 10.1 | — | 10.1 | — | 10.1 | — | 10.3 | — | 10.5 | — | 10.0 |
| MetHb (%) | 0.5 | 2.3 | 0.5 | 0.4 | — | 0.4 | — | 0.5 | — | 0.4 | — | 0.4 | — | 0.5 |
| RHb (Reduced Hb - %) | −0.4 | 0.8 | −1.0 | −0.8 | — | −0.7 | — | −1.0 | — | −1.0 | — | −1.0 | — | −0.7 |
| O2 Content (mL/dL) | 10.3 | 14.5 | 11.2 | 12.7 | — | 12.5 | — | 12.4 | — | 11.9 | — | 12.0 | — | 11.8 |
| O2 Capacity (mL/dL) | 10.2 | 14.6 | 11.1 | 12.6 | — | 12.4 | — | 12.3 | — | 11.8 | — | 11.9 | — | 11.7 |

TABLE 21

BLOOD CHEMISTRY & HEMATOLOGICAL EVALUATION
Device with SCP/AER/CER. Animal Study Data - Dog No. 2 - ID #: 924881

| | Baseline (min) | 15 | 30 | 60 | 90 | 120 | 150 | 180 | 210 | 240 | 270 | 300 | 330 | 360 |
|---|---|---|---|---|---|---|---|---|---|---|---|---|---|---|
| THb (g/dL) | 9.8 | — | 12.1 | 12.0 | — | 9.8 | — | 10.3 | — | 9.9 | — | 10.4 | — | 8.9 |
| OxyHb (%) | 90.4 | — | 90.2 | 90.4 | — | 90.9 | — | 89.9 | — | 90.4 | — | 90.5 | — | 89.6 |
| COHb (%) | 9.9 | — | 10.0 | 9.8 | — | 10.1 | — | 9.1 | — | 9.7 | — | 10.0 | — | 9.7 |
| MetHb (%) | 0.5 | — | 0.5 | 0.5 | — | −0.3 | — | 0.9 | — | 0.5 | — | 0.4 | — | 0.9 |
| RHb (Reduced Hb - %) | −0.7 | — | −0.7 | −0.7 | — | −0.7 | — | 0.1 | — | −0.6 | — | −0.9 | — | −0.2 |
| O2 Content (mL/dL) | 12.3 | — | 15.2 | 15.0 | — | 12.4 | — | 12.9 | — | 12.4 | — | 13.1 | — | 11.1 |
| O2 Capacity (mL/dL) | 12.2 | — | 15.1 | 15.0 | — | 12.3 | — | 12.9 | — | 12.4 | — | 13.0 | — | 11.1 |

TABLE 22

BLOOD CHEMISTRY - BASIC METABOLIC PANEL PLUS Device with SCP. Animal Study Data - Dog No. 1 - ID #: 931055

| | Baseline (min) | 15 | 30 | 60 | 90 | 120 | 150 | 180 | 210 | 240 | 270 | 300 | 330 | 360 |
|---|---|---|---|---|---|---|---|---|---|---|---|---|---|---|
| Sodium mmol/L (128-145) | 157 | — | 138 | 147 | — | 148 | — | 146 | — | 151 | — | 140 | — | 145 |
| Potassium mmol/L (3.6-5.1) | 2.5 | — | 3.0 | — | — | 3.0 | — | — | — | — | — | 3.7 | — | — |
| Chloride mmol/L (98-108) | 118 | — | 113 | 110 | — | 108 | — | 107 | — | 110 | — | 111 | — | 111 |
| Total CO2 mmol/L (18-33) | 14 | — | 24 | 26 | — | 26 | — | 23 | — | 23 | — | 23 | — | 21 |
| BUN mg/dL (7-22) | 14 | — | 18 | 19 | — | 18 | — | 17 | — | 17 | — | 16 | — | 16 |
| Glucose mg/dL (73-118) | 89 | — | 110 | 129 | — | 132 | — | 125 | — | 119 | — | 127 | — | 118 |

TABLE 22-continued

BLOOD CHEMISTRY - BASIC METABOLIC PANEL PLUS Device with SCP. Animal Study Data - Dog No. 1 - ID #: 931055

|  | Baseline (min) | 15 | 30 | 60 | 90 | 120 | 150 | 180 | 210 | 240 | 270 | 300 | 330 | 360 |
|---|---|---|---|---|---|---|---|---|---|---|---|---|---|---|
| Total Calcium mg/dL (8.0-10.3) | 4.0 | — | 5.9 | 4.0 | — | 4.0 | — | 4.0 | — | 4.0 | — | 4.0 | — | 4.0 |
| Magnesium mg/dL (1.6-2.3) | 0.2 | — | 1.2 | 0.7 | — | 0.7 | — | 0.6 | — | 0.5 | — | 1.2 | — | 0.7 |
| Lactate Dehydrogenase U/L (99-192) | 60 | — | 66 | 75 | — | 185 | — | 11 | — | 107 | — | 133 | — | 168 |

TABLE 23

BLOOD CHEMISTRY - BASIC METABOLIC PANEL PLUS Animal Study Data - Dog No. 2 - ID #: 924881

|  | Baseline (min) | 15 | 30 | 60 | 90 | 120 | 150 | 180 | 210 | 240 | 270 | 300 | 330 | 360 |
|---|---|---|---|---|---|---|---|---|---|---|---|---|---|---|
| Sodium mmol/L (128-145) | 141 | — | 137 | 137 | — | 136 | — | 138 | — | 136 | — | 135 | — | 137 |
| Potassium mmol/L (3.6-5.1) | 3.0 | — | 2.9 | 3.0 | — | 2.9 | — | 3.4 | — | 3.3 | — | 3.1 | — | 3.2 |
| Chloride mmol/L (90-108) | 110 | — | 111 | 112 | — | 114 | — | 111 | — | 112 | — | 110 | — | 109 |
| Total CO2 mmol/L (18-33) | 20 | — | 25 | 25 | — | 23 | — | 26 | — | 26 | — | 26 | — | 27 |
| BUN mg/dL (7-22) | 14 | — | 14 | 14 | — | 12 | — | 11 | — | 12 | — | 11 | — | 11 |
| Glucose mg/dL (73-118) | 150 | — | 156 | 166 | — | 146 | — | 168 | — | 167 | — | 175 | — | 164 |
| Total Calcium mg/dL (8.0-10.3) | 10.2 | — | 7.5 | 8.2 | — | 7.1 | — | 7.8 | — | 8.1 | — | 8.0 | — | 8.1 |
| Magnesium mg/dL (1.6-2.3) | 1.6 | — | 1.4 | 1.5 | — | 1.3 | — | 1.6 | — | 1.6 | — | 1.6 | — | 1.7 |
| Lactate Dehydrogenase U/L (99-192) | 195 | — | 96 | 128 | — | 97 | — | 69 | — | 54 | — | 73 | — | 76 |

TABLE 24

BLOOD CHEMISTRY - COMPREHENSIVE DIAGNOSTIC PROFILE Device with SCP. Animal Study Data - Dog No. 1 - ID #: 931055

|  | Baseline (min) | 15 | 30 | 60 | 90 | 120 | 150 | 180 | 210 | 240 | 270 | 300 | 330 | 360 |
|---|---|---|---|---|---|---|---|---|---|---|---|---|---|---|
| Albumin g/dL (2.5-4.4) | 1.5 | — | 1.5 | 1.6 | — | 1.6 | — | 1.6 | — | 1.4 | — | 1.4 | — | 1.4 |
| ALP U/L (20-150) | 9 | — | 32 | 41 | — | 45 | — | 46 | — | 40 | — | 57 | — | 44 |

TABLE 24-continued

BLOOD CHEMISTRY - COMPREHENSIVE DIAGNOSTIC PROFILE
Device with SCP. Animal Study Data - Dog No. 1 - ID #: 931055

| | Baseline (min) | 15 | 30 | 60 | 90 | 120 | 150 | 180 | 210 | 240 | 270 | 300 | 330 | 360 |
|---|---|---|---|---|---|---|---|---|---|---|---|---|---|---|
| ALT U/L (10-118) | 19 | — | 25 | 24 | — | 15 | — | 16 | — | 26 | — | 23 | — | 22 |
| Amylase U/L (200-1200) | 519 | — | 529 | 552 | — | 551 | — | 536 | — | 495 | — | 565 | — | 520 |
| BUN mg/dL (7-25) | 14 | — | 18 | 19 | — | 18 | — | 18 | — | 17 | — | 17 | — | 15 |
| Total Calcium mg/dL (8.6-11.8) | 4.0 | — | 5.0 | 4.0 | — | 4.0 | — | 4.0 | — | 4.0 | — | 4.0 | — | 1.9 |
| Phosphorus mg/dL (2.9-6.6) | 4.0 | — | 5.7 | 6.3 | — | 5.9 | — | 5.3 | — | 4.6 | — | 4.5 | — | 4.4 |
| Glucose mg/dL (60-110) | 87 | — | 107 | 124 | — | 130 | — | 124 | — | 117 | — | 121 | — | 116 |
| Sodium mmol/L (138-160) | 157 | — | 140 | 148 | — | 149 | — | 147 | — | 153 | — | 144 | — | 151 |
| Potassium mmol/L (3.7-5.8) | 2.5 | — | 5.4 | — | — | 3.0 | — | — | — | — | — | 3.7 | — | — |
| Total Protein g/dL (5.4-8.2) | 3.1 | — | 3.5 | 3.7 | — | 3.7 | — | 3.5 | — | 3.2 | — | 3.4 | — | 3.3 |

TABLE 25

BLOOD CHEMISTRY - COMPREHENSIVE DIAGNOSTIC PROFILE
Device with SCP/AER/CER. Animal Study Data - Dog No. 2 - ID #: 924881

| | Baseline (min) | 15 | 30 | 60 | 90 | 120 | 150 | 180 | 210 | 240 | 270 | 300 | 330 | 360 |
|---|---|---|---|---|---|---|---|---|---|---|---|---|---|---|
| Albumin g/dL (2.5-4.4) | 1.6 | — | 1.6 | 1.6 | — | 1.2 | 1.2 | 1.2 | — | 1.3 | — | 1.4 | — | 1.3 |
| ALP U/L (20-150) | 35 | — | 36 | 36 | — | 39 | 39 | 40 | — | 48 | — | 46 | — | 53 |
| ALT U/L (10-118) | 12 | — | 14 | 10 | — | 11 | 11 | 13 | — | 14 | — | 15 | — | 14 |
| Amylase U/L (200-1200) | 367 | — | 381 | 393 | — | 338 | 334 | 369 | — | 401 | — | 417 | — | 402 |
| BUN mg/dL (7-25) | 13 | — | 14 | 13 | — | 11 | 11 | 12 | — | 12 | — | 11 | — | 10 |
| Total Calcium mg/dL (8.6-11.8) | 7.1 | — | 7.9 | 8.0 | — | 6.9 | 7.0 | 7.3 | — | 8.0 | — | 7.9 | — | 7.8 |
| Phosphorus mg/dL (2.9-6.6) | 5.2 | — | 6.4 | 6.1 | — | 5.2 | 5.7 | 6.0 | — | 5.7 | — | 5.3 | — | 5.1 |
| Glucose mg/dL (60-110) | 135 | — | 151 | 161 | — | 144 | 142 | 165 | — | 165 | — | 172 | — | 163 |
| Sodium mmol/L (138-160) | 139 | — | 139 | 139 | — | 139 | 139 | 138 | — | 138 | — | 138 | — | 139 |
| Potassium mmol/L (3.7-5.8) | 2.3 | — | 2.5 | 2.5 | — | 2.3 | 2.2 | 3.2 | — | 3.0 | — | 3.0 | — | 2.6 |

TABLE 25-continued

BLOOD CHEMISTRY - COMPREHENSIVE DIAGNOSTIC PROFILE
Device with SCP/AER/CER. Animal Study Data - Dog No. 2 - ID #: 924881

| | Baseline (min) | 15 | 30 | 60 | 90 | 120 | 150 | 180 | 210 | 240 | 270 | 300 | 330 | 360 |
|---|---|---|---|---|---|---|---|---|---|---|---|---|---|---|
| Total Protein g/dL (5.4-8.2) | 3.1 | — | 3.1 | 3.1 | — | 2.6 | 2.6 | 2.7 | — | 2.7 | — | 2.7 | — | 2.7 |

TABLE 26

COAGULATION PANEL
Device with SCP. Animal Study Data - Dog No. 1 - ID #: 931055

| | Baseline (min) | 15 | 30 | 60 | 90 | 120 | 150 | 180 | 210 | 240 | 270 | 300 | 330 | 360 |
|---|---|---|---|---|---|---|---|---|---|---|---|---|---|---|
| PT sec (9.3-12.1) | 7.4 | — | 9.2 | 8.6 | — | 8.6 | — | 8.6 | — | 8.6 | — | 8.8 | — | 9.1 |
| International Normalized Ratio (INR) | 0.66 | — | 0.82 | 0.77 | — | 0.77 | — | 0.76 | — | 0.77 | — | 0.79 | — | 0.81 |
| PTT sec (26.1-37.9) | 22.8 | 149.5 | 117.3 | 81.6 | 68.7 | 143.7 | 111.4 | 69.8 | 74.9 | 48.1 | 43.0 | 103.8 | 88.0 | 86.2 |
| Fibrinogen mg/dL (197-406) | 158.0 | — | 94.0 | 100.0 | — | 112.0 | — | 108.0 | — | 102.0 | — | 102.0 | — | 105.0 |
| D-Dimer ng/mL (0-243) | <150 | — | <150 | <150 | — | <150 | — | <150 | — | <150 | — | <150 | — | <150 |

TABLE 27

COAGULATION PANEL
Device with SCP/AER/CER. Animal Study Data - Dog No. 2 - ID #: 924881

| | Baseline (min) | 15 | 30 | 60 | 90 | 120 | 150 | 180 | 210 | 240 | 270 | 300 | 330 | 360 |
|---|---|---|---|---|---|---|---|---|---|---|---|---|---|---|
| PT sec (9.3-12.1) | 8.4 | — | 9.8 | 9.4 | — | 11.9 | — | 13.7 | — | 13.1 | — | 12.7 | — | 15.0 |
| International Normalized Ratio (INR) | 0.75 | — | 0.88 | 0.84 | — | 1.07 | — | 1.24 | — | 1.19 | — | 1.15 | — | 1.36 |
| PTT sec (26.1-37.9) | 178.0 | >400 | 216.4 | 101.7 | >400 | 217.0 | 237.6 | 187.3 | 145.6 | 197.4 | 156.6 | >400 | 311.0 | 211.5 |
| Fibrinogen mg/dL (197-406) | 56.0 | — | 78.0 | 57.0 | — | 54.0 | — | 51.0 | — | 56.0 | — | 55.0 | — | 52.0 |
| D-Dimer ng/mL (0-243) | 165 | — | <150 | <150 | — | <150 | — | <150 | — | <150 | — | <150 | — | <150 |

TABLE 28

LACTIC ACID & AMMONIA
Device with SCP. Animal Study Data - Dog No. 1 - ID #: 931055

| | Baseline (min) | 15 | 30 | 60 | 90 | 120 | 150 | 180 | 210 | 240 | 270 | 300 | 330 | 360 |
|---|---|---|---|---|---|---|---|---|---|---|---|---|---|---|
| Lactic Acid mmol/L (0.5-2.2) | 1.9 | — | 1.5 | 1.0 | — | 0.8 | — | 0.9 | — | 0.7 | — | 0.7 | — | 0.6 |

TABLE 28-continued

LACTIC ACID & AMMONIA
Device with SCP. Animal Study Data - Dog No. 1 - ID #: 931055

| | Baseline (min) | 15 | 30 | 60 | 90 | 120 | 150 | 180 | 210 | 240 | 270 | 300 | 330 | 360 |
|---|---|---|---|---|---|---|---|---|---|---|---|---|---|---|
| Ammonia mcmol/L (56-92) | 15 | — | 15 | 15 | — | 23 | — | 27 | — | 15 | — | 11 | — | 15 |

TABLE 29

LACTIC ACID & AMMONIA
Device with SCP/AER/CER. Animal Study Data - Dog No. 2 - ID #: 924881

| | Baseline (min) | 15 | 30 | 60 | 90 | 120 | 150 | 180 | 210 | 240 | 270 | 300 | 330 | 360 |
|---|---|---|---|---|---|---|---|---|---|---|---|---|---|---|
| Lactic Acid mmol/L (0.5-2.2) | 3.2 | — | 2.5 | 2.5 | — | 1.3 | — | 1.1 | — | — | — | 1.1 | — | 1.3 |
| Ammonia mcmol/L (56-92) | 21 | — | 24 | 27 | — | 11 | — | 14 | — | — | — | 13 | — | 27 |

TABLE 30

HEMATOLOGY
Device with SCP. Animal Study Data - Dog No. 1 - ID #: 931055

| | Baseline (min) | 15 | 30 | 60 | 90 | 120 | 150 | 180 | 210 | 240 | 270 | 300 | 330 | 360 |
|---|---|---|---|---|---|---|---|---|---|---|---|---|---|---|
| WBC ($10^9$/L) | 4.18 | — | 2.13 | 2.78 | — | 3.21 | — | 3.09 | — | 3.53 | — | 3.62 | — | 3.30 |
| LYMPH ($10^9$/L) | 0.71 | — | 0.59 | 0.86 | — | 0.88 | — | 0.69 | — | 0.73 | — | 0.81 | — | 0.81 |
| MONO ($10^9$/L) | 0.31 | — | 0.14 | 0.02 | — | 0.21 | — | 0.18 | — | 0.33 | — | 0.22 | — | 0.17 |
| NEUT ($10^9$/L) | 3.15 | — | 1.40 | 1.90 | — | 2.11 | — | 2.22 | — | 2.47 | — | 2.59 | — | 2.32 |
| EOS ($10^9$/L) | 0.00 | — | 0.00 | 0.00 | — | 0.01 | — | 0.00 | — | 0.00 | — | 0.00 | — | 0.00 |
| BASO ($10^9$/L) | 0.00 | — | 0.00 | 0.00 | — | 0.00 | — | 0.00 | — | 0.00 | — | 0.00 | — | 0.00 |
| LYMPH (%) | 17.0 | — | 27.6 | 31.0 | — | 27.5 | — | 22.3 | — | 20.6 | — | 22.3 | — | 24.5 |
| MONO (%) | 7.4 | — | 6.6 | 0.5 | — | 6.5 | — | 5.8 | — | 9.3 | — | 6.0 | — | 5.2 |
| NEUT (%) | 75.5 | — | 65.7 | 68.3 | — | 65.8 | — | 71.8 | — | 70.0 | — | 71.6 | — | 70.1 |
| EOS (%) | 0.1 | — | 0.2 | 0.1 | — | 0.2 | — | 0.0 | — | 0.0 | — | 0.0 | — | 0.1 |
| BASO (%) | 0.0 | — | 0.0 | 0.0 | — | 0.0 | — | 0.0 | — | 0.0 | — | 0.0 | — | 0.0 |
| RBC ($10^{12}$/L) | 4.98 | — | 4.02 | 4.53 | — | 4.46 | — | 4.40 | — | 4.12 | — | 4.31 | — | 4.17 |
| Hb (g/dL) | 11.3 | — | 9.1 | 10.2 | — | 10.0 | — | 9.9 | — | 9.4 | — | 9.6 | — | 9.2 |
| HCT (%) | 32.88 | — | 26.34 | 29.87 | — | 29.65 | — | 29.14 | — | 26.97 | — | 28.14 | — | 27.57 |
| MCV (u) | 66 | — | 66 | 66 | — | 66 | — | 66 | — | 66 | — | 65 | — | 66 |
| MCH (pg) | 22.6 | — | 22.7 | 22.5 | — | 22.5 | — | 22.5 | — | 23.0 | — | 22.3 | — | 22.1 |
| MCHC (g/dL) | 34.2 | — | 34.7 | 34.1 | — | 33.8 | — | 34.0 | — | 35.0 | — | 34.1 | — | 33.5 |
| RDWc (%) | 15.7 | — | 15.9 | 15.7 | — | 15.7 | — | 15.5 | — | 15.3 | — | 15.9 | — | 15.7 |

TABLE 30-continued

HEMATOLOGY
Device with SCP. Animal Study Data - Dog No. 1 - ID #: 931055

|  | Baseline (min) | 15 | 30 | 60 | 90 | 120 | 150 | 180 | 210 | 240 | 270 | 300 | 330 | 360 |
|---|---|---|---|---|---|---|---|---|---|---|---|---|---|---|
| PLT (10^9/L) | 162 | — | 71 | 107 | — | 115 | — | 118 | — | 103 | — | 107 | — | 104 |
| PCT (%) | 0.19 | — | 0.08 | 0.12 | — | 0.14 | — | 0.14 | — | 0.12 | — | 0.13 | — | 0.13 |
| MPV (u) | 11.8 | — | 11.9 | 11.4 | — | 11.9 | — | 12.1 | — | 11.9 | — | 11.9 | — | 12.3 |
| PDWc (%) | 41.0 | — | 40.2 | 37.6 | — | 40.5 | — | 38.7 | — | 39.5 | — | 39.6 | — | 41.7 |

TABLE 31

HEMATOLOGY
Device with SCP/AER/CER. Animal Study Data - Dog No. 2 - ID #: 024881

|  | Baseline (min) | 15 | 30 | 60 | 90 | 120 | 150 | 180 | 210 | 240 | 270 | 300 | 330 | 360 |
|---|---|---|---|---|---|---|---|---|---|---|---|---|---|---|
| WBC (10^9/L) | 3.14 | — | 3.75 | 4.22 | — | 4.04 | — | 4.97 | — | 5.88 | — | 5.82 | — | 6.04 |
| LYMPH (10^9/L) | 0.89 | — | 0.90 | 1.22 | — | 0.87 | — | 0.92 | — | 1.29 | — | 1.02 | — | 1.46 |
| MONO (10^9/L) | 0.18 | — | 0.15 | 0.22 | — | 0.26 | — | 0.27 | — | 0.46 | — | 0.41 | — | 0.42 |
| NEUT (10^9/L) | 2.06 | — | 2.69 | 2.79 | — | 2.91 | — | 3.78 | — | 4.13 | — | 4.39 | — | 4.16 |
| EOS (10^9/L) | 0.01 | — | 0.01 | 0.00 | — | 0.00 | — | 0.00 | — | 0.00 | — | 0.00 | — | 0.00 |
| BASO (10^9/L) | 0.00 | — | 0.00 | 0.00 | — | 0.00 | — | 0.00 | — | 0.00 | — | 0.00 | — | 0.00 |
| LYMPH (%) | 28.3 | — | 24.0 | 28.8 | — | 21.6 | — | 18.4 | — | 22.0 | — | 17.5 | — | 24.2 |
| MONO (%) | 5.7 | — | 4.0 | 5.1 | — | 6.4 | — | 5.4 | — | 7.8 | — | 7.0 | — | 6.9 |
| NEUT (%) | 65.8 | — | 71.8 | 66.0 | — | 72.0 | — | 76.1 | — | 70.2 | — | 75.4 | — | 69.8 |
| EOS (%) | 0.2 | — | 0.1 | 0.1 | — | 0.1 | — | 0.0 | — | 0.0 | — | 0.0 | — | 0.1 |
| BASO (%) | 0.0 | — | 0.0 | 0.0 | — | 0.0 | — | 0.0 | — | 0.0 | — | 0.0 | — | 0.0 |
| RBC (10^12/L) | 4.12 | — | 4.89 | 4.92 | — | 4.06 | — | 4.17 | — | 3.96 | — | 4.29 | — | 3.63 |
| Hb (g/dL) | 9.7 | — | 11.9 | 11.6 | — | 9.5 | — | 9.8 | — | 9.6 | — | 10.3 | — | 8.5 |
| HCT (%) | 28.17 | — | 33.58 | 34.04 | — | 28.13 | — | 28.65 | — | 26.97 | — | 29.73 | — | 24.84 |
| MCV (u) | 68 | — | 69 | 69 | — | 69 | — | 69 | — | 68 | — | 69 | — | 68 |
| MCH (pg) | 23.4 | — | 24.3 | 23.5 | — | 23.3 | — | 23.5 | — | 24.3 | — | 24.1 | — | 23.5 |
| MCHC (g/dL) | 34.3 | — | 35.4 | 33.9 | — | 33.7 | — | 34.2 | — | 35.6 | — | 34.8 | — | 34.3 |
| RDWc (%) | 14.8 | — | 15.0 | 15.2 | — | 14.6 | — | 15.0 | — | 14.6 | — | 14.8 | — | 15.0 |
| PLT (10^9/L) | 113 | — | 152 | 149 | — | 116 | — | 127 | — | 121 | — | 120 | — | 102 |
| PCT (%) | 0.12 | — | 0.17 | 0.16 | — | 0.13 | — | 0.13 | — | 0.13 | — | 0.14 | — | 0.11 |
| MPV (u) | 10.3 | — | 11.0 | 10.7 | — | 11.1 | — | 10.5 | — | 11.1 | — | 11.4 | — | 10.8 |
| PDWc (%) | 36.9 | — | 39.0 | 39.2 | — | 38.9 | — | 38.6 | — | 38.5 | — | 39.8 | — | 38.8 |

The following enumerated embodiments are provided as non-limiting examples.

A first embodiment which is a three component composition for use in the treatment of an autoimmune disease where the first component comprises a bimodal synthetic carbon particle mixture; the second component comprises a bimodal synthetic carbon particle mixture and an anion exchange resin and the third component comprises a bimodal synthetic carbon particle mixture and a cation exchange resin.

A second embodiment which is the three component composition of the first embodiment wherein the components are separated.

A third embodiment which the three component composition of any of the first through second embodiments wherein the bimodal synthetic carbon particle mixture comprises a first carbon particle having pore size x and a second carbon particle having pore size y where y is greater than x.

A fourth embodiment which the three component composition of the third embodiment where y is two times x.

A fifth embodiment which the three component composition of any of the first through fourth embodiments wherein the second component has a ratio of bimodal synthetic carbon particle mixture to anion exchange resin of from about 1:1 to about 5:2.

A sixth embodiment which the three component composition of any of the first through fifth embodiments wherein the third component has a ratio of bimodal synthetic carbon particle mixture to cation exchange resin of from about 1:1 to about 5:1.

A seventh embodiment which the three component composition of any of the first through sixth embodiments wherein the autoimmune disease is rheumatoid arthritis.

An eighth embodiment which the three component composition of any of the first through sixth embodiments wherein the autoimmune disease is diabetes mellitus type I.

A ninth embodiment which the three component composition of any of the first through sixth embodiments wherein the autoimmune disease is inflammatory bowel disease.

A tenth embodiment which the three component composition of any of the first through sixth embodiments wherein the autoimmune disease is systemic lupus erythematosus.

An eleventh embodiment which the three component composition of any of the first through sixth embodiments wherein the autoimmune disease is multiple sclerosis.

A twelfth embodiment which is a method comprising contacting a bodily fluid with the three component composition of any of the first through sixth embodiments, A thirteenth embodiment which is the method of the twelfth embodiment wherein contacting occurs in an extracorporeal apparatus having a first column, a second column, and a third column.

A fourteenth embodiment which is the method of the thirteenth embodiment wherein the first component is disposed within the first column, the second component is disposed within the second column, and the third component is disposed within the third column.

A fifteenth embodiment which is the method of the fourteenth embodiment wherein there is fluid communication between the first and second column.

A sixteenth embodiment which is the method of any of the fourteenth and fifteenth embodiments wherein there is fluid communication between the second and third column.

A seventeenth embodiment which is the method of any of the twelfth through sixteenth embodiments wherein the bodily fluid comprises whole blood.

An eighteenth embodiment which is a three component composition for use in the treatment of a Class A condition where the first component comprises a bimodal synthetic carbon particle mixture; the second component comprises the bimodal synthetic carbon particle mixture and an anion exchange resin in a ratio of from about 10:1 to about 7:3 and the third component comprises the bimodal synthetic carbon particle mixture and a cation exchange resin of from about 10:1 to about 7:3.

A nineteenth embodiment which is the three component composition of the eighteenth embodiment wherein the components are separated.

A twentieth embodiment which is the three component composition of any of the eighteenth through nineteenth embodiments wherein the bimodal synthetic carbon particle mixture comprises a first carbon particle having pore size x and a second carbon particle having pore size y where y is greater than x.

A twenty-first embodiment which is the three component composition of any of the eighteenth through twentieth embodiments wherein x is 125 µm and y is 250 µm.

A twenty-second embodiment which is the three component composition of any of the eighteenth through twenty-first embodiments wherein x is 250 µm and y is 500 µm.

A twenty-third embodiment which is the three component composition of any of the eighteenth through twenty-second embodiments wherein the Class A condition is a neoplastic disorder.

A twenty-fourth embodiment which is the three component composition of any of the eighteenth through twenty-third embodiments wherein the Class A condition is a metabolic disorder.

A twenty-fifth embodiment which is the three component composition of any of the eighteenth through twenty-fourth embodiments wherein the Class A condition is a systemic immune response disorder.

A twenty-sixth embodiment which is the three component composition of any of the eighteenth through twenty-fifth embodiments wherein the Class A condition is hepatic encephalopathy.

A twenty-seventh embodiment which is a method comprising contacting a bodily fluid with the three component composition eighteenth through twenty-second embodiments.

A twenty-eighth embodiment which is the method of the twenty-seventh embodiment wherein contacting occurs in an extracorporeal apparatus having a first column, a second column, and a third column.

A twenty-ninth embodiment which is the method of any of the twenty-seventh through twenty-eighth embodiments wherein the first component is disposed within the first column, the second component is disposed within the second column, and the third component is disposed within the third column.

A thirtieth embodiment which is the method of the twenty-ninth embodiments wherein there is fluid communication between the first and second column.

A thirty-first embodiment which is the method of any of the twenty-ninth through thirtieth embodiments wherein there is fluid communication between the second and third column.

A thirty-second embodiment which is the method of any of the twenty-seventh through thirty-first embodiments wherein the bodily fluid comprises whole blood.

A thirty-third embodiment which is a composition comprising 80 weight percent of a first synthetic carbon particle and 20 weight percent of a second synthetic carbon particle for use in the treatment of an overdose of a drug or poison wherein the first synthetic carbon particle has a pore size of 125 μm and the second synthetic carbon particle has a pore size of 250 μm.

A thirty-fourth embodiment which is a method of detoxifying plasma obtained from a subject having a Class A condition comprising (i) contacting the plasma with composition comprising a bimodal synthetic carbon; an anionic resin and a cationic resin.

A thirty-fifth embodiment which is the method of the thirty-fourth embodiment wherein the bimodal synthetic carbon particle is present in an amount of from about 45% to about 55%, the anionic resin is present in an amount of from about 20% to about 40%, and the cationic resin is present in an amount of from about 10% to about 20% based on the total weight of the composition.

A thirty-sixth embodiment which is the method of any preceding embodiment wherein the bimodal synthetic carbon particle, the anion exchange resin, the cation exchange resin, or combinations thereof are sanitized prior to contacting with a bodily fluid.

A thirty-seventh embodiment which is the method of any preceding embodiment wherein the bimodal synthetic carbon particle, the anion exchange resin, the cation exchange resin, or combinations thereof are contacted with a compatibilizer prior to contacting with a bodily fluid.

A thirty-eighth embodiment which is the composition of any preceding embodiment wherein the bimodal synthetic carbon particle, the anion exchange resin, the cation exchange resin, or combinations thereof are sanitized prior to contacting with a bodily fluid.

A thirty-ninth embodiment composition of any preceding embodiment wherein the bimodal synthetic carbon particle, the anion exchange resin, the cation exchange resin, or combinations thereof are contacted with a compatibilizer prior to contacting with a bodily fluid.

While embodiments of the present disclosure have been shown and described, modifications thereof can be made by one skilled in the art without departing from the spirit and teachings of the disclosure. The embodiments described herein are exemplary only, and are not intended to be limiting. Many variations and modifications of the disclosure are possible and are within the scope of the disclosure. Use of the term "optionally" with respect to any element of a claim is intended to mean that the subject element is required, or alternatively, is not required. Both alternatives are intended to be within the scope of the claim. Use of broader terms such as comprises, includes, having, etc. should be understood to provide support for narrower terms such as consisting of, consisting essentially of, comprised substantially of, etc.

Accordingly, the scope of protection is not limited by the description set out above but is only limited by the claims which follow, that scope including all equivalents of the subject matter of the claims. Each and every claim is incorporated into the specification as an embodiment of the present disclosure. Thus, the claims are a further description and are an addition to the preferred embodiments of the present disclosure. The discussion of a reference in the Background is not an admission that it is prior art to the present disclosure, especially any reference that may have a publication date after the priority date of this application. The disclosures of all patents, patent applications, and publications cited herein are hereby incorporated by reference, to the extent that they provide exemplary, procedural or other details supplementary to those set forth herein.

For the purpose of any U.S. national stage filing from this application, all publications and patents mentioned in this disclosure are incorporated herein by reference in their entireties, for the purpose of describing and disclosing the constructs and methodologies described in those publications, which might be used in connection with the methods of this disclosure. Any publications and patents discussed above and throughout the text are provided solely for their disclosure prior to the filing date of the present application. Nothing herein is to be construed as an admission that the inventors are not entitled to antedate such disclosure by virtue of prior disclosure.

Unless indicated otherwise, when a range of any type is disclosed or claimed it is intended to disclose or claim individually each possible number that such a range could reasonably encompass, including any sub-ranges encompassed therein. When describing a range of measurements every possible number that such a range could reasonably encompass can, for example, refer to values within the range with one significant digit more than is present in the end points of a range. Moreover, when a range of values is disclosed or claimed, which Applicants intent to reflect individually each possible number that such a range could reasonably encompass, Applicants also intend for the disclosure of a range to reflect, and be interchangeable with, disclosing any and all sub-ranges and combinations of sub-ranges encompassed therein. Accordingly, Applicants reserve the right to proviso out or exclude any individual members of any such group, including any sub-ranges or combinations of sub-ranges within the group, if for any reason Applicants choose to claim less than the full measure of the disclosure.

What is claimed is:

1. An extracorporeal apparatus for use in the treatment of an autoimmune disease, the extracorporeal apparatus comprising:
    a first column comprising a first composition comprising a first bimodal synthetic carbon particle;
    a second column comprising a second composition comprising a second bimodal synthetic carbon particle and an anion exchange resin, the second column being arranged in series subsequent to the first column; and
    a third column comprising a third composition comprising a third bimodal synthetic carbon particle and a cation exchange resin, the third column being arranged in series subsequent to the second column, and where the first composition, the second composition, and the third composition each have a bioburden maximum of 20 endotoxin units, are fine particulate free, and are leachables free.

2. The extracorporeal apparatus of claim 1 wherein the second composition has a weight ratio of the second bimodal synthetic carbon particle to anion exchange resin of from about 1:1 to about 5:2.

3. The extracorporeal apparatus of claim 1 wherein the third composition has a weight ratio of the third bimodal synthetic carbon particle to cation exchange resin of from about 1:1 to about 5:1.

4. The extracorporeal apparatus of claim 1, wherein the first bimodal synthetic carbon particle comprises pores having a diameter of size x and pores having a diameter of size 2x.

5. The extracorporeal apparatus of claim 1, wherein the second bimodal synthetic carbon particle comprises pores having a diameter of size y and pores having a diameter of size 2y.

6. The extracorporeal apparatus of claim 1, wherein the third bimodal synthetic carbon particle comprises pores having a diameter of size z and pores having a diameter of size 2z.

7. A method comprising contacting a bodily fluid with the an extracorporeal apparatus, the method comprising:
contacting the bodily fluid with a first composition comprising a first bimodal synthetic carbon particle to produce a first eluent;
contacting the first eluent with a second composition comprising a second bimodal synthetic carbon particle and an anion exchange resin to produce a second eluent; and
contacting the second eluent with a third composition comprising a third bimodal synthetic carbon particle and a cation exchange resin, where the first composition, the second composition, and the third composition each have a bioburden maximum of 20 endotoxin units, are fine particulate free and are leachables free.

8. The method of claim 7 wherein the extracorporeal apparatus comprises a first column, a second column, and a third column.

9. The method of claim 8 wherein the first composition is disposed within the first column, the second composition is disposed within the second column, and the third composition is disposed within the third column.

10. The method of claim 9 where there is fluid communication between the first and second column.

11. The method of claim 9 where there is fluid communication between the second and third column.

12. The method of claim 7 wherein the bodily fluid comprises whole blood.

13. An extracorporeal apparatus for use in the treatment of a Class A condition, the extracorporeal apparatus comprising:
a first column comprising a first composition comprising a first bimodal synthetic carbon particle;
a second column comprising a second composition comprising a second bimodal synthetic carbon particle and an anion exchange resin in a weight ratio of from about 10:1 to about 7:3, the second column being arranged in series subsequent to the first column; and
a third column comprising a third composition comprising a third bimodal synthetic carbon particle and a cation exchange resin in a weight ratio of from about 10:1 to about 7:3, the third column being arranged in series subsequent to the second column, and where the first composition, the second composition, and the third composition have a bioburden maximum of 20 endotoxin units, are fine particulate free, and are leachables free.

14. A method comprising contacting a bodily fluid with an extracorporeal apparatus, the method comprising:
contacting the bodily fluid with a first composition comprising a first bimodal synthetic carbon particle to produce a first eluent;
contacting the first eluent with a second composition comprising a second bimodal synthetic carbon particle and an anion exchange resin in a weight ratio of from about 10:1 to about 7:3 to produce a second eluent; and
contacting the second eluent with a third composition comprising a third bimodal synthetic carbon particle and a cation exchange resin in a weight ratio of from about 10:1 to about 7:3, where the first composition, the second composition, and the third composition have a bioburden maximum of 20 endotoxin units, are fine particulate free, and are leachables free.

15. The method of claim 14 wherein the extracorporeal apparatus comprises a first column, a second column, and a third column.

16. The method of claim 15 wherein the first component is disposed within the first column, the second component is disposed within the second column, and the third component is disposed within the third column.

17. The method of claim 16 where there is fluid communication between the first and second column.

18. The method of claim 16 where there is fluid communication between the second and third column.

19. The method of claim 14 wherein the bodily fluid comprises whole blood.

* * * * *